US008846637B2

(12) United States Patent
Seth et al.

(10) Patent No.: US 8,846,637 B2
(45) Date of Patent: Sep. 30, 2014

(54) SUBSTITUTED 2'-AMINO AND 2'-THIO-BICYCLIC NUCLEOSIDES AND OLIGOMERIC COMPOUNDS PREPARED THEREFROM

(75) Inventors: Punit P. Seth, Carlsbad, CA (US); Thazha P. Prakash, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/697,970

(22) PCT Filed: Jun. 2, 2011

(86) PCT No.: PCT/US2011/038931
§ 371 (c)(1),
(2), (4) Date: Feb. 7, 2013

(87) PCT Pub. No.: WO2011/156202
PCT Pub. Date: Dec. 15, 2011

(65) Prior Publication Data
US 2013/0131147 A1    May 23, 2013

Related U.S. Application Data

(60) Provisional application No. 61/352,516, filed on Jun. 8, 2010.

(51) Int. Cl.
| *A61K 31/70* | (2006.01) |
| *C07H 17/00* | (2006.01) |
| *C07H 21/04* | (2006.01) |
| *C07H 19/06* | (2006.01) |
| *C07H 21/00* | (2006.01) |
| *C12N 15/113* | (2010.01) |
| *C07H 19/173* | (2006.01) |
| *C07H 19/073* | (2006.01) |

(52) U.S. Cl.
CPC .......... *C07H 19/06* (2013.01); *C12N 2310/341* (2013.01); *C07H 21/04* (2013.01); *C12N 2310/3231* (2013.01); *C07H 21/00* (2013.01); *C12N 15/113* (2013.01); *C07H 19/173* (2013.01); *C12N 2310/3341* (2013.01); *C07H 19/073* (2013.01)
USPC .............. 514/45; 514/49; 536/27.1; 536/28.1

(58) Field of Classification Search
None
See application file for complete search history.

(56) References Cited

U.S. PATENT DOCUMENTS

| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |

(Continued)

FOREIGN PATENT DOCUMENTS

| WO | WO 99/14226 | 3/1999 |
| WO | WO 2004/069992 | 8/2004 |

(Continued)

OTHER PUBLICATIONS

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

Altmann et al., "Second-generation antisense oligonucleotides: structure-activity relationships and the design of improved signal-transduction inhibitors" Biochem. Soc. Trans. (1996) 24:630-637.

Altmann et al., "Second Generation of Antisense Oligonucleotides: From Nuclease Resistance to Biological Efficacy in Animals" Chimia (1996) 50(4):168-176.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.

(Continued)

*Primary Examiner* — Traviss C McIntosh, III
(74) *Attorney, Agent, or Firm* — Casimir Jones, S.C.

(57) ABSTRACT

Provided herein are 2'-amino and 2'-thio bicyclic nucleosides and oligomeric compounds prepared therefrom. The novel bicyclic nucleosides provided herein are expected to be useful for enhancing one or more properties of the oligomeric compounds they are incorporated into such as nuclease resistance.

36 Claims, No Drawings

(56) References Cited

U.S. PATENT DOCUMENTS

| | | | |
|---|---|---|---|
| 5,278,302 A | 1/1994 | Caruthers et al. | |
| 5,286,717 A | 2/1994 | Cohen et al. | |
| 5,319,080 A | 6/1994 | Leumann | |
| 5,321,131 A | 6/1994 | Agrawal et al. | |
| 5,359,044 A | 10/1994 | Cook et al. | |
| 5,366,878 A | 11/1994 | Pederson et al. | |
| 5,367,066 A | 11/1994 | Urdea et al. | |
| 5,378,825 A | 1/1995 | Cook et al. | |
| 5,386,023 A | 1/1995 | Sanghvi et al. | |
| 5,393,878 A | 2/1995 | Leumann | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmelner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,508,270 A | 4/1996 | Baxter et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,555 A | 10/1996 | Froehler et al. | |
| 5,567,811 A | 10/1996 | Mistura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci | |
| 5,596,091 A | 1/1997 | Switzer | |
| 5,597,909 A | 1/1997 | Urdea et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci | |
| 5,652,355 A | 7/1997 | Metelev et al. | |
| 5,652,356 A | 7/1997 | Agrawal | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,700,922 A | 12/1997 | Cook | |
| 5,721,218 A | 2/1998 | Froehler | |
| 5,750,692 A | 5/1998 | Cook et al. | |
| 5,763,588 A | 6/1998 | Matteucci et al. | |
| 5,792,608 A | 8/1998 | Swaminathan et al. | |
| 5,792,847 A | 8/1998 | Buhr et al. | |
| 5,830,653 A | 11/1998 | Froehler et al. | |
| 6,005,096 A | 12/1999 | Matteucci et al. | |
| 6,268,490 B1 | 7/2001 | Imanishi et al. | |
| 6,525,191 B1 | 2/2003 | Ramasamy | |
| 6,600,032 B1 | 7/2003 | Manoharan et al. | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 8,278,425 B2 * | 10/2012 | Prakash et al. | ............... 536/22.1 |
| 2003/0158403 A1 | 8/2003 | Manoharan et al. | |
| 2004/0014959 A1 | 1/2004 | Sorensen | |
| 2004/0171570 A1 | 9/2004 | Allerson et al. | |
| 2004/0241717 A1 | 12/2004 | Hansen et al. | |
| 2005/0130923 A1 | 6/2005 | Bhat et al. | |
| 2007/0287831 A1 | 12/2007 | Seth et al. | |
| 2008/0039618 A1 | 2/2008 | Allerson et al. | |

FOREIGN PATENT DOCUMENTS

| | | |
|---|---|---|
| WO | WO 2004/106356 | 12/2004 |
| WO | WO 2005/121371 | 12/2005 |
| WO | WO 2005/121372 | 12/2005 |
| WO | WO 2007/134181 | 11/2007 |
| WO | WO2008/150729 | * 11/2008 |
| WO | WO 2008/150729 | 12/2008 |
| WO | WO 2008/154401 | 12/2008 |
| WO | WO 2009/006478 | 1/2009 |

OTHER PUBLICATIONS

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

Belikova et al., "Synthesis of Ribonucleosides and Diribonucleoside Phosphates Containing 2-Chloro-Ethylamine and Nitrogen Mustard Residues" Tet. Lett. (1967) 37:3557-3562.

Braasch et al., "Locked nucleic acid (LNA): fine-tuning the recognition of DNA and RNA" Chem. Biol. (2001) 8:1-7.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

(56) References Cited

OTHER PUBLICATIONS

Conte et al., "Conformational properties and thermodynamics of the RNA duplex r(CGCAAAUUUGGG)2: comparison with the DNA analogue d(CGCAAATTTGGG)2" Nucleic Acids Res. (1997) 25(13):2627-2634.
Egli et al., "Probing the Influence of Stereoelectronic Effects on the Biophysical Properties of Oligonucleotides: Comprehensive Analysis of the RNA Affinity, Nuclease Resistance, and Crystal Structure of Ten 2'-O-Ribonucleic Acid Modifications" Biochemistry (2005) 44(25):9045-9057.
Elayadi et al., "Application of PNA and LNA oligomers to chemotherapy" Curr. Opinion Invens. Drugs (2001) 2:558-561.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Fire et al., "Potent and Specific Genetic Interference by Double-Stranded RNA in Caenorhabditis elegans" Nature (1998) 391:806-811.
Fluiter et al., "On the in vitro and in vivo Properties of Four Locked Nucleic Acid Nucleotides Incorporated into an Anti-H-Ras Antisense Oligonucleotide" ChemBioChem (2005) 6:1-6.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
Jurecic et al., "Long-distance DD-PCR and cDNA microarrays" Curr. Opin. Microbiol. (2000) 3:316-321.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Larson et al., "Rapid DNA Fingerprinting of Pathogens by Flow Cytometry" Cytometry (2000) 41:203-208.
Lesnik et al., "Relative Thermodynamic Stability of DNA, RNA, and DNA:RNA Hybried Duplexes: Relationship with Base Composition and Structure" Biochemistry (1995) 34:10807-10815.
Leumann, "DNA Analogues: From Supramolecular Principles to Biological Properties" Bioorg. & Med. Chem. (2002) 10:841-854.
Madden et al., "Serial analysis of gene expression: from gene discovery to target identification" DDT (2000) 5:415-425.
Martin, "Ein neuer Zugang zu 2'-O-Alkylribonucleosiden and Eigenschaften deren Oligonucleotide" Helv. Chim. Acta (1995) 78:486-504.
Mikhailov et al., "Substrate Properties of C'-Methylnucleoside and C'-Methyl-2''-Deoxynucleoside 5'Triphosphates in RNA and DNA Synthesis Reactions Catalysed by RNA and DNA Polymerases" Nucleosides & Nucleotides (1991) 10(1-3):339-343.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura et al., "A Short Primer on RNAi: RNA-Directed RNA Polymerase Acts as a Key Catalyst" Cell (2001) 107:415-418.
Pedersen et al., "Analogues of LNA (Locked Nucleic Acid): Synthesis of the 2'-Thio-LNA Ribothymidine and 5-Methylcytidine Phosphoramidites" Synthesis (2004) 4:578-582.
Prashar et al., "Reads: A Method for Display of 3'-End Fragment of Restriction Enzyme-Digested cDNAs for Analysis of Differential Gene Expression" Methods Enzymol. (1999) 303:258-272.
Saha et al., "5'-Me-DNA—A New Oligonucleotide Analog: Synthesis and Biochemical Properties" J. Org. Chem. (1995) 60:788-789.
Sanghvi, Antisense Research and Applications, Chapter 15, Crooke & Lebleu ed., CRC Press, 1993.
Scaringe, "RNA Oligonucleotide Synthesis via 5'-Silyl-2'-Orthoester Chemistry" Methods (2001) 23:206-217.
Searle et al., "On the stability of nucleic acid structures in solution: enthalpy-entropy compensations, internal rotations and reversibility" Nucleic Acids Res. (1993) 21:2051-2056.
Seth et al., "Synthesis and Biophysical Evaluation of 2',4'-Constrained 2'O-Methoxyethyl and 2',4'-Constrained 2'O-Ethyl Nucleic Acid Analogues" J. Org. Chem. (2010) 75(5):1569-1581.
Singh et al., "Synthesis of Novel Bicyclo[2.2.1] Ribonucleosides: 2'-Amino- and 2'-Thio-LNA Monomeric Nucleosides" Journal of Organic Chemistry (1998) 63(18):6078-6079.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sutcliffe et al., "TOGA: An automated parsing technology for analyzing expression of nearly all genes" PNAS (2000) 97:1976-1981.
Swayze et al., The Medicinal Chemistry of Oligonucleotides in Antisense Drug Technology 2nd edition, Chapter 6, pp. 143-182 (Crooke, S.T., ed., 2008).
Tabara et al., "RNAi in C. elegans: Soaking in the Genome Sequence" Science (1998) 282:430-431.
Tusterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wahlestedt et al., "Potent and nontoxic antisense oligonucleotide containing locked nucleic acids" Proc. Natl. Acad. Sci. USA (2000) 97: 5633-5638.
Wang et al., "Biophysical and Biochemical Properties of Oligodeoxynucleotides Containing 4'-C- and 5'-C-Substituted Thymidines" Bioorganic & Medicinal Chemistry Letters (1999) 9:885-890.
Zamecnik et al., "Inhibition of Rous sarcoma virus replication and cell transformation by a specific oligodeoxynucleotide" PNAS (1978) 75:280-284.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2011/038931 dated Sep. 28, 2011.

* cited by examiner

US 8,846,637 B2

SUBSTITUTED 2'-AMINO AND 2'-THIO-BICYCLIC NUCLEOSIDES AND OLIGOMERIC COMPOUNDS PREPARED THEREFROM

CROSS REFERENCED TO RELATED APPLICATIONS

This application is a U.S. National Phase filing under 35 U.S.C. §371 claiming priority to International Serial No. PCT/US2011/038931filed Jun. 2, 2011, which claims priority to U.S. Provisional Application 61/352,516, filed Jun. 8, 2010, each of which is incorporated herein by reference in its entirety.

FIELD OF THE INVENTION

Provided herein are novel bicyclic nucleosides, oligomeric compounds prepared therefrom and methods of using the oligomeric compounds. More particularly, 2'-amino and 2'-thio bicyclic nucleosides are provided comprising at least one further substituent group. Also provided herein are intermediates and methods useful for preparing the substituted 2'-amino and 2'-thio bicyclic nucleosides. The substituted 2'-amino and 2'-thio bicyclic nucleosides provided herein are useful for enhancing one or more properties of the oligomeric compounds they are incorporated into such as for example binding affinity. In certain embodiments, oligomeric compounds as provided herein have been shown to hybridize to a portion of a target RNA resulting in moderation of normal function of the target RNA. The oligomeric compounds are also expected to be useful as primers and probes in diagnostic applications.

SEQUENCE LISTING

The present application is being filed along with a Sequence Listing in electronic format. The Sequence Listing is provided as a file entitled CHEM0070USASEQ.txt created on Sep. 26, 2012, which is 12 Kb in size. The information in the electronic format of the sequence listing is incorporated herein by reference in its entirety.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of 5'-substituted DNA and RNA derivatives and their incorporation into oligomeric compounds has been reported in the literature (see for example: Saha et al., *J. Org. Chem.*, 1995, 60, 788-789; Wang et al., *Bioorganic & Medicinal Chemistry Letters*, 1999, 9, 885-890; and Mikhailov et al., *Nucleosides & Nucleotides*, 1991, 10(1-3), 339-343) and Leonid et al., 1995, 14(3-5), 901-905).

The synthesis of 2'-amino and 2'-thio bicyclic nucleosides has been reported in the literature (see for example: International Application PCT/DK98/00393, filed Sep. 14, 1998, and published as WO 99/14226 on Mar. 25, 1999; International Application PCT/DK2004/000097, filed Feb. 10, 2004, and published as WO 2004/069992 on Aug. 19, 2004; Singh et al., *Journal of Organic Chemistry*, 1998, 63(18), 6078-6079; Pedersen et al., *Synthesis*, 2004, 4, 578-582; U.S. Application 20040014959, published Jan. 22, 2004; and U.S. Application 2004241717, published Dec. 2, 2004).

The synthesis of 2'-amino and 2'-thio bicyclic nucleosides and their incorporation into oligomeric compounds has been reported in the literature. Selected oligos have been looked at for evaluation of Tm, in vitro activity and in vivo activity (see for example: Kumar et al., *Bioorganic & Medicinal Chemistry Letters*, 1998, 8(16), 2219-2222; and Fluiter et al., *ChemBioChem*, 2005, 6, 1-6).

BRIEF SUMMARY OF THE INVENTION

Disclosed herein are oligomeric compounds such as antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

The variables are defined individually in further detail herein. It is to be understood that the modified nucleosides and oligomeric compounds provided herein include all combinations of the embodiments disclosed and variables defined herein.

In certain embodiments, bicyclic nucleosides are provided having Formula I:

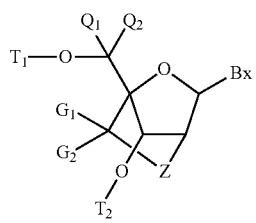

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
Z is S or NR;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O) $J_1$, O—C(=O)$NJ_1J_2$, N(H)C(=O)$NJ_1J_2$ and N(H)C(=S) $NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein at least one of $Q_1$, $Q_2$, $G_1$ and $G_2$ is other than H.

In certain embodiments, each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O) $NJ_1J_2$, N(H)C(=O)$NJ_1J_2$ and N(H)C(=S)$NJ_1J_2$.

In certain embodiments, Bx is an optionally protected pyrimidine, substituted pyrimidine, purine or substituted purine. In certain embodiments, Bx is an optionally protected uracil, 5-thiazolo-uracil, thymine, cytosine, 5-methylcytosine, 5-thiazolo-cytosine, adenine, guanine or 2,6-diaminopurine. In certain embodiments, Bx is an optionally protected uracil, thymine, cytosine, 5-methylcytosine, adenine or guanine.

In certain embodiments, at least one of $T_1$ and $T_2$ is a hydroxyl protecting group selected from acetyl, benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine -9-yl (MOX). In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, $Q_1$ and $Q_2$ are each H. In certain embodiments, one of $Q_1$ and $Q_2$ is H and the other of $Q_1$ and $Q_2$ is other than H. In certain embodiments, rein $Q_1$ and $Q_2$ are each other than H. In certain embodiments, $Q_1$ and $Q_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl. In certain embodiments, at least one of $Q_1$ and $Q_2$ is methyl.

In certain embodiments, $G_1$ and $G_2$ are each H. In certain embodiments, one of $G_1$ and $G_2$ is H and the other of $G_1$ and $G_2$ is other than H. In certain embodiments, $G_1$ and $G_2$ are each other than H. In certain embodiments, at least one of $G_1$ and $G_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl. In certain embodiments, at least one of $G_1$ and $G_2$ is methyl.

In certain embodiments, Z is NR. In certain embodiments, R is $C_1$-$C_6$ alkyl, substituted $C_1$-$C_6$ alkyl, $C_1$-$C_6$ alkoxy, substituted $C_1$-$C_6$ alkoxy or substituted acyl. In certain embodiments, R is $C_1$-$C_6$ alkyl or substituted $C_1$-$C_6$ alkyl. In certain embodiments, R is methyl. In certain embodiments, R is $C_1$-$C_6$ alkoxy or substituted $C_1$-$C_6$ alkoxy. In certain embodiments, R is methoxy. In certain embodiments, R is substituted acyl. In certain embodiments, R is C(=O)$CF_3$. In certain embodiments, R is H.

In certain embodiments, Z is S.

In certain embodiments, bicyclic nucleosides are provided having Formula Ia:

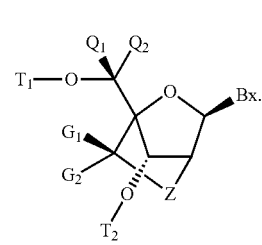

Ia

In certain embodiments, bicyclic nucleosides are provided having Formula Ia wherein three of $Q_1$, $Q_2$, $G_1$ and $G_2$ are H and the other one of $Q_1$, $Q_2$, $G_1$ and $G_2$ is other than H. In certain embodiments, bicyclic nucleosides are provided having Formula Ia wherein $Q_1$ is $CH_3$. In certain embodiments, the other three of $Q_1$, $Q_2$, $G_1$ and $G_2$ are H. In certain embodiments, bicyclic nucleosides are provided having Formula Ia wherein $Q_2$ is $CH_3$. In certain embodiments, the other three of $Q_1$, $Q_2$, $G_1$ and $G_2$ are H. In certain embodiments, bicyclic nucleosides are provided having Formula Ia wherein $G_1$ is $CH_3$. In certain embodiments, the other three of $Q_1$, $Q_2$, $G_1$ and $G_2$ are H. In certain embodiments, bicyclic nucleosides are provided having Formula Ia wherein $G_2$ is $CH_3$. In certain embodiments, the other three of $Q_1$, $Q_2$, $G_1$ and $G_2$ are H.

In certain embodiments, bicyclic nucleosides are provided having Formula Ia wherein $G_1$ and $Q_1$ are each $CH_3$ and $G_2$ and $Q_2$ are each H. In certain embodiments, bicyclic nucleosides are provided having Formula Ia wherein $G_1$ and $Q_2$ are each $CH_3$ and $G_2$ and $Q_1$ are each H. In certain embodiments, bicyclic nucleosides are provided having Formula Ia wherein $G_2$ and $Q_1$ are each $CH_3$ and $G_1$ and $Q_2$ are each H. In certain embodiments, bicyclic nucleosides are provided having Formula Ia wherein $G_2$ and $Q_2$ are each $CH_3$ and $G_1$ and $Q_1$ are each H. In certain embodiments, oligomeric compounds are provided comprising at least one bicyclic nucleoside of Formula II:

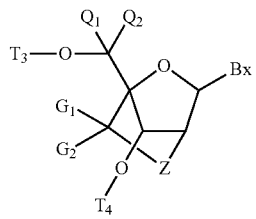

wherein independently for each bicyclic nucleoside of Formula II:

Bx is a heterocyclic base moiety;

one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

Z is S or NR;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein at least one of $Q_1$, $Q_2$, $G_1$ and $G_2$ is other than H.

In certain embodiments, each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$.

In certain embodiments, Bx is an optionally protected pyrimidine, substituted pyrimidine, purine or substituted purine for each bicyclic nucleoside of Formula II. In certain embodiments, Bx is an optionally protected uracil, 5-thiazolo-uracil, thymine, cytosine, 5-methylcytosine, 5-thiazolo-cytosine, adenine, guanine or 2,6-diaminopurine for each bicyclic nucleoside of Formula II. In certain embodiments, Bx is an optionally protected uracil, thymine, cytosine, 5-methylcytosine, adenine or guanine for each bicyclic nucleoside of Formula II.

In certain embodiments, at least one of $T_3$ and $T_4$ is a 5' or 3'-terminal group. In certain embodiments, at least one of $T_3$ and $T_4$ is a conjugate group or a phosphate moiety. In certain embodiments, one $T_3$ is a phosphate moiety.

In certain embodiments, $Q_1$ and $Q_2$ are each H for each bicyclic nucleoside of Formula II. In certain embodiments, one of $Q_1$ and $Q_2$ is H and the other of $Q_1$ and $Q_2$ is other than H for each bicyclic nucleoside of Formula II. In certain embodiments, $Q_1$ and $Q_2$ are each other than H for each bicyclic nucleoside of Formula II. In certain embodiments, at least one of $Q_1$ and $Q_2$ is substituted $C_1$-$C_6$ alkyl for each bicyclic nucleoside of Formula II. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl for each bicyclic nucleoside of Formula II. In certain embodiments, at least one of $Q_1$ and $Q_2$ is methyl for each bicyclic nucleoside of Formula II.

In certain embodiments, $G_1$ and $G_2$ are each H for each bicyclic nucleoside of Formula II. In certain embodiments, one of $G_1$ and $G_2$ is H and the other of $G_1$ and $G_2$ is other than H for each bicyclic nucleoside of Formula II. In certain embodiments, $G_1$ and $G_2$ are each other than H for each bicyclic nucleoside of Formula II. In certain embodiments, at least one of $G_1$ and $G_2$ is substituted $C_1$-$C_6$ alkyl for each bicyclic nucleoside of Formula II. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl for each bicyclic nucleoside of Formula II. In certain embodiments, at least one of $G_1$ and $G_2$ is methyl for each bicyclic nucleoside of Formula II.

In certain embodiments, Z is NR. In certain embodiments, R is $C_1$-$C_6$ alkyl, substituted $C_1$-$C_6$ alkyl, $C_1$-$C_6$ alkoxy, substituted $C_1$-$C_6$ alkoxy or substituted acyl for each bicyclic nucleoside of Formula II. In certain embodiments, R is $C_1$-$C_6$ alkyl or substituted $C_1$-$C_6$ alkyl for each bicyclic nucleoside of Formula II. In certain embodiments, R is methyl for each bicyclic nucleoside of Formula II. In certain embodiments, R is $C_1$-$C_6$ alkoxy or substituted $C_1$-$C_6$ alkoxy for each bicyclic nucleoside of Formula II. In certain embodiments, R is methoxy for each bicyclic nucleoside of Formula II. In certain embodiments, R is substituted acyl. In certain embodiments, R is C(=O)$CF_3$. In certain embodiments, R is H for each bicyclic nucleoside of Formula II.

In certain embodiments, oligomeric compounds are provided comprising at least one bicyclic nucleoside having Formula IIa:

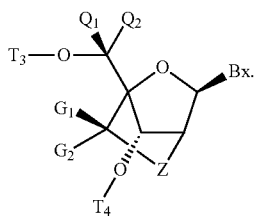

IIa

In certain embodiments, three of $Q_1$, $Q_2$, $G_1$ and $G_2$ are H and the other one of $Q_1$, $Q_2$, $G_1$ and $G_2$ is other than H for each bicyclic nucleoside of Formula IIa. In certain embodiments, $Q_1$ is $CH_3$ and $Q_2$, $G_1$ and $G_2$ are each H for each bicyclic nucleoside of Formula IIa. In certain embodiments, $Q_2$ is $CH_3$ and $Q_1$, $G_1$ and $G_2$ are each H for each bicyclic nucleoside of Formula IIa. In certain embodiments, $G_1$ is $CH_3$ and $Q_1$, $Q_2$ and $G_2$ and are each H for each bicyclic nucleoside of Formula IIa. In certain embodiments, $G_2$ is $CH_3$ and $Q_1$, $Q_2$ and $G_1$ and are each H for each bicyclic nucleoside of Formula IIa.

In certain embodiments, $G_1$ and $Q_1$ are each $CH_3$ and $G_2$ and $Q_2$ are each H for each bicyclic nucleoside of Formula IIa. In certain embodiments, $G_1$ and $Q_2$ are each $CH_3$ and $G_2$ and $Q_1$ are each H for each bicyclic nucleoside of Formula IIa. In certain embodiments, $G_2$ and $Q_1$ are each $CH_3$ and $G_1$ and $Q_2$ are each H for each bicyclic nucleoside of Formula IIa. In certain embodiments, $G_2$ and $Q_2$ are each $CH_3$ and $G_1$ and $Q_1$ are each H for each bicyclic nucleoside of Formula IIa.

In certain embodiments, oligomeric compounds are provided comprising at least one region having at least 2 contiguous bicyclic nucleosides of Formula II. In certain embodiments, oligomeric compounds are provided having at least one region comprising from 2 to 5 contiguous bicyclic nucleosides of Formula II.

In certain embodiments, oligomeric compounds are provided comprising at least two regions wherein each region independently comprises from 1 to about 5 contiguous bicyclic nucleosides of Formula II and wherein the two regions are separated by an internal region comprising at least one monomer subunit different from bicyclic nucleosides having Formula II and independently selected from nucleosides and modified nucleosides. In certain embodiments, oligomeric compounds are provided comprising gapped oligomeric compounds wherein one region of contiguous bicyclic nucleosides of Formula II is located at the 5'-end and a second region of contiguous bicyclic nucleosides of Formula II is located at the 3'-end, wherein the two regions are separated by an internal region comprising from about 6 to about 18 monomer subunits different from bicyclic nucleosides having Formula II and independently selected from nucleosides and modified nucleosides. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to three contiguous bicyclic nucleosides of Formula II, an optional second region of 1 or 2 contiguous bicyclic nucleosides of Formula II and a third region of from 8 to 14 β-D-2'-deoxyribofuranosyl nucleosides wherein said third region is located between said first and said second regions.

In certain embodiments, oligomeric compounds are provided comprising at least one bicyclic nucleoside wherein each bicyclic nucleoside has Formula IIa.

In certain embodiments, oligomeric compounds are provided wherein each internucleoside linking group is, independently, a phosphodiester internucleoside linking group or a phosphoro-thioate internucleoside linking group. In certain embodiments, oligomeric compounds are provided wherein essentially each internucleoside linking group is a phosphorothioate internucleoside linking group.

In certain embodiments, methods are provided comprising contacting a cell with an oligomeric compound as provided herein wherein said oligomeric compound is complementary to a target RNA.

In certain embodiments, bicyclic nucleosides are provided herein having Formula III:

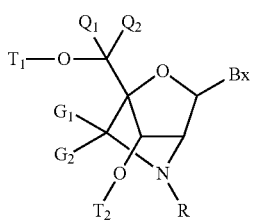

III wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
wherein at least one of $Q_1$, $Q_2$, $G_1$ and $G_2$ is other than H.

In certain embodiments, Bx is an optionally protected pyrimidine, substituted pyrimidine, purine or substituted purine. In certain embodiments, Bx is an optionally protected uracil, 5-thiazolo-uracil, thymine, cytosine, 5-methylcytosine, 5-thiazolo-cytosine, adenine, guanine or 2,6-diaminopurine.

In certain embodiments, at least one of $T_1$ and $T_2$ is a hydroxyl protecting group selected from acetyl, benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, $Q_1$ and $Q_2$ are each H. In certain embodiments, one of $Q_1$ and $Q_2$ is H and the other of $Q_1$ and $Q_2$ is other than H. In certain embodiments, $Q_1$ and $Q_2$ are each other than H. In certain embodiments, at least one of $Q_1$ and $Q_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl. In certain embodiments, at least one of $Q_1$ and $Q_2$ is methyl.

In certain embodiments, $G_1$ and $G_2$ are each H. In certain embodiments, one of $G_1$ and $G_2$ is H and the other of $G_1$ and $G_2$ is other than H. In certain embodiments, $G_1$ and $G_2$ are each other than H. In certain embodiments, at least one of $G_1$ and $G_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl. In certain embodiments, at least one of $G_1$ and $G_2$ is methyl.

In certain embodiments, R is $C_1$-$C_6$ alkyl, substituted $C_1$-$C_6$ alkyl, $C_1$-$C_6$ alkoxy, substituted $C_1$-$C_6$ alkoxy or substituted acyl. In certain embodiments, R is $C_1$-$C_6$ alkyl or substituted $C_1$-$C_6$ alkyl. In certain embodiments, one of claims 1 to 26 wherein R is methyl. In certain embodiments, R is $C_1$-$C_6$ alkoxy or substituted $C_1$-$C_6$ alkoxy. In certain embodiments, R is methoxy. In certain embodiments, R is substituted acyl. In certain embodiments, R is C(=O)CF$_3$. In certain embodiments, R is H.

In certain embodiments, bicyclic nucleosides are provided having the configuration of Formula IIIa:

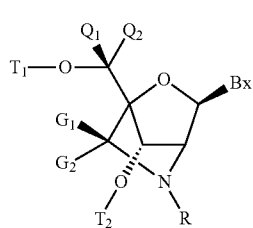

IIIa wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group comprises one or more optionally protected substituent groups independently selected from halogen, $OJ_1$, $C_1$-$C_6$ alkyl, halogen substituted $C_1$-$C_6$ alkyl, $C_2$-$C_6$ alkenyl, $C_2$-$C_6$ alkynyl, $N(J_1)(J_2)$, =$NJ_1$, $SJ_1$, $N_3$, CN, OC(=L)$J_1$, OC(=L)N($J_1$)($J_2$) and C(=L)N($J_1$)($J_2$);
L is O, S or $NJ_3$;
each $J_1$, $J_2$ and $J_3$ is, independently, H or $C_1$-$C_6$ alkyl; and
wherein at least one of $Q_1$, $Q_2$, $G_1$ and $G_2$ is other than H.

In certain embodiments, three of $Q_1$, $Q_2$, $G_1$ and $G_2$ are H and the other one of $Q_1$, $Q_2$, $G_1$ and $G_2$ is other than H.

In certain embodiments, $Q_1$ is $CH_3$. In certain embodiments, $Q_2$ is $CH_3$.

In certain embodiments, $G_1$ is $CH_3$. In certain embodiments, $G_2$ is $CH_3$.

In certain embodiments, oligomeric compounds are provided comprising at least one bicyclic nucleoside of Formula IV:

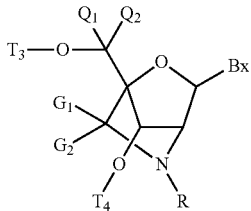

IV wherein independently for each bicyclic nucleoside of Formula IV:
Bx is a heterocyclic base moiety;
one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, $SJ_1$, $N_3$, CN, OC(=L)$J_1$, OC(=L)N($J_1$)($J_2$) and C(=L)N($J_1$)($J_2$);
L is O, S or $NJ_3$;
each $J_1$, $J_2$ and $J_3$ is, independently, H or $C_1$-$C_6$ alkyl; and
wherein at least one of $Q_1$, $Q_2$, $G_1$ and $G_2$ is other than H.

In certain embodiments, Bx is an optionally protected pyrimidine, substituted pyrimidine, purine or substituted purine for each bicyclic nucleoside of Formula IV. In certain embodiments, Bx is an optionally protected uracil, 5-thiazolo-uracil, thymine, cytosine, 5-methylcytosine, 5-thiazolocytosine, adenine, guanine or 2,6-diaminopurine for each bicyclic nucleoside of Formula IV.

In certain embodiments, at least one of $T_3$ and $T_4$ is a 5' or 3'-terminal group. In certain embodiments, at least one of $T_3$ and $T_4$ is a conjugate group or a phosphate moiety. In certain embodiments, one $T_3$ is a phosphate moiety. In certain embodiments, $Q_1$ and $Q_2$ are each H for each bicyclic nucleoside of Formula IV. In certain embodiments, $Q_1$ and $Q_2$ is H and the other of $Q_1$ and $Q_2$ is other than H for each bicyclic nucleoside of Formula IV. In certain embodiments, $Q_1$ and $Q_2$ are each other than H for each bicyclic nucleoside of Formula IV. In certain embodiments, at least one of $Q_1$ and $Q_2$ is substituted $C_1$-$C_6$ alkyl for each bicyclic nucleoside of Formula IV. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl for each bicyclic nucleoside of Formula IV. In certain embodiments, at least one of $Q_1$ and $Q_2$ is methyl for each bicyclic nucleoside of Formula IV.

In certain embodiments, $G_1$ and $G_2$ are each H for each bicyclic nucleoside of Formula IV. In certain embodiments, one of $G_1$ and $G_2$ is H and the other of $G_1$ and $G_2$ is other than H for each bicyclic nucleoside of Formula IV. In certain embodiments, $G_1$ and $G_2$ are each other than H for each bicyclic nucleoside of Formula IV. In certain embodiments, at least one of $G_1$ and $G_2$ is substituted $C_1$-$C_6$ alkyl for each bicyclic nucleoside of Formula IV. In certain embodiments, at least one substituent group is selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl for each bicyclic nucleoside of Formula IV. In certain embodiments, at least one of $G_1$ and $G_2$ is methyl for each bicyclic nucleoside of Formula IV.

In certain embodiments, R is $C_1$-$C_6$ alkyl, substituted $C_1$-$C_6$ alkyl, $C_1$-$C_6$ alkoxy, substituted $C_1$-$C_6$ alkoxy or substituted acyl for each bicyclic nucleoside of Formula IV. In certain embodiments, R is $C_1$-$C_6$ alkyl or substituted $C_1$-$C_6$ alkyl for each bicyclic nucleoside of Formula IV. In certain embodiments, R is methyl for each bicyclic nucleoside of Formula IV. In certain embodiments, R is $C_1$-$C_6$ alkoxy or substituted $C_1$-$C_6$ alkoxy for each bicyclic nucleoside of Formula IV. In certain embodiments, R is methoxy for each bicyclic nucleoside of Formula IV. In certain embodiments, R is substituted acyl. In certain embodiments, R is $C(=O)CF_3$. In certain embodiments, R is H for each bicyclic nucleoside of Formula IV.

In certain embodiments, oligomeric compounds are provided comprising at least one bicyclic nucleoside of Formula IVa:

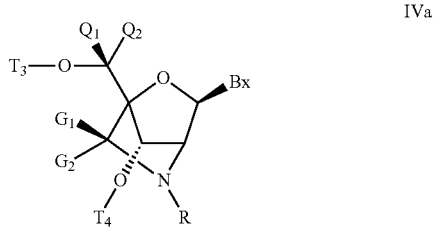

wherein independently for each bicyclic nucleoside of Formula IVa:
Bx is a heterocyclic base moiety;
one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
wherein at least one of $Q_1$, $Q_2$, $G_1$ and $G_2$ is other than H.

In certain embodiments, oligomeric compounds are provided comprising at least one bicyclic nucleoside of Formula IVa wherein three of $Q_1$, $Q_2$, $G_1$ and $G_2$ are H and the other one of $Q_1$, $Q_2$, $G_1$ and $G_2$ is other than H for each bicyclic nucleoside of Formula IVa. In certain embodiments, oligomeric compounds are provided comprising at least one bicyclic nucleoside of Formula IVa wherein $Q_1$ is $CH_3$ for each bicyclic nucleoside of Formula IVa. In certain embodiments, oligomeric compounds are provided comprising at least one bicyclic nucleoside of Formula IVa wherein $Q_2$ is $CH_3$ for each bicyclic nucleoside of Formula IVa. In certain embodiments, oligomeric compounds are provided comprising at least one bicyclic nucleoside of Formula IVa wherein $G_1$ is $CH_3$ for each bicyclic nucleoside of Formula IVa. In certain embodiments, oligomeric compounds are provided comprising at least one bicyclic nucleoside of Formula IVa wherein $G_2$ is $CH_3$ for each bicyclic nucleoside of Formula IVa.

In certain embodiments, oligomeric compounds are provided comprising at least one bicyclic nucleoside of Formula IV wherein three of $Q_1$, $Q_2$, $G_1$ and $G_2$ are H and the other one of $Q_1$, $Q_2$, $G_1$ and $G_2$ is other than H for each bicyclic nucleoside of Formula IV. In certain embodiments, oligomeric compounds are provided comprising at least one bicyclic nucleoside of Formula IV wherein $Q_1$ is $CH_3$ for each bicyclic nucleoside of Formula IV. In certain embodiments, oligomeric compounds are provided comprising at least one bicyclic nucleoside of Formula IV wherein $Q_2$ is $CH_3$ for each bicyclic nucleoside of Formula IV. In certain embodiments, oligomeric compounds are provided comprising at least one bicyclic nucleoside of Formula IV wherein $G_1$ is $CH_3$ for each bicyclic nucleoside of Formula IV. In certain embodiments, oligomeric compounds are provided comprising at least one bicyclic nucleoside of Formula IV wherein $G_2$ is $CH_3$ for each bicyclic nucleoside of Formula IV.

In certain embodiments, oligomeric compounds are provided comprising at least one region having at least 2 contiguous bicyclic nucleosides of Formula IV. In certain embodiments, oligomeric compounds are provided wherein the at least one region comprises from 2 to 5 contiguous bicyclic nucleosides of Formula IV.

In certain embodiments, oligomeric compounds are provided comprising at least two regions wherein each region independently comprises from 1 to about 5 contiguous bicyclic nucleosides of Formula IV and wherein the two regions are separated by an internal region comprising at least one monomer subunit different from bicyclic nucleosides having Formula IV and independently selected from nucleosides and modified nucleosides. In certain embodiments, oligomeric compounds are provided comprising a gapped oligomeric compound wherein one region of contiguous bicyclic nucleosides of Formula IV is located at the 5'-end and a second region of contiguous bicyclic nucleosides of Formula IV is located at the 3'-end, wherein the two regions are separated by an internal region comprising from about 6 to about 18 monomer subunits different from bicyclic nucleosides having Formula IV and independently selected from nucleosides and modified nucleosides. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to three contiguous bicyclic nucleosides of Formula IV, an optional second region of 1 or 2 contiguous bicyclic nucleosides of Formula IV and a third region of from 8 to 14 β-D-2'-deoxyribofuranosyl nucleosides wherein said third region is located between said first and said second regions.

In certain embodiments, oligomeric compounds are provided wherein each bicyclic nucleoside has Formula IVa.

In certain embodiments, oligomeric compounds are provided wherein each internucleoside linking group is, independently, a phosphodiester internucleoside linking group or a phosphoro-thioate internucleoside linking group. In certain embodiments, oligomeric compounds are provided wherein essentially each internucleoside linking group is a phosphorothioate internucleoside linking group.

In certain embodiments, methods comprising contacting a cell with an oligomeric compound as provided herein are provided wherein the oligomeric compound is complementary to a target RNA.

In certain embodiments, bicyclic nucleosides are provided having Formula V:

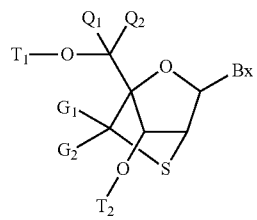

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each substituted group comprises one or more optionally protected substituent groups independently selected from halogen, $OJ_1$, $C_2$-$C_6$ alkenyl, $C_2$-$C_6$ alkynyl, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and wherein at least one of $Q_1$, $Q_2$, $G_1$ and $G_2$ is other than H.

In certain embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, adenine or guanine.

In certain embodiments, at least one of $T_1$ and $T_2$ is a hydroxyl protecting group selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, $Q_1$ and $Q_2$ are each H. In certain embodiments, one of $Q_1$ and $Q_2$ is H and the other of $Q_1$ and $Q_2$ is other than H. In certain embodiments, $Q_1$ and $Q_2$ are each other than H. In certain embodiments, at least one of $Q_1$ and $Q_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl. In certain embodiments, at least one of $Q_1$ and $Q_2$ is methyl.

In certain embodiments, $G_1$ and $G_2$ are each H. In certain embodiments, one of $G_1$ and $G_2$ is H and the other of $G_1$ and $G_2$ is other than H. In certain embodiments, $G_1$ and $G_2$ are each other than H. In certain embodiments, at least one of $G_1$ and $G_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl. In certain embodiments, at least one of $G_1$ and $G_2$ is methyl.

In certain embodiments, bicyclic nucleosides are provided having the configuration of Formula Va:

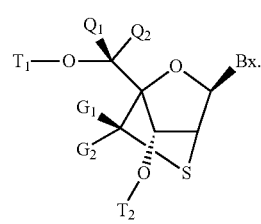

In certain embodiments, bicyclic nucleosides are provided having Formula V or Va wherein three of $Q_1$, $Q_2$, $G_1$ and $G_2$ are H and the other one of $Q_1$, $Q_2$, $G_1$ and $G_2$ is other than H. In certain embodiments, bicyclic nucleosides are provided having Formula V or Va wherein $Q_2$, $G_1$ and $G_2$ are each H and $Q_1$ is $CH_3$. In certain embodiments, bicyclic nucleosides are provided having Formula V or Va wherein $Q_1$, $G_1$ and $G_2$ are each H and $Q_2$ is $CH_3$. In certain embodiments, bicyclic nucleosides are provided having Formula V or Va wherein $Q_1$, $Q_2$ and $G_2$ are each H and $G_1$ is $CH_3$. In certain embodiments, bicyclic nucleosides are provided having Formula V or Va wherein $Q_1$, $Q_2$ and $G_1$ are each H and $G_2$ is $CH_3$.

In certain embodiments, bicyclic nucleosides are provided having Formula V or Va wherein one of $Q_1$ and $Q_2$ is H, one of $G_1$ and $G_2$ is H and the other two of $Q_1$, $Q_2$, $G_1$ and $G_2$ are other than H. In certain embodiments, bicyclic nucleosides are provided having Formula V or Va wherein $Q_2$ and $G_2$ are each H and $Q_1$ and $G_1$ are each $CH_3$. In certain embodiments, bicyclic nucleosides are provided having Formula V or Va wherein $Q_2$ and $G_1$ are each H and $Q_1$ and $G_2$ are each $CH_3$. In certain embodiments, bicyclic nucleosides are provided having Formula V or Va wherein $Q_1$ and $G_2$ are each H and $Q_2$ and $G_1$ are each $CH_3$. In certain embodiments, bicyclic nucleosides are provided having Formula V or Va wherein $Q_1$ and $G_1$ are each H and $Q_2$ and $G_2$ are each $CH_3$.

In certain embodiments, oligomeric compounds are provided comprising at least one bicyclic nucleoside of Formula VI:

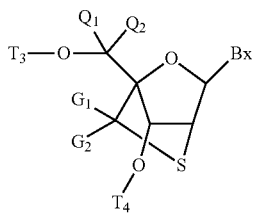

VI wherein independently for each bicyclic nucleoside of Formula VI:
  Bx is a heterocyclic base moiety;
  one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;
  $Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
  $G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
  each substituted group comprises one or more optionally protected substituent groups independently selected from halogen, $OJ_1$, $C_2$-$C_6$ alkenyl, $C_2$-$C_6$ alkynyl, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
  L is O, S or $NJ_3$;
  each $J_1$, $J_2$ and $J_3$ is, independently, H or $C_1$-$C_6$ alkyl; and
  wherein at least one of $Q_1$, $Q_2$, $G_1$ and $G_2$ is other than H.

In certain embodiments, each Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',':4,5]pyrrolo[2,3-d]pyrimidin-2-one for each bicyclic nucleoside having Formula VI. In certain embodiments, each Bx is, independently, uracil, thymine, cytosine, 5-methylcytosine, adenine or guanine for each bicyclic nucleoside having Formula VI.

In certain embodiments, at least one of $T_3$ and $T_4$ is a 5' or 3'-terminal group. In certain embodiments, at least one of $T_3$ and $T_4$ is a conjugate group or a phosphate moiety. In certain embodiments, one $T_3$ is a phosphate moiety.

In certain embodiments, $Q_1$ and $Q_2$ are each H for each bicyclic nucleoside of Formula VI. In certain embodiments, one of $Q_1$ and $Q_2$ is H and the other of $Q_1$ and $Q_2$ is other than H for each bicyclic nucleoside of Formula VI. In certain embodiments, $Q_1$ and $Q_2$ are each other than H for each bicyclic nucleoside of Formula VI. In certain embodiments, at least one of $Q_1$ and $Q_2$ is substituted $C_1$-$C_6$ alkyl for each bicyclic nucleoside of Formula VI. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $Q_1$ and $Q_2$ is $C_1$-$C_6$ alkyl for each bicyclic nucleoside of Formula VI. In certain embodiments, at least one of $Q_1$ and $Q_2$ is methyl for each bicyclic nucleoside of Formula VI.

In certain embodiments, $G_1$ and $G_2$ are each H for each bicyclic nucleoside of Formula VI. In certain embodiments, one of $G_1$ and $G_2$ is H and the other of $G_1$ and $G_2$ is other than H for each bicyclic nucleoside of Formula VI. In certain embodiments, $G_1$ and $G_2$ are each other than H for each bicyclic nucleoside of Formula VI. In certain embodiments, at least one of $G_1$ and $G_2$ is substituted $C_1$-$C_6$ alkyl for each bicyclic nucleoside of Formula VI. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $G_1$ and $G_2$ is $C_1$-$C_6$ alkyl for each bicyclic nucleoside of Formula VI. In certain embodiments, at least one of $G_1$ and $G_2$ is methyl for each bicyclic nucleoside of Formula VI.

In certain embodiments, oligomeric compounds are provided comprising at least one bicyclic nucleoside of Formula VI wherein each bicyclic nucleoside having Formula VI further has the configuration of Formula VIa:

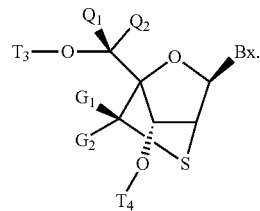

VIa

In certain embodiments, oligomeric compounds are provided wherein three of $Q_1$, $Q_2$, $G_1$ and $G_2$ are H and the other one of $Q_1$, $Q_2$, $G_1$ and $G_2$ is other than H for each bicyclic nucleoside of Formula VIa. In certain embodiments, oligomeric compounds are provided wherein $Q_2$, $G_1$ and $G_2$ are H and $Q_1$ is $CH_3$. In certain embodiments, oligomeric compounds are provided wherein $Q_1$, $G_1$ and $G_2$ are H and $Q_2$ is $CH_3$. In certain embodiments, oligomeric compounds are provided wherein $Q_1$, $Q_2$ and $G_2$ are H and $G_1$ is $CH_3$. In certain embodiments, oligomeric compounds are provided wherein $Q_1$, $Q_2$ and $G_1$ are H and $G_2$ is $CH_3$.

In certain embodiments, oligomeric compounds are provided wherein one of $Q_1$ and $Q_2$ is H, one of $G_1$ and $G_2$ is H and the other two of $Q_1$, $Q_2$, $G_1$ and $G_2$ are other than H for each bicyclic nucleoside of Formula VIa. In certain embodiments, $Q_2$ and $G_2$ are each H and $Q_1$ and $G_1$ are each $CH_3$ for each bicyclic nucleoside of Formula VIa. In certain embodiments, $Q_2$ and $G_1$ are each H and $Q_1$ and $G_2$ are each $CH_3$ for each bicyclic nucleoside of Formula VIa. In certain embodiments, $Q_1$ and $G_2$ are each H and $Q_2$ and $G_1$ are each $CH_3$ for each bicyclic nucleoside of Formula VIa. In certain embodiments, $Q_1$ and $G_1$ are each H and $Q_2$ and $G_2$ are each $CH_3$ for each bicyclic nucleoside of Formula VIa.

In certain embodiments, bicyclic nucleosides are provided comprising at least one region having at least 2 contiguous bicyclic nucleosides of Formula VI. In certain embodiments, the at least one region comprises from 2 to 5 contiguous bicyclic nucleosides of Formula VI.

In certain embodiments, bicyclic nucleosides are provided comprising at least two regions wherein each region independently comprises from 1 to about 5 contiguous bicyclic nucleosides of Formula VI and wherein the two regions are separated by an internal region comprising at least one monomer subunit different from bicyclic nucleosides having Formula VI and independently selected from nucleosides and modified nucleosides. In certain embodiments, gapped oligomeric compounds are provided wherein one region of contiguous bicyclic nucleosides of Formula VI is located at the 5'-end and a second region of contiguous bicyclic nucleosides of Formula VI is located at the 3'-end, wherein the two regions are separated by an internal region comprising from about 6 to about 18 monomer subunits different from bicyclic nucleosides having Formula VI and independently selected from nucleosides and modified nucleosides. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to three contiguous bicyclic nucleosides of Formula VI, an optional second region of 1 or 2 contiguous bicyclic nucleosides of Formula VI and a third region of from 8 to 14 β-D-2'-deoxy-ribofuranosyl nucleosides wherein said third region is located between said first and said second regions.

In certain embodiments, oligomeric compounds are provided wherein each internucleoside linking group is, independently, a phosphodiester internucleoside linking group or a phosphoro-thioate internucleoside linking group. In certain embodiments, oligomeric compounds are provided wherein essentially each internucleoside linking group is a phosphorothioate internucleoside linking group.

In certain embodiments, oligomeric compounds are provided wherein each bicyclic nucleoside has the configuration of Formula VIa.

In certain embodiments, methods are provided comprising contacting a cell with one or more oligomeric compounds as provided herein wherein the oligomeric compound is complementary to a target RNA.

DETAILED DESCRIPTION OF THE INVENTION

Provided herein are novel bicyclic nucleosides, oligomeric compounds prepared therefrom and methods of using the oligomeric compounds. More particularly, the bicyclic nucleosides provided herein comprise 2'-amino bicyclic nucleosides having at least one substituent group in addition to the optionally substituted 2'-amino group. Also provided herein are intermediates and methods for preparing the 2'-amino bicyclic nucleosides and incorporating them into oligomeric compounds. The 2'-amino bicyclic nucleosides provided herein are useful for enhancing one or more properties of the oligomeric compounds they are incorporated into such as for example binding affinity. In certain embodiments, the oligomeric compounds provided herein have shown good activity in conjunction with low toxicity. In certain embodiments, the oligomeric compounds provided herein are expected to hybridize to a portion of a target RNA resulting in loss of normal function of the target RNA.

In certain embodiments, bicyclic nucleosides are provided having Formula I:

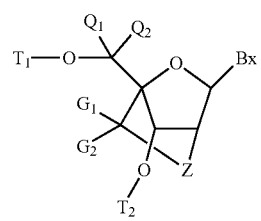

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
Z is S or NR;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein at least one of $Q_1$, $Q_2$, $G_1$ and $G_2$ is other than H.

In certain embodiments, bicyclic nucleosides are provided having Formula Ia:

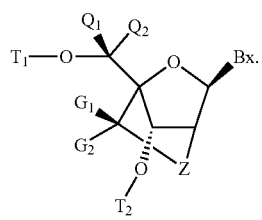

Ia

In certain embodiments, oligomeric compounds are provided comprising at least one bicyclic nucleoside of Formula II:

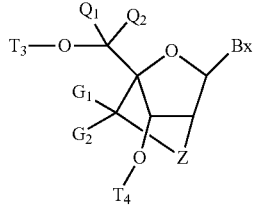

wherein independently for each bicyclic nucleoside of Formula II:

Bx is a heterocyclic base moiety;

one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

Z is S or NR;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and wherein at least one of $Q_1$, $Q_2$, $G_1$ and $G_2$ is other than H.

In certain embodiments, oligomeric compounds are provided comprising at least one bicyclic nucleoside having Formula IIa:

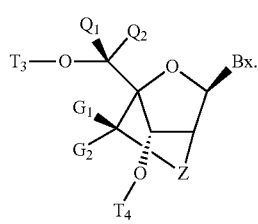

In certain embodiments, bicyclic nucleosides are provided herein having Formula III:

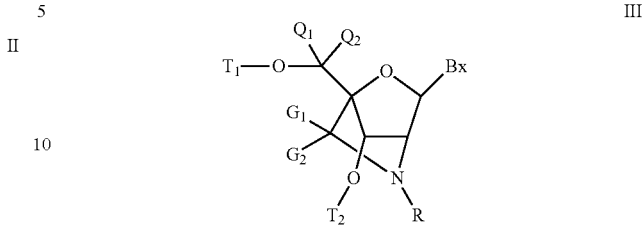

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, $SJ_1$, $N_3$, CN, OC(=L)$N(J_1)(J_2)$ and C(=L)$N(J_1)(J_2)$;

L is O, S or $NJ_3$;

each $J_1$, $J_2$ and $J_3$ is, independently, H or $C_1$-$C_6$ alkyl; and wherein at least one of $Q_1$, $Q_2$, $G_1$ and $G_2$ is other than H.

In certain embodiments, bicyclic nucleosides are provided having the configuration of Formula IIIa:

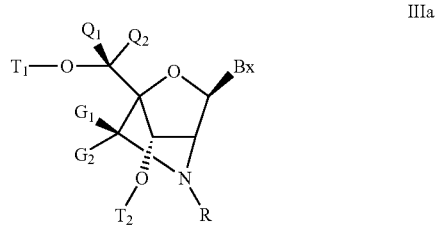

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group comprises one or more optionally protected substituent groups independently selected from halogen, Oh, $C_1$-$C_6$ alkyl, halogen substituted $C_1$-$C_6$ alkyl, $C_2$-$C_6$ alkenyl, $C_2$-$C_6$ alkynyl, $N(J_1)(J_2)$, =$NJ_1$, $SJ_1$, $N_3$, CN, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and wherein at least one of $Q_1$, $Q_2$, Gl and $G_2$ is other than H.

In certain embodiments, oligomeric compounds are provided comprising at least one bicyclic nucleoside of Formula IV:

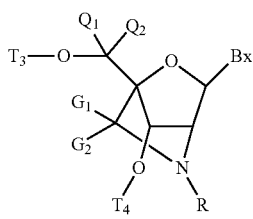

IV wherein independently for each bicyclic nucleoside of Formula IV:

Bx is a heterocyclic base moiety;

one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, =$NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and wherein at least one of $Q_1$, $Q_2$, $G_1$ and $G_2$ is other than H.

In certain embodiments, oligomeric compounds are provided comprising at least one bicyclic nucleoside of Formula IVa:

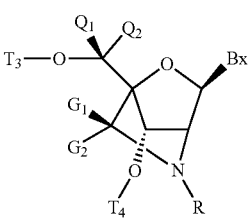

IVa wherein independently for each bicyclic nucleoside of Formula IVa:

Bx is a heterocyclic base moiety;

one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

R is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl;

each substituted group comprises one or more optionally protected substituent groups independently selected from halogen, $C_1$-$C_6$ alkyl, halogen substituted $C_1$-$C_6$ alkyl, $C_2$-$C_6$ alkenyl, $C_2$-$C_6$ alkynyl, $OJ_1$, $N(J_1)(J_2)$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and wherein at least one of $Q_1$, $Q_2$, $G_1$ and $G_2$ is other than H.

In certain embodiments, bicyclic nucleosides are provided having Formula V:

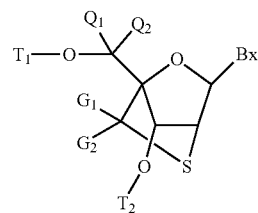

V wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group comprises one or more optionally protected substituent groups independently selected from halogen, $OJ_1$, $C_2$-$C_6$ alkenyl, $C_2$-$C_6$ alkynyl, $N(J_1)(J_2)$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and wherein at least one of $Q_1$, $Q_2$, Gl and $G_2$ is other than H.

In certain embodiments, bicyclic nucleosides are provided having the configuration of Formula Va:

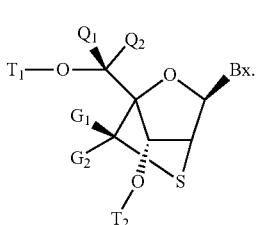

Va

In certain embodiments, oligomeric compounds are provided comprising at least one bicyclic nucleoside of Formula VI:

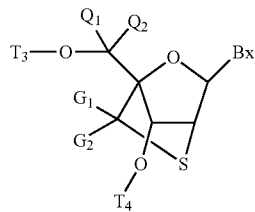

VI wherein independently for each bicyclic nucleoside of Formula VI:

Bx is a heterocyclic base moiety;
one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;

$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group comprises one or more optionally protected substituent groups independently selected from halogen, $OJ_1$, $C_2$-$C_6$ alkenyl, $C_2$-$C_6$ alkynyl, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;
each $J_1$, $J_2$ and $J_3$ is, independently, H or $C_1$-$C_6$ alkyl; and
wherein at least one of $Q_1$, $Q_2$, $G_1$ and $G_2$ is other than H.

In certain embodiments, each Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',:4,5]pyrrolo[2,3-d]pyrimidin-2-one for each bicyclic nucleoside having Formula VI. In certain embodiments, each Bx is, independently, uracil, thymine, cytosine, 5-methylcytosine, adenine or guanine for each bicyclic nucleoside having Formula VI.

In certain embodiments, oligomeric compounds are provided comprising at least one bicyclic nucleoside of Formula VI wherein each bicyclic nucleoside having Formula VI further has the configuration of Formula VIa:

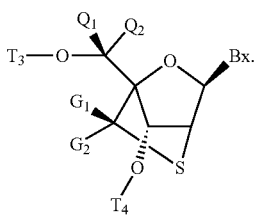

VIa

Provided herein are novel 2'-amino and 2'-thio bicyclic nucleosides and oligomeric compounds prepared therefrom. The 2'-amino and 2'-thio bicyclic nucleosides are expected to be useful for enhancing one or more properties of the oligomeric compounds they are incorporated into such as for example nuclease resistance. In certain embodiments, the oligomeric compounds provided herein are expected to hybridize to a portion of a target RNA resulting in loss of normal function of the target RNA.

In certain embodiments, the 2'-amino and 2'-thio bicyclic nucleosides provided herein can be incorporated into antisense oligomeric compounds to reduce target RNA, such as messenger RNA, in vitro and in vivo. In one aspect the reduction of target RNA is useful for inhibition of gene expression via numerous pathways. Such pathways include for example the steric blocking of transcription or translation and cleavage of mRNA via single or double stranded oligomeric compounds. The oligomeric compounds provided herein are also expected to be useful as primers and probes in diagnostic applications. In certain embodiments, oligomeric compounds comprising at least one of the 2'-amino and 2'-thio bicyclic nucleosides provided herein are expected to be useful as aptamers which are oligomeric compounds capable of binding to aberrant proteins in an in vivo setting.

Incorporation of one or more of the 2'-amino and 2'-thio bicyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

In certain embodiments, the 2'-amino and 2'-thio bicyclic nucleosides provided herein are incorporated into oligomeric compounds such that a motif results. The placement of 2'-amino and 2'-thio bicyclic nucleosides into oligomeric compounds to provide particular motifs can enhance the desired properties of the resulting oligomeric compounds for activity using a particular mechanism such as RNaseH or RNAi. Such motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as a conjugate or reporter group. The positioning of the 2'-amino and 2'-thio bicyclic nucleosides provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise 2'-amino and 2'-thio bicyclic nucleosides as provided herein.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of 2'-amino and 2'-thio bicyclic nucleosides. In certain embodiments, one or both of the 5' and 3'-ends of the contiguous sequence of 2'-amino and 2'-thio bicyclic nucleosides, comprise 5' or 3'-terminal groups such as one or more unmodified nucleosides.

As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar moieties further comprising a short region (1, 2, 3, 4 or about 5 monomer subunits) having uniform but different sugar moieties located on either the 3' or the 5' end of the oligomeric compound.

In certain embodiments, the hemimer motif comprises a contiguous sequence of from about 10 to about 28 monomer subunits having one type of sugar moiety with from 1 to 5 or from 2 to about 5 monomer subunits having a second type of sugar moiety located at one of the termini. In certain embodiments, the hemimer is a contiguous sequence of from about 8 to about 20 β-D-2'-deoxyribonucleosides having from 1-12 contiguous 2'-amino and 2'-thio bicyclic nucleosides located at one of the termini. In certain embodiments, the hemimer is a contiguous sequence of from about 8 to about 20 β-D-2'-deoxyribonucleosides having from 1-5 contiguous 2'-amino and 2'-thio bicyclic nucleosides located at one of the termini. In certain embodiments, the hemimer is a contiguous sequence of from about 12 to about 18 β-D-2'-deoxyribonucleosides having from 1-3 contiguous 2'-amino and 2'-thio bicyclic nucleosides located at one of the termini. In certain embodiments, the hemimer is a contiguous sequence of from about 10 to about 14 β-D-2'-deoxyribo-nucleosides having from 1-3 contiguous 2'-amino and 2'-thio bicyclic nucleosides located at one of the termini.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar moieties in a blockmer and only the monomer subunits in the external regions have non-naturally occurring sugar moieties in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar moieties.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous 2'-amino and 2'-thio bicyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar moieties with the internal region comprising β-D-2'-deoxyribonucleosides. In certain embodiments, the external regions each, independently, comprise from 1 to about 5 monomer subunits having non-naturally occurring sugar moieties and the internal region comprises from 6 to 18 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising 2'-amino and 2'-thio bicyclic nucleosides as disclosed herein. In certain embodiments, the gapped oligomeric compounds comprise an internal region of β-D-2'-deoxyribonucleosides with both of the external regions comprising 2'-amino and 2'-thio bicyclic nucleosides as provided herein. In certain embodiments, gapped oligomeric compounds are provided herein wherein all of the monomer subunits comprise non-naturally occurring sugar moieties.

In certain embodiments, gapped oligomeric compounds are provided comprising one or two 2'-amino and 2'-thio bicyclic nucleosides at the 5'-end, two or three 2'-amino and 2'-thio bicyclic nucleosides at the 3'-end and an internal region of from 10 to 16 β-D-2'-deoxyribonucleosides. In certain embodiments, gapped oligomeric compounds are provided comprising one 2'-amino or 2% thio bicyclic nucleosides at the 5'-end, two 2'-amino and 2'-thio bicyclic nucleosides at the 3'-end and an internal region of from 10 to 16 β-D-2'-deoxyribonucleosides. In certain embodiments, gapped oligomeric compounds are provided comprising one 2'-amino and 2'-thio bicyclic nucleosides at the 5'-end, two 2'-amino and 2'-thio bicyclic nucleosides at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length. In certain embodiments, gapped oligomeric compounds are provided that are from about 14 to about 16 monomer subunits in length.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aralkyl" and "arylalkyl," refer to an aromatic group that is covalently linked to a $C_1$-$C_{12}$alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "halo" and "halogen," refer to an atom selected from fluorine, chlorine, bromine and iodine.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

As used herein the term "mono or poly cyclic structure" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, fused through multiple ring atoms, through a substituent group or through a bifunctional linking moiety.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.,* 1977, 99, 7363-7365; Barany et al., *J. Am. Chem. Soc.,* 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE),2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyl-diphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenyl)-pethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The 2'-amino and 2'-thio bicyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry, in* 9 Volumes, Barry M. Trost, Editor-in-Chief, Pergamon Press, New York, 1993; *Advanced Organic Chemistry*, Part B: Reactions and Synthesis, 4th Edition; Carey and Sundberg, Kluwer Academic/Plenum Publishers, New York, 2001; *Advanced Organic Chemistry, Reactions, Mechanisms, and Structure,* 2nd Edition, March, McGraw Hill, 1977; Greene, T. W., and Wutz, P. G. M., *Protecting Groups in Organic Synthesis,* 4th Edition, John Wiley & Sons, New York, 1991; and Larock, R. C., *Comprehensive Organic Transformations,* 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)— or (S)—, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or logP, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein, the term "nucleobase" refers to unmodified or naturally occurring nucleobases which include, but are not limited to, the purine bases adenine (A) and guanine (G), and the pyrimidine bases thymine (T), cytosine (C) and uracil (U).

As used herein the term "heterocyclic base moiety" refers to unmodified or naturally occurring nucleobases as well as modified or non-naturally occurring nucleobases and synthetic mimetics thereof (such as for example phenoxazines). In one embodiment, a heterocyclic base moiety is any heterocyclic system that contains one or more atoms or groups of atoms capable of hydrogen bonding to a heterocyclic base of a nucleic acid.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring, synthetic or non-naturally occurring sugars having a modified furanose ring and sugar surro-gates wherein the furanose ring has been replaced with a cyclic ring system such as for example a morpholino or hexitol ring system or a non-cyclic sugar surrogate such as that used in peptide nucleic acids. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and substituted ribose), bicyclic modified sugars (such as the 2'-O—CH$_2$-4' or 2'-O—(CH$_2$)$_{2-4}$' bridged ribose derived bicyclic sugars) and sugar surrogates (such as for example when the ribose ring has been replaced with a morpholino, a hexitol ring system or an open non-cyclic system).

As used herein the term "sugar substituent group" refers to groups that are covalently attached to sugar moieties. In certain embodiments, examples of sugar substituent groups include without limitation 2'-F, 2'-allyl, 2'-amino, 2'-azido, 2'-thio, 2'-OCF$_3$, 2'-O—C$_1$-C$_{10}$ alkyl, 2'-OCH$_3$, 2'—O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_o$)(R$_q$), 2'—O(CH$_2$)$_2$NH$_2$, 2'-O—(CH$_2$)$_2$—O—N(R$_p$)(R$_q$), O(CH$_2$)$_n$ON[(CH$_2$)$_n$CH$_3$]$_2$, 2'—O(CH$_2$)$_n$ONH$_2$, 2'-O—(CH$_2$)$_2$—O—(CH$_2$)$_2$—N(R$_p$)(R$_q$), 2'-β-CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$[N(R$_p$)(R$_q$)], 5'-vinyl, 5'-methyl (R or S) and 4'-S wherein each R$_p$, R$_q$ and R$_r$ is, independently, H, substituted or unsubstituted C$_1$-C$_{10}$ alkyl or a protecting group and where n and m are from 1 to about 10. Further examples of modified sugar moieties include without limitation bicyclic sugars used in bicyclic nucleosides.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with combinations of sugar substituent groups including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein, the term "nucleoside" refers to a nucleobase-sugar combination. The two most common classes of such nucleobases are purines and pyrimidines.

As used herein, the term nucleotide refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can be an abasic nucleoside. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar moiety has a 2'-O—CHR$_a$-4' bridging group, wherein R$_a$ is H, alkyl or substituted alkyl) and base modified nucleo-sides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribnucleosides, modified nucleosides, including substituted nucleosides (such as 2', 5' and his substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides, nucleoside mimetics, nucleosides having sugar surrogates and the 2'-amino and 2'-thio bicyclic nucleosides as provided herein.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in P$^{III}$ or P$^{V}$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites (P$^{III}$ chemistry) as reactive phosphites. The intermediate phosphite compounds are subsequently oxidized to the phosphate or thiophosphate (P$^{V}$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons, preferable the 4' and the 2' carbon atoms. In certain embodiments, oligomeric compounds provided herein include one or more bicyclic nucleosides wherein the bridge comprises a 4' to 2' bicyclic nucleoside. Examples of such 4' to 2' bicyclic nucleosides, include but are not limited to one of formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-C—H(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos.: 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-$CH_2$-2',4'-$(CH_2)_2$-2', 4'-$(CH_2)_3$-$_{2'}$,4'-$CH_2$—O-2',4'-$(CH_2)_2$—O-2',4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2',4'-(CH$_2$)$_2$—O-2',4'-CH$_2$—O—N(R)-2',4'-CH(CH$_3$)—O-2',4'-CH$_2$—S-2',4'-CH$_2$—N(R)-2',4'-CH$_2$—CH(CH$_3$)-2', and 4'-(CH$_2$)$_{3-2'}$, wherein R is H, a protecting group or $C_1$-$C_{12}$ alkyl.

In certain embodiments, bicyclic nucleosides have the formula:

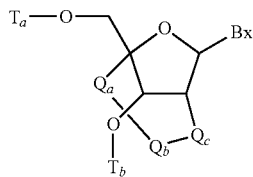

wherein:

Bx is a heterocyclic base moiety;

-$Q_a$-$Q_b$-$Q_c$- is —CH$_2$—N($R_c$)—CH$_2$—, —C(=O)—N($R_c$)—CH$_2$—, —CH$_2$—O—N($R_c$)—, —CH$_2$—N($R_c$)—O— or —N($R_c$)—O—CH$_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

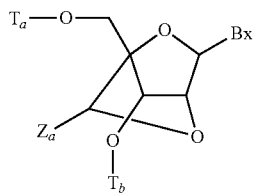

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_cC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

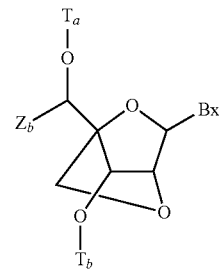

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—). In certain embodiments, bicyclic nucleosides have the formula:

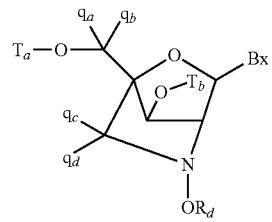

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

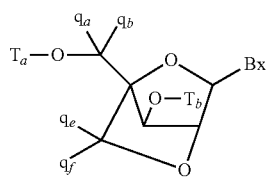

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

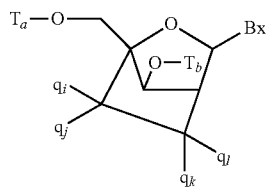

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_{3}$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

In certain embodiments, nucleosides having sugar surrogate groups include without limitation, replacement of the ribosyl ring with a sugar surrogate such as a tetrahydropyranyl ring system (also referred to as hexitol) as illustrated below:

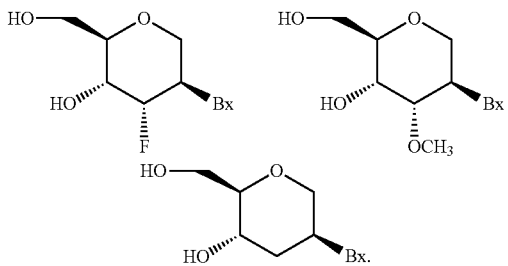

In certain embodiments, sugar surrogates are selected having the formula:

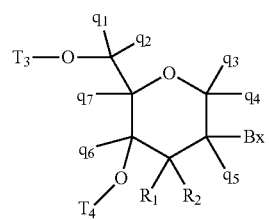

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_a$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), anitol nucleic acid (ANA), and manitol nucleic acid (MNA) (see Leumann, C. J., *Bioorg. & Med. Chem.*, 2002, 10, 841-854).

Many other monocyclic, bicyclic and tricyclic ring systems are known in the art and are suitable as sugar surrogates that can be used to modify nucleosides for incorporation into oligomeric compounds as provided herein (see for example review article: Leumann, Christian *J. Bioorg. & Med. Chem.*, 2002, 10, 841-854). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups.

In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups. In certain embodiments, oligomeric compounds comprise single-stranded oligonucleotides. In certain embodiments, oligomeric compounds comprise double-stranded duplexes comprising two oligonucleotides each. In certain embodiments, oligomeric compounds comprise one or more conjugate groups and/or terminal groups.

When preparing oligomeric compounds having specific motifs as disclosed herein it can be advantageous to mix non-naturally occurring monomer subunits such as the 2'-amino and 2'-thio bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a 2'-amino or 2'-thio bicyclic nucleosides as provided herein. In certain embodiments, oligomeric compounds are provided comprising a plurality of 2'-amino and 2'-thio bicyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

As used herein, "antisense compound" refers to an oligomeric compound, at least a portion of which is at least partially complementary to a target nucleic acid to which it hybridizes and modulates the activity, processing or expression of said target nucleic acid.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are nonionic. Neutral internucleoside linkages include without limitation, phosphotriesters, methylphosphonates, MMI (3'-$CH_2$—$N(CH_3)$—O-5'), amide-3 (3'-$CH_2$—$C(=O)$—$N(H)$-5'), amide-4 (3'-$CH_2$—$N(H)$—$C(=O)$-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl. In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

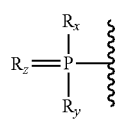

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$, is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$ wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

RNA duplexes exist in what has been termed "A Form" geometry while DNA duplexes exist in "B Form" geometry. In general, RNA:RNA duplexes are more stable, or have higher melting temperatures ($T_m$) than DNA:DNA duplexes (Sanger et al., *Principles of Nucleic Acid Structure*, 1984, Springer-Verlag; New York, N.Y.; Lesnik et al., Biochemistry, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry*, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.).

The relative ability of a chemically-modified oligomeric compound to bind to comple-mentary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helixes, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification Tm decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" means melting temperature which is the temperature at which the two strands of a duplex nucleic acid separate. $T_m$ is often used as a measure of duplex stability or the binding affinity of an antisense compound toward a complementary RNA molecule.

As used herein, "complementarity" in reference to nucleobases refers to a nucleobase that is capable of base pairing with another nucleobase. For example, in DNA, adenine (A)

is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" "in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are comple-mentary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein. As used herein, "pharmaceutically acceptable salts" refers to salts of active compounds that retain the desired biological activity of the active compound and do not impart undesired toxicological effects thereto.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods,* 2001, 23, 206-217; Gait et al.,

*Applications of Chemically synthesized RNA in RNA:Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O—[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the 2'-amino and 2'-thio bicyclic nucleosides provided herein and may also include other monomer subunits including but not limited to nucleosides, modified nucleosides, nucleosides comprising sugar surrogate groups and nucleoside mimetics.

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. Nos. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+1−32 +/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approxi-mately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Tech-nologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µl, cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µl of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 μL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
                              (SEQ ID NO: 2)
AATGGCTAAGTGAAGATGACAATCAT Reverse primer:
                              (SEQ ID NO: 3)
TGCACATATCATTACACCAGTTCGT
```

And the PCR probe:
FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 7

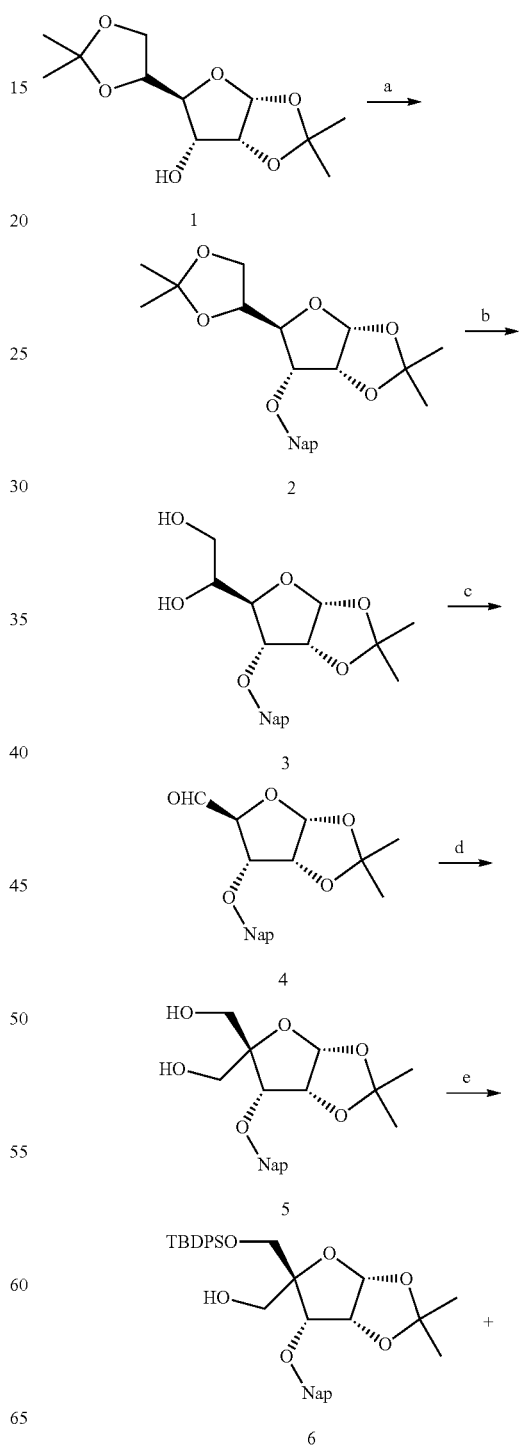

-continued

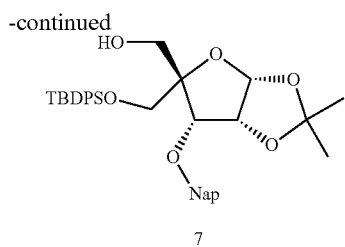

7

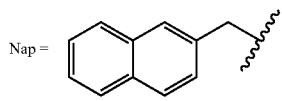

a) Preparation of Compound 2

Commercially available 1,2;5,6-di-O-isopropylidene-α-D-allofuranose, Compound 1, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more sugar (Compound 1). The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 2 (206.0 g, 99%) as an off-white solid. NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 3

Compound 2 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 2. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and brine then dried (Na$_2$SO$_4$), filtered and concentrated under reduced pressure to provide Compound 3 as a yellow foam, which was used without any further purification.

c) Preparation of Compound 4

A solution of NaIO$_4$ (107.0 g) in water (3 L) was added over 40 minutes to a stirred (mechanical stirrer) solution of Compound 3 (crude from above) in dioxane (1.5 L). After 60 minutes the reaction mixture was poured into EtOAc (1.5 L) and the organic layer was separated, washed with water (1 L) and brine (1 L) then dried (Na$_2$SO$_4$) and concentrated to provide Compound 4 as a yellow oil, which was used without any further purification.

d) Preparation of Compound 5

Compound 4 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction with stirring at room temperature for 3 days. The reaction was then poured into EtOAc (1 L) and washed with water (1 L) and brine (1 L) then evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over $P_2O_5$ to provide Compound 5 as a white solid (124 g, 66% from 44). $^1$H NMR (300 MHz, CDCl$_3$) δ: 7.85 (m, 4H), 7.48 (m, 3H), 5.75 (d, 1H, J=3.9), 4.96 (d, 1H. J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

e) Preparation of Compounds 6 and 7 tert-Butyldiphenylchlorosilane (305.0 mmol, 84.0 mL) was added to a cold (0° C.) stirring solution of Compound 5 (278.0 mmol, 100.0 g) and triethylamine (305 mmol, 43.0 mL) in dichloromethane (600 mL). After the addition was complete, the reaction was warmed to room temperature and the stirring was continued for 16 hours. MeOH (50 mL) was added (to quench the excess TBDPSCl) to the reaction and the stirring was continued for another 2 hours at room temperature. The reaction was then diluted with chloroform and the organic layer was washed with 10% HCl, saturated NaHCO$_3$, brine, dried (Na$_2$SO$_4$) and concentrated to provide a thick oil. Hexanes (150 mL) were added to the oil and the mixture was sonicated until a solution resulted. The solution was seeded with a small amount of Compound 6 (previously isolated by column chromatography). After standing for 16 hours additional hexanes were added to the thick slurry and the solid was collected by filtration. The solid was then resuspended in hexanes and stirred vigorously for 30 minutes. The solid was collected by filtration to provide 6 (80.5, 48% g) after drying under high vacuum for 16 hours. The filtrates were combined and concentrated under reduced pressure. The resulting oil was redissolved in minimum amount of hexanes and purified by silica gel column chromatography (gradient of up to 20% EtOAc in hexanes). Fractions containing Compound 7 were combined and concentrated to provide purified Compound 7. Compound 6; $^1$H NMR (300 MHz, CDCl$_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Compound 7; $^1$H NMR (300 MHz, CDCl$_3$) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

Example 14
Preparation of Compound 21
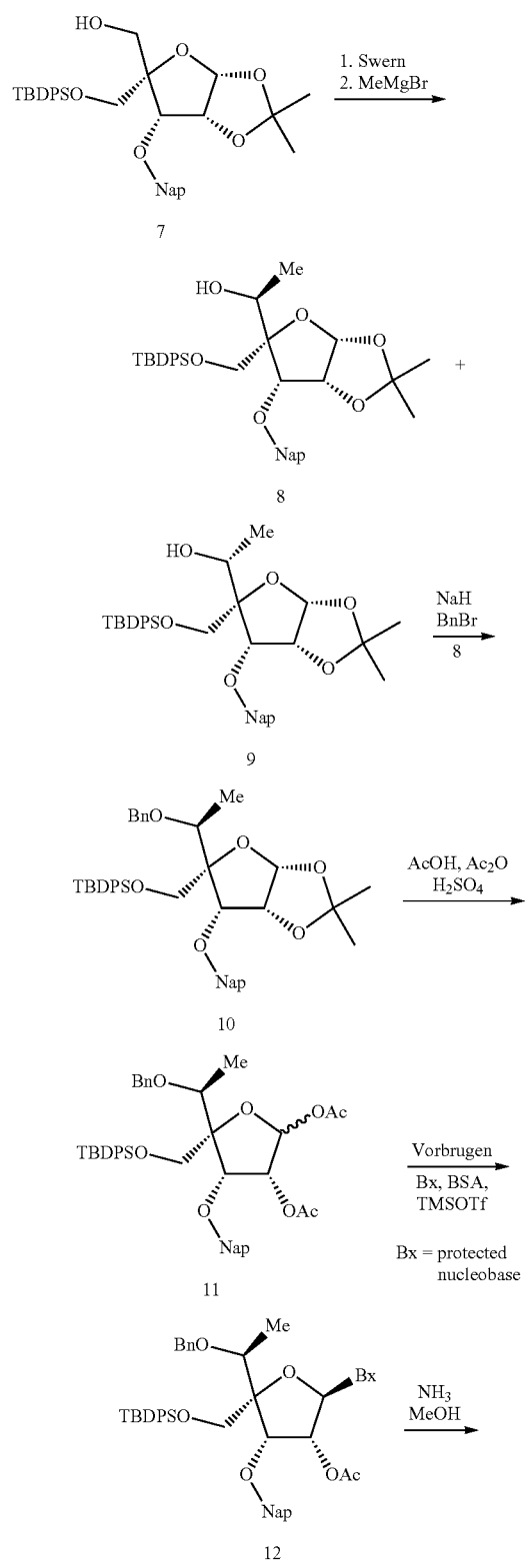
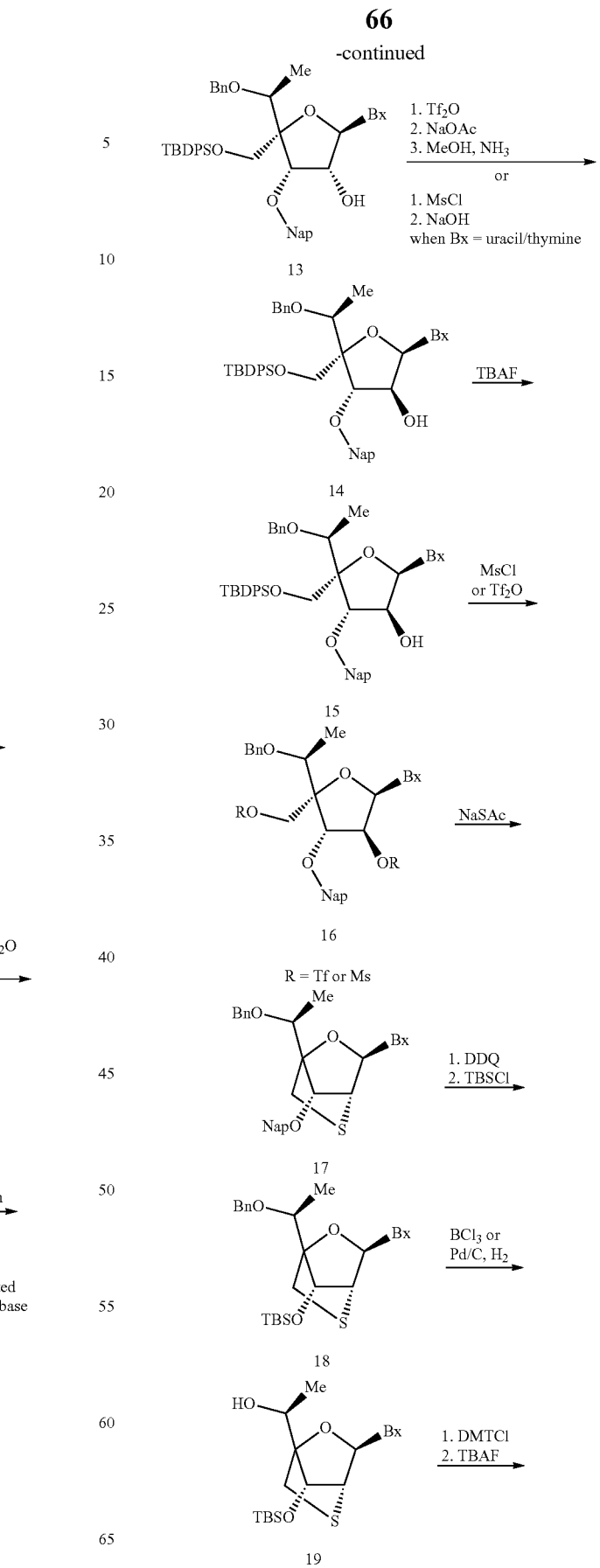

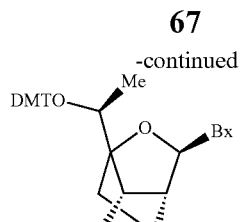
20
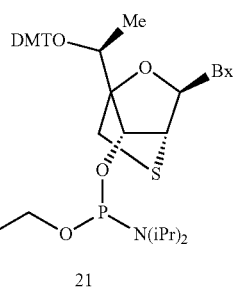
21
Compound 7 is prepared as per the procedures illustrated in Example 13.
Example 15
Preparation of Compound 33
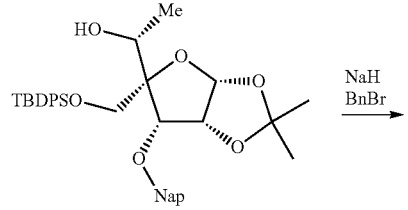
9
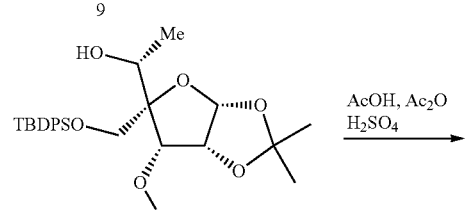
22
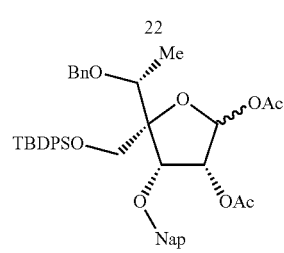
23
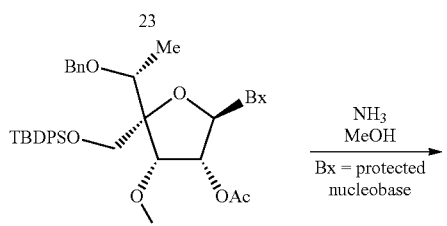
24
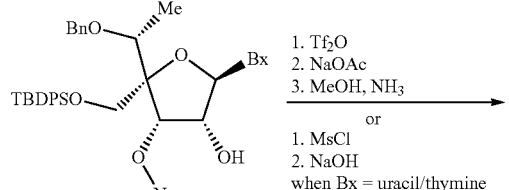
25
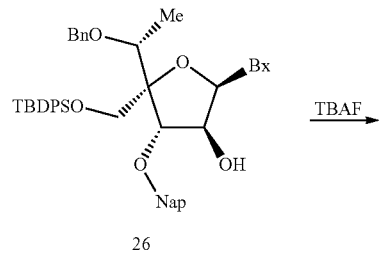
26
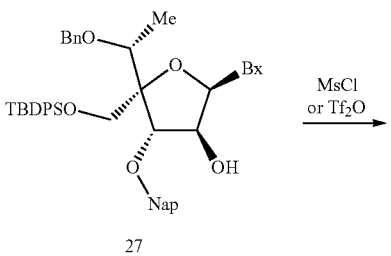
27
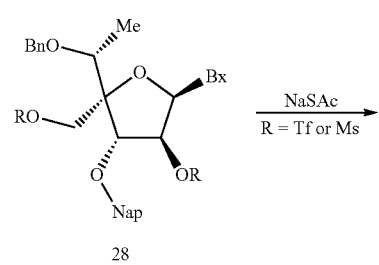
28
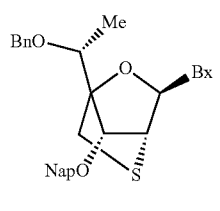
29
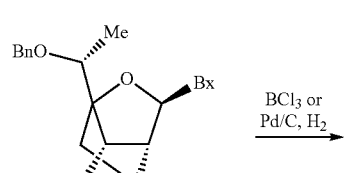
30

69
-continued
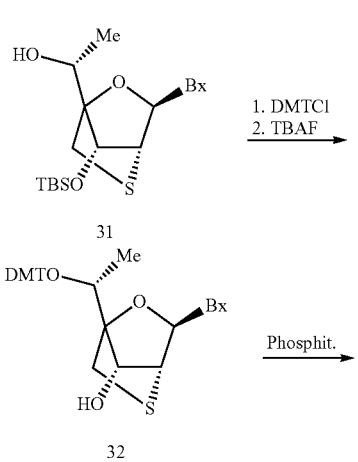
70
-continued
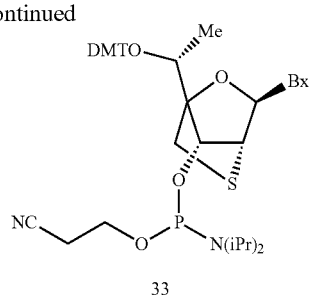
Compound 9 is prepared as per the procedures illustrated in Example 14.
Example 16
Preparation of Compounds 37 and 38
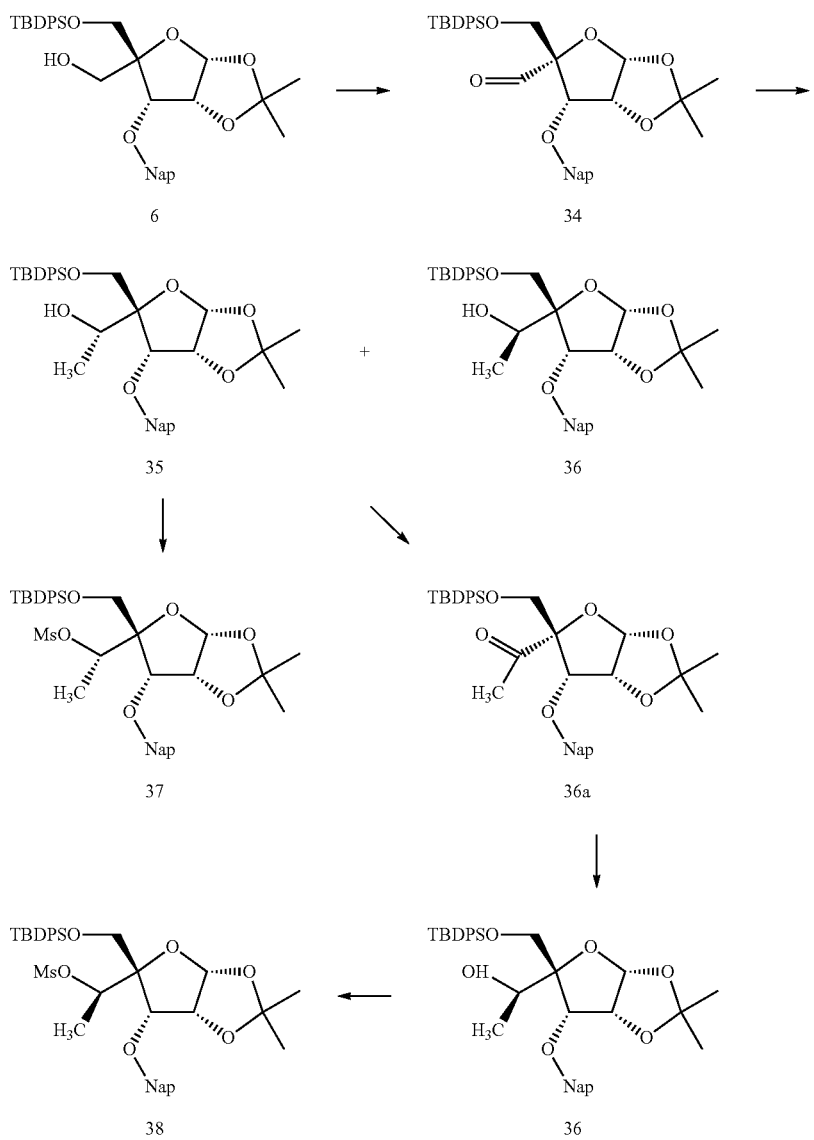

a) Preparation of Compound 34

Compound 6 is prepared as per the procedures illustrated in Example 13. Dimethylsulfoxide (10.8 mL, 152.0 mmol) was added dropwise to a cold (−78° C.) solution of oxalyl chloride (6.7 mL, 76.0 mmol) in dichloromethane (400 mL). After stirring for 30 min, a solution of Compound 6 (34.2 g, 56.4 mmol) in dichloromethane (40 mL) was added to the reaction mixture. The stirring was continued for 45 min at −78° C. and triethylamine (31.4 mL, 224.0 mmol) was added. After stirring for 15 min at −78° C., the ice bath was removed and the reaction was allowed to gradually warm to rt over 45 min. The reaction was diluted with dichloromethane and the organic phase was sequentially washed with 5% aqueous HCl, saturated sodium bicarbonate, brine, then dried over $Na_2SO_4$ and concentrated in vacuo to provide Compound 34, which was used without any further purification.

b) Preparation of Compound 36

A suspension of cerium III chloride (9.2 g, 37.5 mmol) in THF (400 mL) was stirred at rt for 60 min. The reaction was cooled in an ice bath and methyl magnesium bromide (75.0 mL of a 1.0 M solution in THF) was added over 5 min. After stirring at 0° C. for 90 min, the reaction was cooled to −78° C. and a solution of crude aldehyde, Compound 34 in THF (75 mL) was added to the reaction mixture. After 3 h at −78° C., the reaction was allowed to gradually warm to rt and carefully quenched with saturated ammonium chloride. The reaction was diluted with ethyl acetate and the organic layer was sequentially washed with 5% HCl, saturated sodium bicarbonate, brine, then dried over $Na_2SO_4$ and concentrated under reduced pressure. The resulting residue was purified using silica gel column chromatography eluting with 10 to 30% ethyl acetate in hexanes to provide the pure alcohol, Compound 35 (7.4 g, 21% from Compound 6) and a mixture of Compounds 35 and 36 (26.3 g, 76% from Compound 6, Compounds 35:36=10:1) was recovered as viscous oils.

Compound 35; $^1$H NMR (300 MHz, $CDCl_3$) ☐: 7.89-7.79 (m, 4 H), 7.65-7.26 (m, 13 H), 5.84 (d, J=3.6 Hz, 1 H), 5.05 (d, J=11.5 Hz, 1 H), 4.83-4.53 (m, 4 H), 3.91 (d, J=11.1 Hz, 1 H), 3.84 (d, J=11.1 Hz, 1 H), 3.36 (s, 1 H), 1.63 (s, 3 H), 1.39 (s, 3 H), 1.10 (d, J=6.6 Hz, 3 H), 0.91 (s, 9 H). $^{13}$C NMR (75 MHz, $CDCl_3$) ☐: 135.6, 135.5, 134.4, 133.3, 133.3, 133.2, 133.1, 129.7, 129.7, 128.7, 128.0, 127.8, 127.7, 127.7, 127.2, 126.4, 126.3, 125.7, 113.8, 104.8, 88.6, 79.4, 78.3, 73.0, 68.8, 62.4, 27.1, 26.8, 26.7, 19.2, 16.1. ESI-MS m/z: [M+Na]$^+$. Found 635.2, calcd 635.2907.

Compound 36; $^1$H NMR (300 MHz, $CDCl_3$) ☐: 7.88-7.78 (m, 4 H), 7.61-7.27 (m, 13 H), 5.87 (d, J=3.6 Hz, 1 H), 4.96 (d, J=12.1 Hz, 1 H), 4.74 (t, 1 H), 4.66 (d, J=12.1 Hz, 1 H), 4.54 (d, J=5.3 Hz, 1 H), 4.32-4.18 (m, 1 H), 3.69 (d, J=10.7 Hz, 1 H), 3.52 (d, J=10.7 Hz, 1 H), 3.12 (s, 1 H), 1.69 (s, 3 H), 1.39 (s, 3 H), 1.11 (d, J=6.4 Hz, 3 H), 0.90 (s, 9 H). $^{13}$C NMR (75 MHz, $CDCl_3$) ☐: 135.5, 134.8, 133.2, 133.2, 132.9, 132.8, 129.8, 129.7, 128.4, 127.9, 127.7, 126.9, 126.3, 126.1, 125.7, 114.3, 104.5, 90.4, 79.6, 78.1, 72.8, 67.1, 64.6, 26.9, 26.7, 19.1, 17.0. ESI-MS m/z: [M+Na]$^+$. Found 635.2, calcd 635.2907.

c) Alternative Methods in the Preparation of Compound 36

Dimethylsulfoxide (37.9 mL, 489.0 mmol) was added dropwise to a cold (−78° C.) solution of oxalyl chloride (21.4 mL, 244.0 mmol) in dichloromethane (800 mL). After stirring for 30 min, a solution of Compound 35 (100.0 g, 163.0 mmol) in dichloromethane (200 mL) was added to the reaction mixture. The stirring was continued for 45 min at −78° C. and triethylamine (102.0 mL, 726.0 mmol) was added. After stirring at −78° C. for 15 min, the ice bath was removed and the reaction was allowed to gradually warm to rt over 45 min. The reaction was diluted with dichloromethane and the organic phase was sequentially washed with 10% citric acid solution, saturated sodium bicarbonate, brine, then dried over $Na_2SO_4$ and concentrated under reduced pressure to provide the crude ketone, Compound 36a, which was used without any further purification.

A solution of lithium borohydride (122.0 mL of a 2M solution in THF, 244 mmol) was added drop-wise over 30 min to a cold (−78° C.) solution of Compound 36a (99.6 g, 163 mmol) in methanol (500 mL). After the addition was complete, the cooling bath was removed and the reaction was stirred for 2 h. The reaction was then cooled in an ice bath and carefully quenched with saturated $NH_4Cl$ solution and diluted with ethyl acetate. The organic layer was separated and sequentially washed with water, saturated sodium bicarbonate, brine, then dried over $Na_2SO_4$ and concentrated under reduced pressure. The resulting residue was purified using silica gel column chromatography eluting with 30% ethyl acetate in hexanes to furnish Compound 36 (97.2 g, 95%, Compounds 36:35>15:1) as a viscous oil. The spectroscopic analysis is identical to those reported above.

d) Preparation of Compound 37

Methanesulfonyl chloride (1.3 mL, 16.8 mmol) was added dropwise over 30 min to a cold (0° C.) solution of Compound 35 (7.4 g, 12.0 mmol), triethylamine (2.8 mL, 20.2 mmol) and DMAP (0.20 g, 1.7 mmol) in dichloromethane (25 mL). After stirring for 2 h, the reaction was diluted with chloroform and the organic layer was sequentially washed with 5% HCl, saturated solution of sodium bicarbonate, brine, then dried over $Na_2SO_4$ and concentrated in vacuo to provide the crude mesylate, Compound 37, which was used without any further purification. $^1$H NMR (300 MHz, $CDCl_3$) ☐: 7.86-7.79 (m, 4 H), 7.62-7.33 (m, 13 H), 5.79 (d, J=3.8 Hz, 1 H), 5.48 (m, 1 H), 4.92 (d, J=11.7 Hz, 1 H), 4.80-4.64 (m, 2 H), 4.50 (d, J=5.3 Hz, 1 H), 3.95-3.75 (m, 2 H), 3.67 (s, 1 H), 2.71 (s, 3 H), 1.63 (s, 3 H), 1.49 (d, J=6.4 Hz, 3 H), 1.37 (s, 3 H), 0.93 (s, 9 H). ESI-MS m/z: [M+Na]$^+$ found 713.1, calcd 713.2683.

e) Preparation of Compound 38

Methanesulfonyl chloride (3.0 mL, 38.6 mmol) was added dropwise over 30 min to a cold (0° C.) solution of Compound 36 (16.9 g, 27.6 mmol), triethylamine (6.5 mL, 46.0 mmol) and DMAP (0.47 g, 3.9 mmol) in dichloromethane (50 mL). After stirring for 2 h, the reaction was diluted with chloroform and the organic layer was sequentially washed with 5% HCl, saturated solution of sodium bicarbonate, brine, then dried ($Na_2SO_4$) and concentrated in vacuo to provide the crude mesylate, Compound 38, which was used without any further purification. $^1$H NMR (300 MHz, $CDCl_3$) ☐: 7.95-7.72 (m, 4 H), 7.61-7.28 (m, 13 H), 5.87 (d, J=4.1 Hz, 1 H), 5.36-5.19 (m, 1 H), 4.94 (d, J=11.7 Hz, 1 H), 4.83 (m, 1 H), 4.61 (d, J=11.7 Hz, 1 H), 4.37 (d, J=5.5 Hz, 1 H), 3.83 (d, J=10.9 Hz, 1 H), 3.69 (d, J=11.1 Hz, 1 H), 3.05 (s, 3 H), 1.67 (s, 3 H), 1.46-1.34 (m, 6 H), 0.96 (s, 9 H). $^{13}$C NMR (75 MHz, $CDCl_3$) ☐: 135.6, 135.5, 134.4, 133.2, 132.7, 132.6, 129.9, 129.9, 128.4, 127.9, 127.8, 127.7, 127.7, 127.2, 126.3, 126.2, 125.9, 114.2, 105.0, 89.1, 82.6, 80.2, 77.3, 73.1, 63.0, 38.7, 26.8, 26.8, 26.5, 19.1, 18.8. ESI-MS m/z: [M+Na]⁺. Found 713.1, calcd 713.2683.
Example 17
Preparation of Compound 47
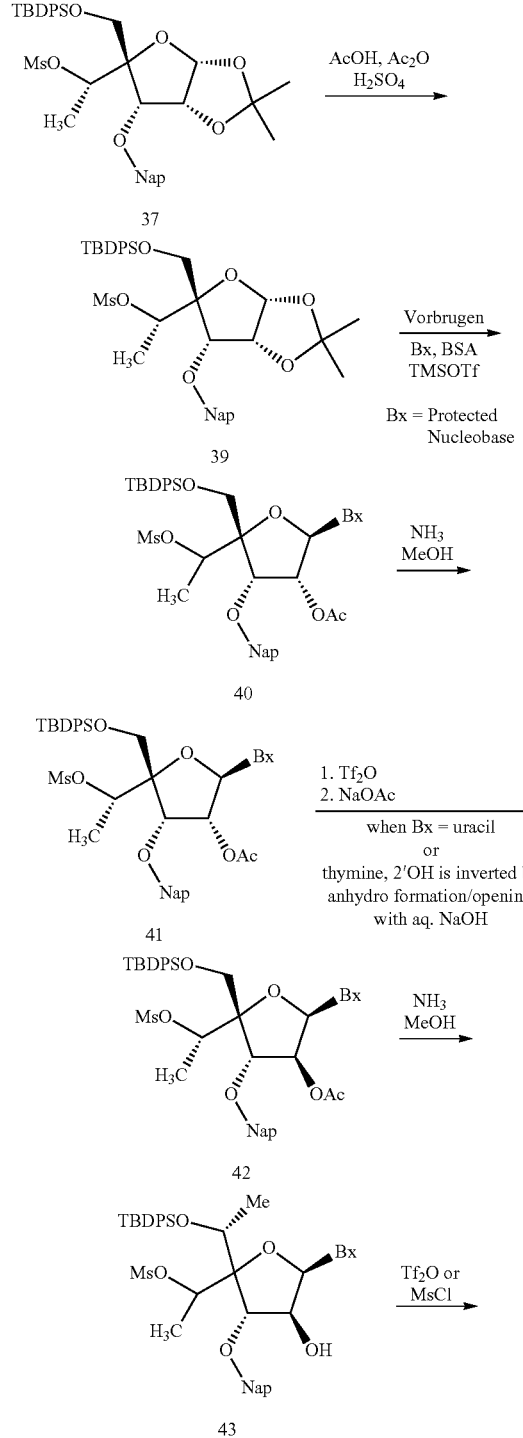
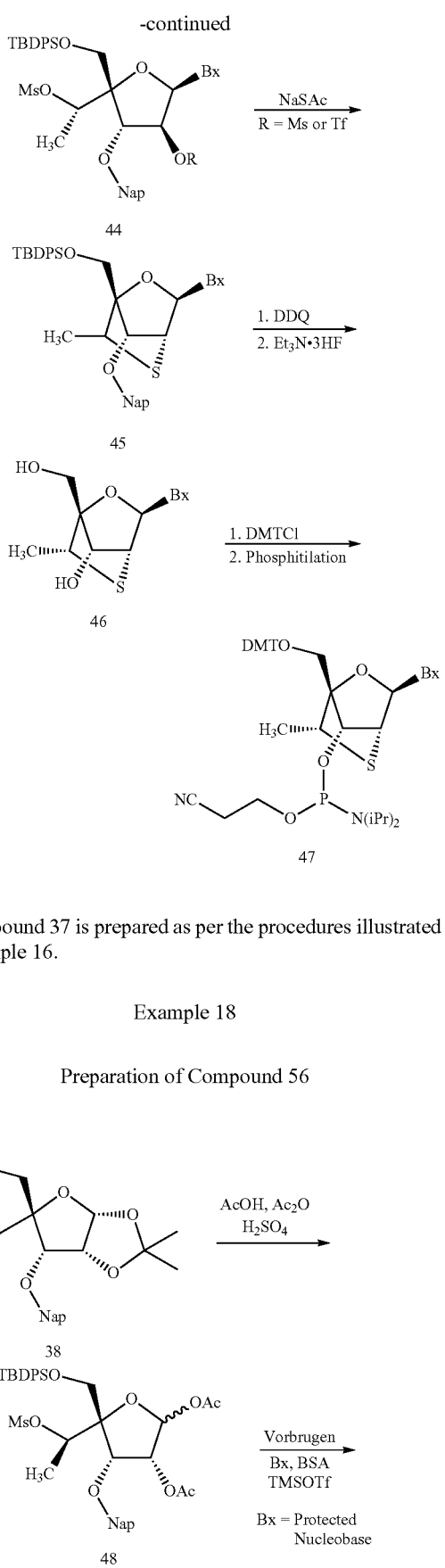
Compound 37 is prepared as per the procedures illustrated in Example 16.
Example 18
Preparation of Compound 56
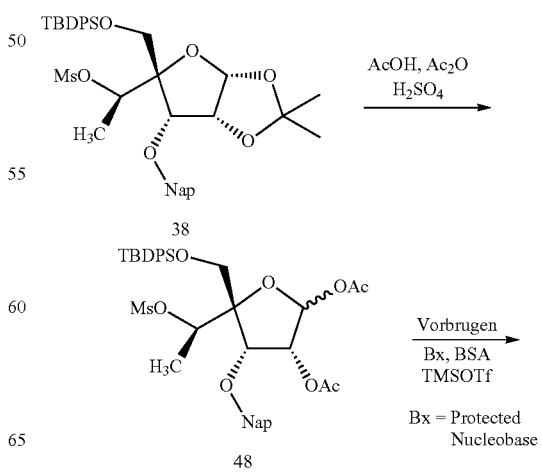

75
-continued
76
-continued
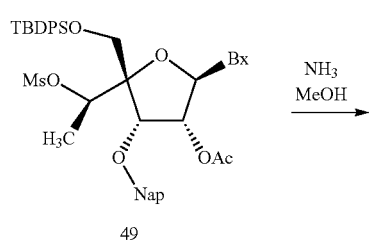
Compound 38 is prepared as per the procedures illustrated in Example 16.
Example 19
Preparation of Compound 65

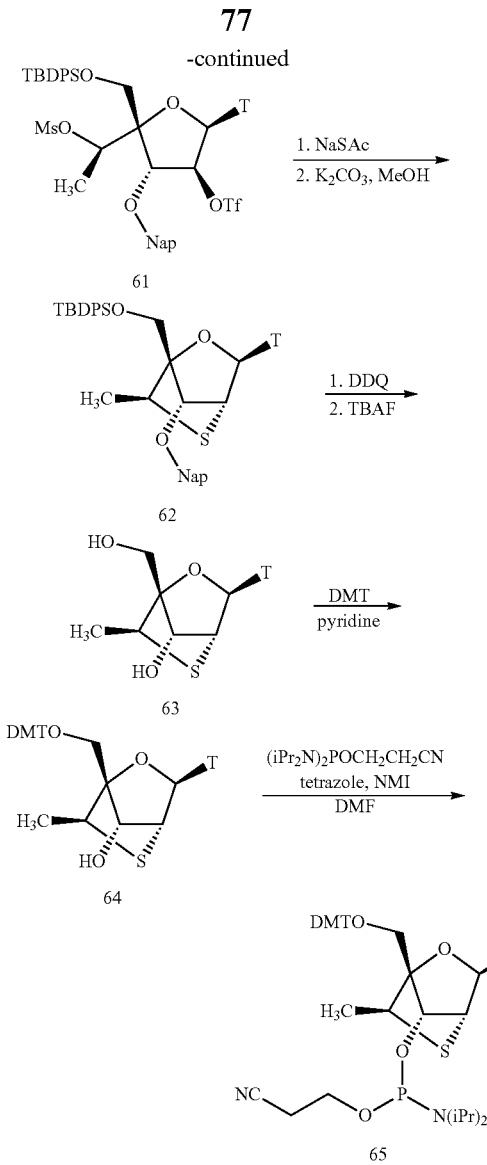

a) Preparation of Compound 57

Compound 36 was prepared according to published procedures by Seth et al., *J. Org. Chem.*, 2010, 75, 1569 (also see the procedures illustrated in Example 16). To a solution of Compound 36 (57.0 g, 93.0 mmol) in a mixture of acetic acid (250 mL) and acetic anhydride (50 mL) was added conc. $H_2SO_4$ (3.5 mL). After stirring at rt for 2 hrs, the solvent was removed in vacuo. The resulting residue was redissolved in EtOAc (500 mL) and washed with saturated aqueous $NaHCO_3$ (4×400 mL) until the pH reached ~7.5. The organic layer was then separated, dried over anhydrous $Na_2SO_4$, filtered, and evaporated to yield Compound 57 (61.8 g, 95.0%) as a light brown oil. LCMS analysis showed the product existed as a 3:1 mixture of anomers (>90% purity) and was used in subsequent reaction without further purification.

b) Preparation of Compound 58

N,O-bis-trimethylsilyl acetamide (86 mL, 354 mmol) was added to a suspension of Compound 57 (61.7 g, 88.4 mmol) and thymine (16.7 g, 132.6 mmol) in anhydrous $CH_3CN$ (500 mL). After heating at 55° C. for 1.5 h to get a homogeneous solution, the reaction mixture was cooled to 0° C. and trimethylsilyl triflate (31.9 mL, 177 mmol) was added. After stirring at 60° C. for 3.5 hrs, the reaction mixture was cooled to 0° C. and carefully quenched with saturated aqueous $NaHCO_3$ (100 mL). The mixture was concentrated in vacuo to ~75 mL and the resulting thick white residue was resuspended in ethyl acetate (500 mL), washed with saturated aq. $NaHCO_3$:saturated aq. NaCl (1:1 v/v, 4×500 mL), dried over anhydrous $Na_2SO_4$, filtered and concentrated in vacuo to afford Compound 58 (67.0 g, 99%) as an off-white foam, which was used without further purification.

c) Preparation of Compound 59

To a solution of crude Compound 58 (65.6 g, 85.8 mmol) in anhydrous methanol (500 mL) was added $K_2CO_3$ (5.9 g, 43 mmol). After stirring at rt for 96 hrs, the mixture was concentrated in vacuo to ~50 mL. The resulting residue was diluted with EtOAc (500 mL) and sequentially washed with saturated aq. $NaHCO_3$:saturated aq. NaCl (1:1 v/v, 2×500 mL) and saturated aq. NaCl (1×500 mL). The organic layer was then separated, dried over anhydrous $Na_2SO_4$, filtered, and evaporated in vacuo to afford 58 g of material. The resulting residue was subsequently dissolved in anhydrous pyridine (400 mL) and allowed to cool to 0° C. followed by treatment with methanesulfonyl chloride (19.9 mL, 257 mmol). After 12 hrs of stirring, the mixture was concentrated under reduced pressure to remove pyridine. The resulting residue was redissolved in EtOAc (500 mL), washed with half-saturated aq. $NaHCO_3$ (1×500 mL), then with half-saturated aq. NaCl (2×500 mL). The organic layer was separated, dried over anhydrous $Na_2SO_4$, filtered, and evaporated in vacuo to afford Compound 59 (71.0 g, 98%) as a light-brown foam, which was used without further purification.

d) Preparation of Compound 60

To a solution of Compound 59 (69.6 g, 83.2 mmol) in anhydrous $CH_3CN$ (400 mL) was added 1,8-diazabicyclo[5.4.0]undec-7-ene (14.9 mL, 99.9 mmol). After stirring for 2 hrs at rt, the mixture was concentrated under reduced pressure to ~50 mL. The resulting oil was diluted into EtOAc (500 mL) and sequentially washed with 2% (v/v) aq. acetic acid in half-saturated NaCl (500 mL) and saturated aq. $NaHCO_3$:saturated aq. NaCl (1:1 v/v, 2×500 mL). The organic layer was separated, dried over anhydrous $Na_2SO_4$, filtered, and evaporated. The resulting brown foam was redissolved in 1,4-dioxane (500 mL) followed by 2M NaOH (120 mL). After 1.5 hrs, the mixture was neutralized with acetic acid (14 mL) and concentrated under vacuum to yield a brown slush, which was then redissolved in EtOAc (500 mL). The resulting solution was washed with saturated aq. $NaHCO_3$:saturated aq. NaCl (1:1 v/v, 2×500 mL), dried over anhydrous $Na_2SO_4$, filtered, and evaporated in vacuo. The crude was purified by column chromatography ($SiO_2$, eluting with 1% MeOH in $CH_2Cl_2$) to furnish Compound 60 (39.6 g, 63%) as a beige foam.

e) Preparation of Compound 61

Triflic anhydride (5.6 mL, 33.2 mmol) was added to a cold solution (0° C.) of Compound 60 (18.0 g, 23.7 mmol) in anhydrous pyridine (180 mL). After stirring at 0° C. for 30 minutes, the mixture was allowed to warm to room temperature over 5 hrs. The mixture was evaporated in vacuo to provide a thick brown residue which was then redissolved in EtOAc (300 mL). The resulting solution was washed with half-saturated aq. NaCl (4×300 mL), dried over anhydrous Na$_2$SO$_4$, filtered, and evaporated to afford Compound 61 (21.1 g, quant.) as a brown foam, which was used without further purification.

f) Preparation of Compound 62

To a solution of the crude Compound 61 (20.7 g, 23.3 mmol) in anhydrous N,N-dimethylformamide (50 mL) was added KSAc (4.0 g, 35 mmol). After stirring at rt for 4 hrs, K$_2$CO$_3$ (6.4 g, 46 mmol) and MeOH (10 mL) were added to the reaction mixture and the stirring was continued for an additional 12 hrs. The resulting mixture was then poured into EtOAc (500 mL) and the organic layer was washed with saturated aq. NaHCO$_3$:saturated aq. NaCl (1:1 v/v, 4×500 mL), dried over anhydrous Na$_2$SO$_4$, filtered, and concentrated. The brown foam crude was purified by column chromatography (SiO$_2$, eluting with 30% EtOAc in hexanes) to furnish Compound 62 (8.81 g, 55.6%) as a pale yellow foam.

g) Preparation of Compound 63

To the biphasic mixture of Compound 62 (8.7 g, 12.8 mmol) in CH$_2$Cl$_2$ (80 mL) and H$_2$O (16 mL) was added 2,3-dichloro-5,6-dicyano-p-benzoquinone (5.8 g, 25 mmol). After 3.5 hrs of vigorous stirring, the mixture was poured into CH$_2$Cl$_2$ (300 mL), washed with 1% (w/v) NaHSO$_3$ (1×400 mL) and half-saturated aq. NaHCO$_3$ (3×400 mL). The organic layer was separated, dried over anhydrous Na$_2$SO$_4$, filtered, and concentrated. The yellow foam crude was purified by column chromatography (SiO$_2$, eluting with 2% MeOH in CH$_2$Cl$_2$) to afford 6.2 g of material as a pale yellow foam.

Tetrabutylammonium fluoride in THF (15 mL of 1M TBAF in THF) was then added to the solution of the purified material (6.1 g) in anhydrous THF (30 mL). After 18 hrs, the reaction mixture was concentrated under reduced pressure and redissolved in a minimal amount of CH$_2$Cl$_2$. The desilylated crude was purified by column chromatography (SiO$_2$, eluting with 4% MeOH in CH$_2$Cl$_2$) to furnish Compound 63 (3.4 g, 88% over two steps) as an off-white residue.

h) Preparation of Compound 64

To a cold solution (0° C.) of Compound 63 (3.33 g, 11.1 mmol) in anhydrous pyridine (35 mL) was added 4,4'-dimethoxytrityl chloride (6.7 g, 19 mmol). The reaction mixture was left stirring at 0° C. for 30 minutes and then allowed to warm to room temperature. After 6 hrs, excess 4,4'-dimethoxytrityl chloride was quenched with MeOH (5 mL) and the mixture was concentrated in vacuo to yield a thick, dark-gold oil. The resulting residue was diluted with CH$_2$Cl$_2$ (250 mL) and the organic layer was sequentially washed with saturated aq. NaHCO$_3$ (1×200 mL), H$_2$O (3×200 mL), dried over anhydrous Na$_2$SO$_4$, filtered, and concentrated. The crude was redissolved in a minimal amount of CH$_2$Cl$_2$ and purified by column chromatography (SiO$_2$, eluting with 2% MeOH in CH$_2$Cl$_2$) to afford 6.8 g of material as a yellow foam. Traces of pyridine residual was also removed by adding dropwise a solution of the purified material in EtOAc (15 mL) to a stirring ice-cold hexane solution (200 mL). The resulting precipitate was collected by filtration and dried under vacuum to furnish Compound 64 (5.82 g, 87%) as a pale-yellow solid.

i) Preparation of Compound 65

Tetrazole (187 mg, 2.68 mmol), N-methylimidazole (89 μL, 1.12 mmol), and 2-cyanoethyl-N,N,N',N'-tetraisopropylaminophosphorodiamidite (2.3 mL, 7.1 mmol) were added to a solution of Compound 64 (2.68 g, 4.45 mmol) in anhydrous N,N-dimethylformamide (11.1 mL). After stirring at rt for 5 hrs, triethylamine (2.4 mL, 17.8 mmol) was added and the reaction mixture was poured into EtOAc (120 mL). The organic layer was washed with saturated aq. NaCl (1×120 mL), H$_2$O (2 ×120 mL), dried over anhydrous Na$_2$SO$_4$, filtered, and concentrated. The off-white foam residue was redissolved in EtOAc (10 mL) and added dropwise to a hexane solution (100 mL) to form a precipitate. The precipitate was collected by filtration, redissolved in EtOAc, and concentrated. The crude was purified by column chromatography (SiO$_2$, eluting with 50% EtOAc in hexanes) to afford Compound 65 (2.92 g, 81.7%) as a white foam. Molecular weight (by ESI-MS), $^1$H and $^{31}$P NMR analysis were consistent with the structure as a mixture of phosphorus diastereomers. $^{31}$P NMR (CDCl$_3$): δ (ppm) 149.36, 149.11.

Example 20

Preparation of Compound 69

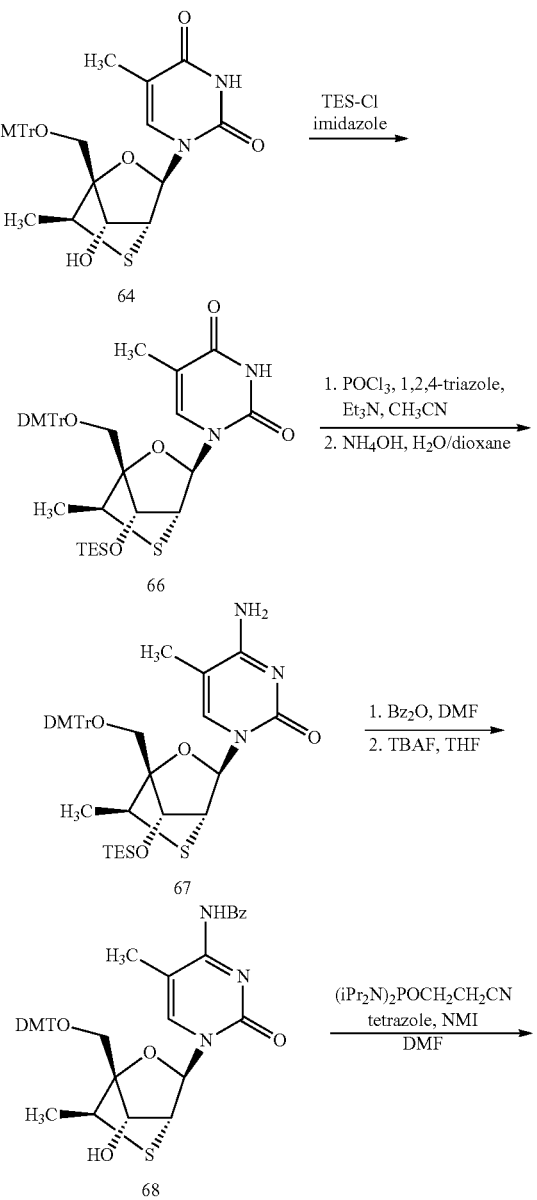

-continued

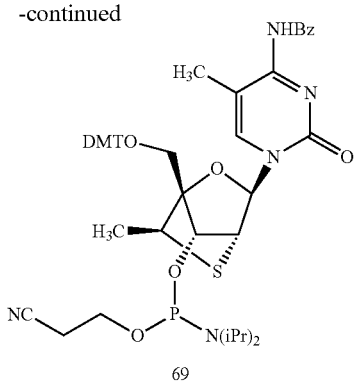

69 a) Preparation of Compound 66

Compound 64 was prepared as per the procedures illustrated in Example 19. Imidazole (2.0 g, 30 mmol) and chlorotriethylsilane (1.7 mL, 10 mmol) were added to a solution of Compound 64 (3.0 g, 5.0 mmol) in anhydrous N,N-dimethylformamide (14.2 mL). After stirring at it for 3 hrs, the reaction mixture was quenched with MeOH (3 mL) and diluted in EtOAc (150 mL). The resulting solution was washed with half-saturated aq. NaHCO$_3$ (1×150 mL), H$_2$O (4×150 mL), dried over anhydrous Na$_2$SO$_4$, filtered, and concentrated. The crude was purified by column chromatography (SiO$_2$, eluting with 2:1 hexanes:EtOAc) to yield Compound 66 (3.52 g, 98%) as a white foam.

b) Preparation of Compound 67

To a cold (0° C.) suspension of 1,2,4-triazole (4.6 g, 67 mmol) in anhydrous CH$_3$CN (100 mL) was added POCl$_3$ (1.8 mL, 19 mmol) and triethylamine (13 mL, 95 mmol). After stirring at 0° C. for 30 minutes, a solution of Compound 66 (3.42 g, 4.77 mmol) in anhydrous CH$_3$CN (18 mL) was added dropwise to the above suspension and the stirring was continued for an additional 30 minutes at 0° C. The reaction mixture was allowed to gradually warm to room temperature for 3 hours and then filtered through a glass frit to remove salts. The resulting filtrate was concentrated under vacuum to yield a white residue which was subsequently redissolved in CH$_2$Cl$_2$ (200 mL). The organic layer was washed with half-saturated aq. NaCl (2×200 mL), dried over anhydrous Na$_2$SO$_4$, filtered, and evaporated in vacuo to afford an off-white foam residue. The resulting residue was resuspended in 1,4-dioxane (43 mL) and then treated with conc. aq. NH$_4$OH (43 mL). The flask was sealed, and allowed to stir at it for 16 hours, during which time a white precipitate was formed. An additional 40 mL of H$_2$O was added and the resulting precipitate was collected by filtration. The solid was redissolved in CH$_2$Cl$_2$ (200 mL), washed with half-saturated aq. NaCl (2×200 mL), dried over anhydrous Na$_2$SO$_4$, filtered, and evaporated in vacuo to yield Compound 67 (3.27 g, 95.8%) as a white foam.

c) Preparation of Compound 68

To a solution of Compound 67 (3.15 g, 4.40 mmol) in anhydrous N,N-dimethylformamide (14.6 mL) was added benzoic anhydride (1.2 g, 5.3 mmol). After stirring at it for 18 hrs, the mixture was diluted with EtOAc (200 mL), washed with half-saturated aq. NaCl (1×200 mL) and H$_2$O (3×200 mL), dried over anhydrous Na$_2$SO$_4$, filtered, and concentrated. The crude was purified by column chromatography (SiO$_2$, eluting with 15% EtOAc in hexanes) to yield 3.30 g of purified material as a white foam.

Tetrabutylammonium fluoride in THF (4.27 mL of 1M TBAF in THF) was then added to a solution of the purified material (3.18 g, 3.85 mmol) in anhydrous THF (10.1 mL). After stirring at rt for 3 hrs, the reaction mixture was concentrated under reduced pressure and the resulting residue was purified by column chromatography (SiO$_2$, eluting with 1:1 hexanes:EtOAc) to yield Compound 68 (2.43 g, 78% over two steps) as a white foam.

d) Preparation of Compound 69

Tetrazole (140 mg, 2.0 mmol), N-methylimidazole (66 pt, 0.83 mmol) and 2-cyanoethyl-N,N,N',N'-tetraisopropylaminophosphorodiamidite (1.69 mL, 5.32 mmol) were added to a solution of Compound 68 (2.34 g, 3.3 mmol) in anhydrous N,N-dimethylformamide (8.3 mL). After 4 hours, triethylamine (8.1 mL, 13 mmol) was added and the reaction mixture was poured into EtOAc (100 mL). The organic layer was washed with saturated aq. NaCl (1×100 mL) and H$_2$O (2×100 mL), dried over anhydrous Na$_2$SO$_4$, filtered, and concentrated. The resulting residue was redissolved in EtOAc (5 mL) and precipitated by adding to a vigorously stirring hexane solution (100 mL). The precipitate was collected by filtration, redissolved in EtOAc, and concentrated. The crude was purified by column chromatography (SiO$_2$, eluting with 2:1 hexanes:EtOAc) to yield Compound 69 (2.31 g, 77%) as a white foam. Molecular weight (by ESI-MS), $^1$H and $^{31}$P NMR analysis were consistent with the structure as a mixture of phosphorus diastereomers. $^{31}$P NMR (CDCl$_3$): δ (ppm) 149.61, 149.34.

Example 21

Preparation of Compound 75

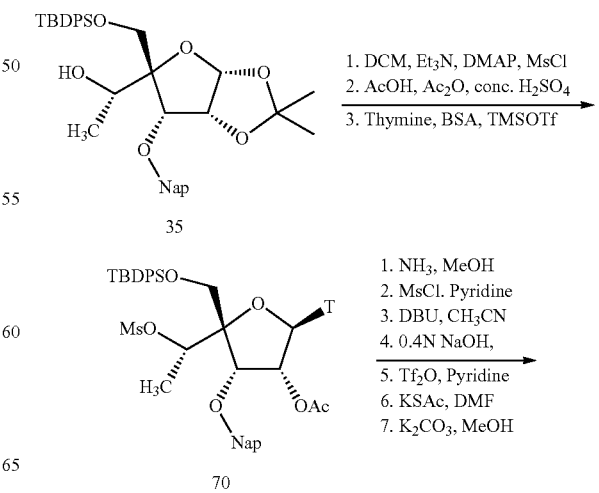

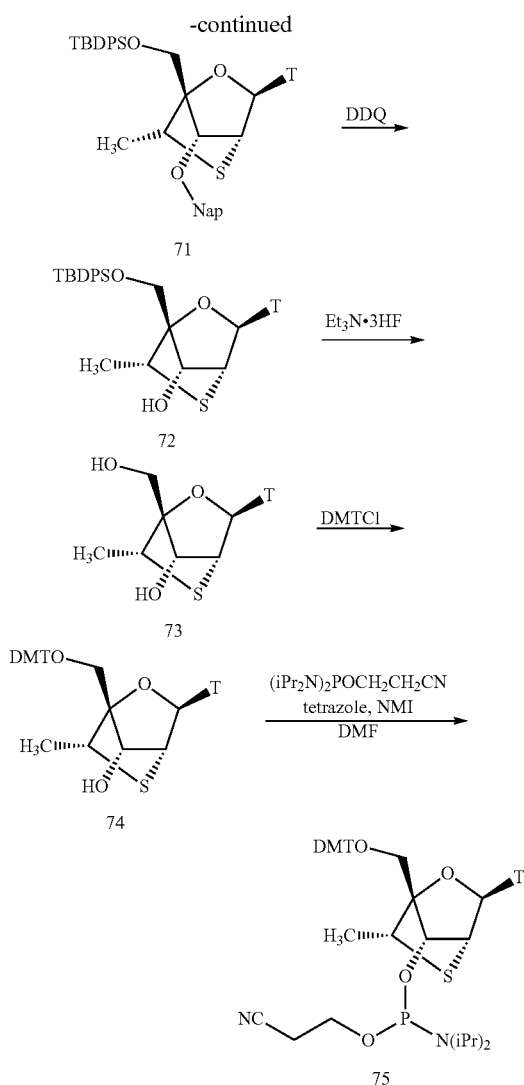

a) Preparation of Compound 70

Compound 35 was prepared according to published procedures by Seth et al., *J. Org. Chem.* 2010, 75, 1569 (also see the procedures illustrated in Example 16). To a cold (0° C.) solution of Compound 35 (48.3 g, 78.8 mmol), DMAP (1.34 g, 11 mmol), and triethylamine (18.7 mL, 134.0 mmol) in dichloromethane (160 mL) was added methanesulfonyl chloride (6.6 mL, 110 mmol). The reaction was allowed to gradually warm to room temperature and additional stirring was continued overnight. The reaction mixture was poured into dichloromethane (200 mL) and the organic layer was sequentially washed with 1N HCl (2×200 mL), brine (2×200 mL), dried over $Na_2SO_4$, filtered and concentrated to yield the crude mesylate, which was used without further purification.

To a solution of the crude mesylate (from above) in glacial acetic acid (240 mL) was added acetic anhydride (48 mL) and concentrated $H_2SO_4$ (0.2 mL). After stirring at rt for 16 hrs, the reaction mixture was concentrated and diluted with EtOAc (500 mL). The organic layer was washed sequentially with brine, saturated aq. $NaHCO_3$, brine, dried over $Na_2SO_4$ and evaporated in vacuo to yield the crude (59.3 g) as a yellow foam, which was used without further purification.

N,O-Bis(trimethylsilyl)acetamide (100 mL, 400 mmol) was added to a suspension of the crude from above (59.3 g) and thymine (22 g, 172 mmol) in $CH_3CN$ (450 mL). After heating with a heat gun to get a clear solution followed by cooling in an ice bath, trimethylsilyl triflate (0.87 mL, 4.8 mmol) was added to the reaction mixture and allowed to undergo reflux overnight. The reaction was cooled to room temperature and then poured into EtOAc (450 mL) after quenching with saturated $NaHCO_3$. The organic layer was sequentially washed with saturated $NaHCO_3$, brine, dried ($Na_2SO_4$) and concentrated under vacuum. Purification by column chromatography ($SiO_2$, eluting with 33% EtOAc in hexanes) yielded Compound 70 (62 g, 98% in three steps) as a white foam. LCMS; RT: 4.638 min. MS: m/z=M+23=824.

b) Preparation of Compound 71

A solution of methanolic ammonia (320 mL of a 7M solution) was added to a cold (0° C.) solution of Compound 70 (62 g, 77.4 mmol) in MeOH (200 mL). After stirring for 16 hrs at rt, the reaction was concentrated under reduced pressure to yield the crude, which was used without further purification.

Methanesulfonyl chloride (9 mL, 115.8 mmol) was added to a cold (0° C.) solution of the crude (from above) in pyridine (320 mL). After stirring for 16 hrs, the reaction was gradually warmed to room temperature and poured into EtOAc (800 mL). The organic layer was washed with water (3×800 mL), dried over $Na_2SO_4$ and concentrated to yield the crude (68.3 g) as a white foam, which was used without further purification.

DBU (18.3 mL, 81.6 mmol) was added to a solution of the crude (from above) in anhydrous acetonitrile (700 mL). After stirring at rt for 1 h, the reaction mixture was poured into EtOAc (500 mL). The organic layer was sequentially washed with 1N HCl, brine, saturated $NaHCO_3$, brine, dried over $Na_2SO_4$ and concentrated to yield the crude anhydro nucleoside which was used without further purification.

The crude anhydro nucleoside from above (56.6 g) was dissolved in a mixture of 1,4 dioxane (736 mL) and 3M NaOH (112 mL). After stirring at rt for 6 hrs, the reaction mixture was quenched with saturated $NH_4Cl$ and the organic layer was washed with water, brine, dried over $Na_2SO_4$, filtered and concentrated in vacuo to yield the crude as a yellow foam, which was used without further purification.

Trifluoromethanesulfonic anhydride (17.5 mL) was added to a cold (0° C.) solution of the crude from above (61 g) in anhydrous pyridine (600 mL). After stirring at rt for 16 hrs, the reaction mixture was poured into EtOAc (800 mL) and the organic layer was sequentially washed with water (3×500 mL), saturated $NH_4Cl$ (3×500 mL), brine (3×500 mL), dried over $Na_2SO_4$, filtered and concentrated under reduced pressure to yield the crude (68.2 g) as a yellow foam.

The crude triflate from above (34 g) and potassium thioacetate (6.5 g, 57.2 mmol) were suspended in DMF (75 mL) and allowed to stir at room temperature overnight. To this reaction mixture, $K_2CO_3$ (10.5 g, 76.2 mmol) and MeOH (20 mL) were added and the stirring was continued for an additional 2 hrs. The reaction mixture was then poured into EtOAc (200 mL) and the organic layer was washed with brine (3×300 mL), dried over $Na_2SO_4$ and concentrated under vacuum. Purification by column chromatography ($SiO_2$, eluting with 5-10% ethyl acetate in dichloromethane) yielded Compound 71 (14.3 g, 54% in seven steps) as a light brown foam. LCMS; RT: 5.186 min. MS: m/z=M+23=702.

c) Preparation of Compound 72

2,3-dichloro-5,6-dicyano-1,4-benzoquinone (13.2 g, 58.0 mmol) was added to a solution of Compound 71 (14.7 g, 20.7 mol) in a mixture of dichloromethane (200 mL) and water (10 mL). After stirring for 3 hrs, the reaction mixture was quenched with 10% sodium sulfite aqueous solution and poured into dichloromethane (2×100 mL). The organic layer was separated, washed with brine (2×300 mL), dried over Na$_2$SO$_4$, filtered and concentrated under vacuum. Purification by column chromatography (SiO$_2$, eluting with 5% MeOH in dichloromethane) yielded Compound 72 (10.7 g, 96%) as a light yellow foam. LCMS; RT: 4.327 min. MS: m/z=M+23=561.

d) Preparation of Compound 73

Triethylamine trihydrofluoride (120 mmol) was added to a solution of Compound 72 (10.7 g, 19.9 mmol) and triethylamine (50 mmol) in THF (200 mL). After stirring at rt for 16 hrs, the reaction mixture was poured into EtOAc (300 mL) and the organic layer was washed with brine (2×300 mL), dried over Na$_2$SO$_4$, filtered and concentrated in vacuo. Purification by column chromatography (SiO$_2$, eluting with 5-10% MeOH in dichloromethane) yielded Compound 73 (5.4 g, 92%) as a white foam. LCMS; RT: 0.635 min. MS: m/z=M+23=323.

e) Preparation of Compound 74

DMTCl (9.0 g, 26.6 mmol) was added to a cold (0° C.) solution of Compound 73 in anhydrous pyridine (180 mL). After stirring at rt for 16 hrs, the reaction mixture was poured into EtOAc (300 mL) and the organic layer was washed with water (2×300 mL), dried over Na$_2$SO$_4$, filtered and concentrated in vacuo. Purification by column chromatography (SiO$_2$, eluting with 33-50% ethyl acetate in dichloromethane) yielded Compound 74 (10.7 g, quant.) as a white foam. LCMS; RT: 3.935 min. MS: m/z=M+23=626.

f) Preparation of Compound 75

2-Cyanoethyl N,N'-tetraisopropylphosphoramidite (4.2 mL, 13.0 mmol) was added to a solution of Compound 74 (5.2 g, 8.7 mmol), tetrazole (0.5 g, 7.0 mmol), N-methylimidazole (0.2 mL, 2.2 mmol) in anhydrous DMF (45 mL). After stirring for 5 hrs at rt, the reaction was quenched with saturated sodium bicarbonate and poured into EtOAc. The organic layer was washed with 90% brine, brine, dried over Na$_2$SO$_4$, filtered and concentrated under vacuum. Purification by column chromatography (SiO$_2$, eluting with 33% ethyl acetate in hexanes) yielded Compound 75 (5.6 g, 80%). $^{31}$P NMR: 149.38, 149.11 ppm. MS: m/z=M+1=804.

Example 22

Preparation of Compound 79

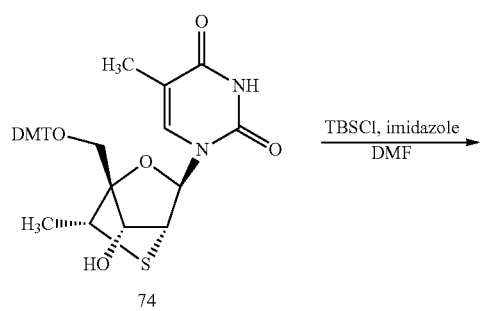
74

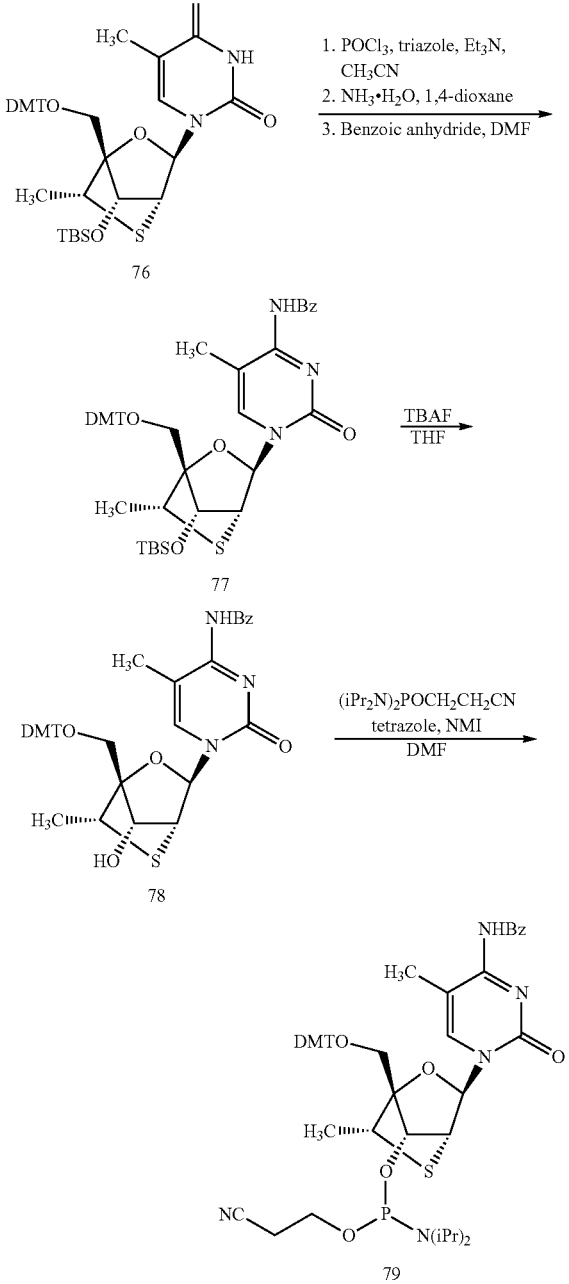

a) Preparation of Compound 76

Compound 74 was prepared as per the procedures illustrated in Example 21. tert-butyldimethylsilyl chloride (9.7 mL, 56 mmol) was added to a cold (0° C.) solution of Compound 74 (6.75 g, 11.2 mmol) and imidazole (4.6 g, 67.2 mmol) in anhydrous DMF (110 mL). After stirring for 16 hrs at rt, the reaction was quenched with saturated sodium bicarbonate and poured into EtOAc. The organic layer was washed with brine, dried over Na$_2$SO$_4$, filtered and concentrated under reduced pressure. Purification by column chromatography (SiO$_2$, eluting with 10-20% ethyl acetate in dichloromethane) yielded Compound 76 (9.6 g, quant.). LCMS; RT: 5.090 min. MS: m/z=M+23=739.

b) Preparation of Compound 77

POCl$_3$ (8.2 mL, 89.4 mmol) was added to a cold (0° C.) suspension of 1,2,4-triazole (25 g, 358.4 mmol) in anhydrous CH$_3$CN (90 mL). After stirring at 0° C. for 15 min, triethylamine (62.4 mL, 448 mmol) was added and the stirring was continued for an additional 30 min. A solution of Compound 76 (9.6 g, 11.2 mmol) in CH$_3$CN (90 mL) was then cannulated into the reaction mixture and left stirring for another 20 min at 0° C. After an additional 2 hrs, the reaction mixture was gradually warmed to room temperature and concentrated under vacuum. The resulting residue was redissolved in EtOAc and the organic layer was washed with brine, dried over Na$_2$SO$_4$, filtered and concentrated to yield the crude, which was used without further purification.

To a cold (0° C.) solution of the crude from above in 1,4-dioxane (100 mL) was added NH$_3$.H$_2$O (34 mL of 32% aqueous solution). After stirring at rt overnight, the reaction was quenched with water and poured into EtOAc. The organic layer was separated and washed with brine, dried over Na$_2$SO$_4$, filtered and concentrated under reduced pressure to yield the crude product (8.8 g) as a light yellow foam.

Benzoic anhydride (3.6 g, 16.0 mmol) was added to the crude solution from above (8.8 g) in anhydrous DMF (120 mL). After stirring for 16 hrs at rt, the reaction was quenched with saturated sodium bicarbonate and poured into EtOAc. The organic layer was separated and washed with brine, dried over Na$_2$SO$_4$, filtered and concentrated under reduced pressure. Purification by column chromatography (SiO$_2$, eluting with 5-10% ethyl acetate in hexanes) yielded Compound 77 (6.5 g, 71% over 3 steps). LCMS; RT: 6.305 min. MS: m/z=M+23=843.

c) Preparation of Compound 78

Tetrabutylammonium fluoride in THF (9.3 mL of 1.0 M TBAF in THF) was added to a cold (0° C.) solution of Compound 77 (6.3, 7.6 mmol) in THF (70 mL). After stirring for 4 hrs at rt, the reaction was quenched with water and poured into EtOAc. The organic layer was separated and washed with brine, dried over Na$_2$SO$_4$, filtered and concentrated under reduced pressure. Purification by column chromatography (SiO$_2$, eluting with 33% ethyl acetate in hexanes) yielded Compound 78 (4.8 g, 89%). LCMS; RT: 4.842 min. MS: m/z=M+1=706.

d) Preparation of Compound 79

Tetrazole (0.4 g, 5.4 mmol), N-methylimidazole (0.13 mL, 1.7 mmol), 2-cyanoethyltetraisopropyl phosphorodiamidite 3.2 mL, 10.1 mmol) were added to a cold (0° C.) solution of Compound 78 (4.8 g, 6.7 mmol) in anhydrous DMF (35 mL). After stirring for 6 hrs at rt, the reaction was quenched with saturated sodium bicarbonate and poured into EtOAc. The organic layer was separated and washed with brine, dried over Na$_2$SO$_4$, filtered and concentrated under reduced pressure. Purification by column chromatography (SiO$_2$, eluting with 25% ethyl acetate in hexanes) yielded Compound 78 (5.3 g, 81%). $^{31}$P NMR: 149.66, 149.52 ppm. MS: m/z=M+1=906.

Example 23

Preparation of Compound 86

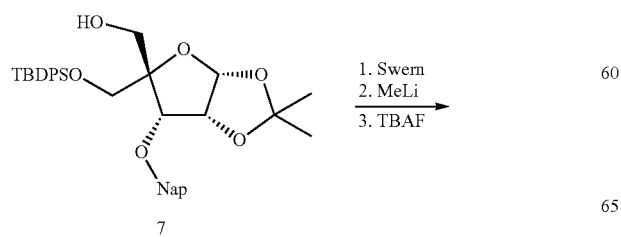

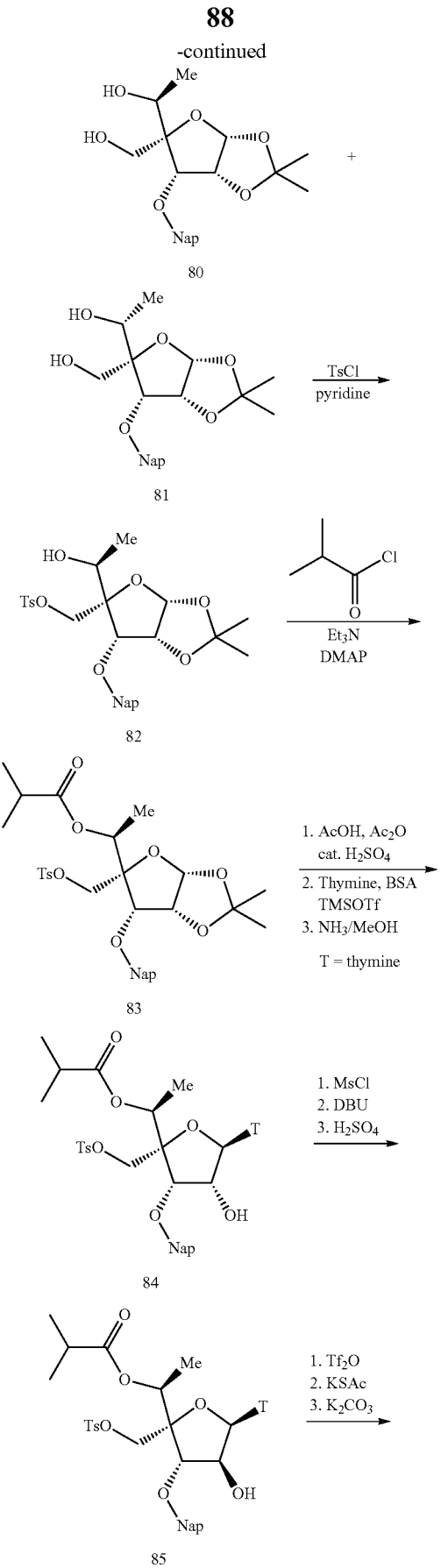

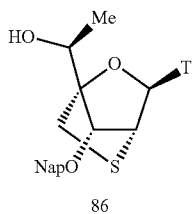

a) Preparation of Compound 80

Compound 7 was prepared as per the procedures illustrated in Example 13. Dimethylsulfoxide (13.5 mL, 189.7 mmol) was added to a cold (−78° C.) solution of oxalyl chloride (8.2 mL, 94.9 mmol) in dichloromethane (200 mL). After stirring for 30 min, a solution of Compound 7 (40.5 g, 67.8 mmol) in dichloromethane (70 mL) was added to the reaction and the stirring was continued for another 45 min. Triethylamine (39.9 mL, 284.6 mmol) was added to the reaction and the cooling bath was removed. After stirring for 30 min, the reaction was sequentially washed with 5% HCl, saturated sodium bicarbonate, brine, dried ($Na_2SO_4$) and concentrated to provide the aldehyde which was used without any further purification.

MeLi (134 mmol, 83.7 mL of a 1.6 M solution in ether) was added to a cold (−78° C.) solution of the aldehyde from above in toluene (500 mL). After stirring for 4 hrs, the reaction was very carefully quenched with methanol and sequentially washed with 5% HCl, saturated sodium bicarbonate, brine, dried ($Na_2SO_4$) and concentrated to provide a mixture of alcohols which was used without any further purification.

Tetrabutylammonium fluoride (75 mL of a 1M solution in THF) was added to a solution of the crude alcohols from above in THF (50 mL). After stirring at rt for 4 hrs, the reaction was diluted with ethyl acetate and the organic layer was washed with water, brine, dried ($Na_2SO_4$) and concentrated. Purification by column chromatography ($SiO_2$, eluting with 5 to 20% acetone in dichloromethane) provided Compound 80 as a major product (16.1 g, 66%) and a mixture of Compounds 80 and 81 (7.0 g, 29%).

b) Preparation of Compound 82 p-Toluenesulfonyl chloride (9.7 g, 50.8 mmol) was added in portions of ~1.5 g per hour over 6 hrs to a cold (0° C.) solution of Compound 80 (15.2 g, 40.7 mmol) in pyridine (80 mL). After the addition of tosyl chloride was complete, the reaction was gradually warmed to room temperature and stirred for 16 hours after which it was quenched with water. The reaction was diluted with ethyl acetate and the organic layer was washed with water, brine, dried ($Na_2SO_4$) and concentrated. Purification by column chromatography ($SiO_2$, eluting with 10-30% ethyl acetate in hexanes) provided Compound 82 (10.4 g, 50%).

c) Preparation of Compound 83

Isobutyryl chloride (4.2 mL, 39.4 mmol) was added to a cold (0° C.) solution of Compound 82 (10.4 g, 19.7 mmol), triethylamine (5.5 mL, 39.4 mmol) and dimethylaminopyridine (0.49 g, 4.0 mmol) in dichloromethane (40 mL). The reaction was allowed to gradually warm to room temperature and left stirring for an additional 16 hrs after being quenched with water. The reaction mixture was diluted with dichloromethane and the organic layer was sequentially washed with 5% HCl, saturated sodium bicarbonate, brine, dried ($Na_2SO_4$) and concentrated. Purification by column chromatography ($SiO_2$, eluting with 20-30% ethyl acetate in hexanes) provided Compound 83 (10.2 g, 89%).

d) Preparation of Compound 85

Sulfuric acid (4 drops) was added to a solution of Compound 83 (6.2 g, 10.3 mmol) in acetic acid (20 mL) and acetic anhydride (5 mL). After stirring at rt for 2 hrs, the solvent was evaporated at room temperature on a rotary evaporator. The resulting residue was redissolved in ethyl acetate and the organic layer was carefully washed with water, saturated sodium bicarbonate (until pH>10), brine, dried ($Na_2SO_4$) and concentrated to provide a mixture of anomeric acetates which were used without any purification.

N,O-Bistrimethylsilyl acetamide (12.7 mL, 51.5 mmol) was added to a suspension of the crude anomeric diacetates from above and thymine (2.6 g, 20.6 mmol) in acetonitrile (50 mL). The reaction was refluxed until complete dissolution occurred after which it was cooled in an ice-bath. TMSOTf (2.8 mL, 15.5 mmol) was added to the reaction and the cooling bath was removed after 5 min. The reaction was then refluxed for 2 hrs after which it was cooled to room temperature and carefully quenched with saturated sodium bicarbonate solution. The reaction was diluted with EtOAc and the organic layer was washed with water, half saturated sodium bicarbonate, brine, dried ($Na_2SO_4$) and concentrated to provide the crude nucleoside which was used without any further purification.

A solution of methanolic ammonia (20 mL of a 7M solution) was added to a cold (0° C.) solution of crude nucleoside (6.5 g) from above in methanol (40 mL). After 5 hrs, additional methanolic ammonia (10 mL) was added to the reaction. After standing for 16 hours, the reaction was concentrated to provide the crude 2'O-deprotected nucleoside Compound 84 which was used without any further purification.

Methanesulfonyl chloride (0.84 mL, 10.8 mmol) was added to a cold (0° C.) solution of the crude nucleoside from above in pyridine (27 mL). The stirring was continued for 5 hrs during which the reaction warmed to room temperature, and quenched with water. The reaction was diluted with ethyl acetate and the organic layer was washed with 5% HCl, saturated sodium bicarbonate, brine ($Na_2SO_4$) and concentrated to provide the crude 2'O-mesyl nucleoside which was used without any further purification.

DBU (2.0 mL, 13.5 mmol) was added to a solution of the crude nucleoside from above in acetonitrile (45 mL). After stirring at rt for 6 hrs, the reaction was diluted with EtOAc and the organic layer was washed with 5% HCl, saturated sodium bicarbonate, brine, dried ($Na_2SO_4$) and concentrated to provide the 2'-anhydro nucleoside which was used without any further purification.

0.25 M sulfuric acid (55 mL) was added to a suspension of the crude 2'-anhydro nucleoside from above in a mixture of methanol (11 mL) and dioxane (44 mL). The reaction was heated at 80° C. for 6 hrs, cooled to room temperature and diluted with ethyl acetate. The organic layer was washed with water, brine, dried ($Na_2SO_4$) and concentrated. Purification by column chromatography (silica gel, eluting with 0-20% acetone in dichloromethane) provided Compound 85 (4.4 g, 65% over 6 steps).

e) Preparation of Compound 86

Triflic anhydride (0.04 mL, 0.22 mmol) was added to a cold (0° C.) solution of Compound 85 (0.1 g, 0.15 mmol) in pyridine (0.8 mL). After the addition was complete, the cooling bath was removed and the solution was stirred at room temperature for 6 hrs and diluted with ethyl acetate. The organic layer was washed with water, brine, dried ($Na_2SO_4$)

and concentrated to provide the 2'-ara-triflate, which was used without any further purification.

Potassium thioacetate (34 mg, 0.3 mmol) was added to a solution of the crude 2'-ara-triflate from above in DMF (0.5 mL). After stirring at rt for 16 hrs, the reaction was diluted with ethyl acetate and the organic layer was washed with water, brine, dried ($Na_2SO_4$) and concentrated to provide the 2'-thioacetyl nucleoside which was used without any further purification.

Potassium carbonate (65 mg, 0.5 mmol) was added to a solution of the crude 2' thioacetyl nucleoside from above in methanol (2 mL). After stirring at rt for 16 hrs, the reaction was diluted with ethyl acetate and the organic layer was washed with water, brine, dried ($Na_2SO_4$) and concentrated. Purification by column chromatography ($SiO_2$, eluting with 10-30% acetone in dichloromethane) provided the 5'-methyl-2'-thio nucleoside Compound 86 (22 mg, 52% over 3 steps).

Example 24

Preparation of Compound 90

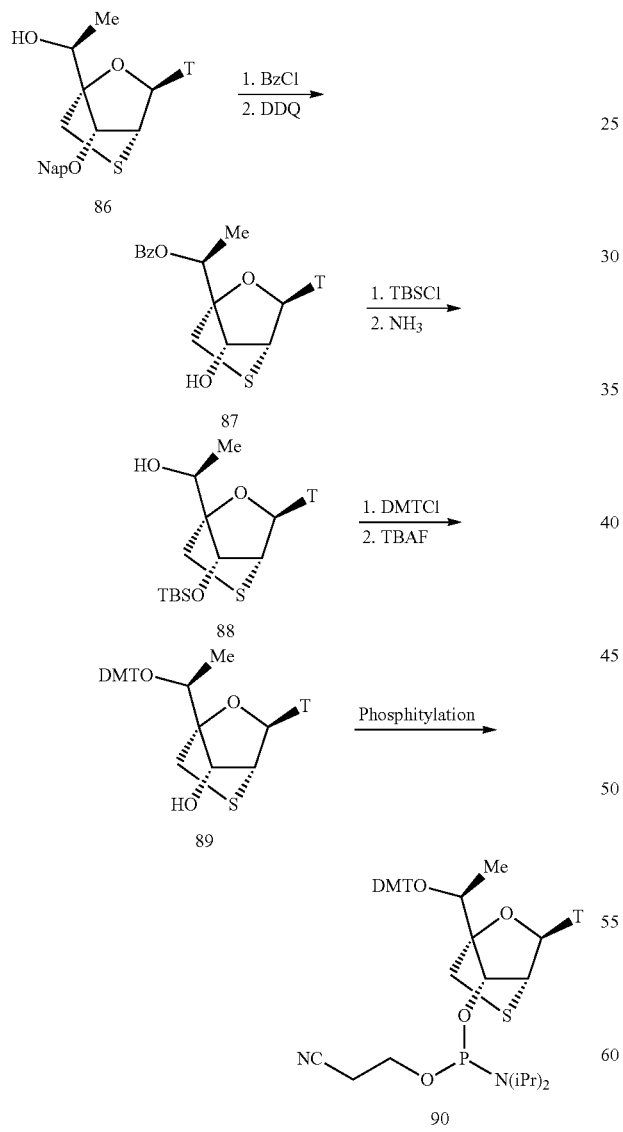

Compound 86 is prepared as per the procedures illustrated in Example 23. The 5'-hydroxyl group in nucleoside Compound 86 is protected as the benzoyl ether using benzoyl chloride in pyridine followed by removal of the 3'-β-naphthyl group with DDQ to provide nucleoside Compound 87. The 3'-hydroxyl group in Compound 87 is protected as tert-butyldimethylsilyl or triethylsilyl ether by reaction with excess silyl chloride and imidazole in DMF followed by removal of the 5'-O-benzoyl group by heating the nucleoside with methanolic ammonia at an elevated temperature (45 to 50° C.) to provide nucleoside Compound 88. The 5'-hydroxyl group is then reacted with excess dimethoxytrityl chloride and 2,6-lutidine in pyridine at an elevated temperature (45 to 50° C.), followed by removal of the 3'-O-silyl protecting group with tetrabutylammonium fluoride to provide nucleoside Compound 89. A phosphitylation reaction then provides the desired phosphoramidite Compound 90.

Example 25

Preparation of Compounds 99 and 100

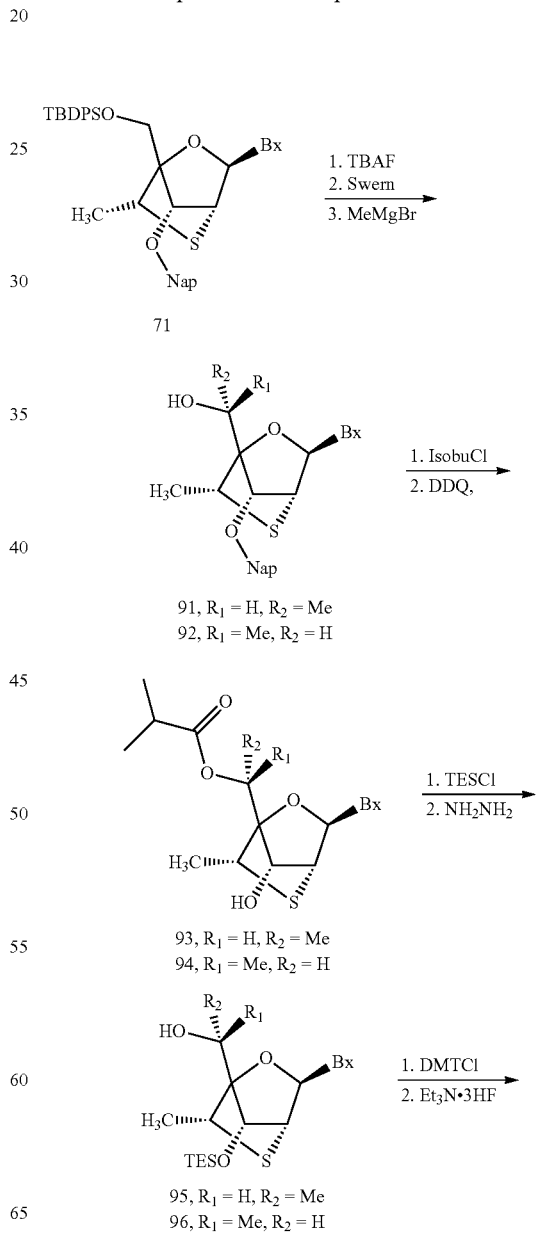

93
-continued

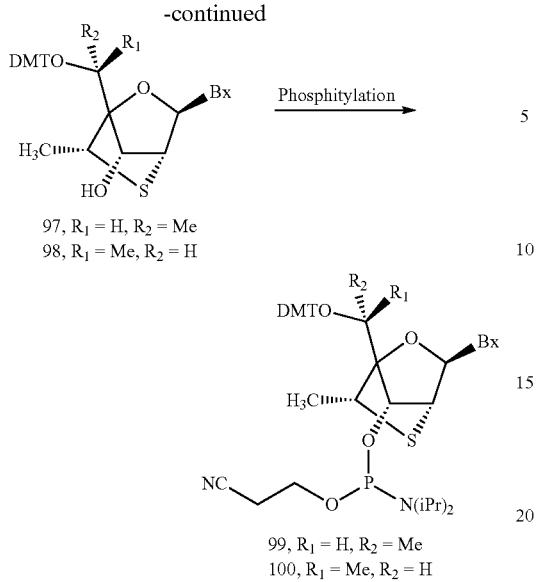

97, R₁ = H, R₂ = Me
98, R₁ = Me, R₂ = H

99, R₁ = H, R₂ = Me
100, R₁ = Me, R₂ = H a) Preparation of Bismethyl 2' Thio Amidite Compound 71 is prepared as per the procedures illustrated in Example 21. The bicyclic thio nucleoside Compound 71 is converted to a bismethyl thio nucleoside by desilylation, oxidation and Grignard reaction to provide a mixture of 5'R and 5'S-Me nucleosides Compounds 91 and 92. The secondary alcohol in Compounds 91 and 92 is protected with isobutryl group followed by removal of the Nap group to provide Compounds 93 and 94, respectively. Protection of the 3'-hydroxyl group followed by removal of the isobutyryl group provides Compounds 95 and 96. The resulting secondary alcohol is protected with DMT group and the TES group is removed with Et₃N.3HF. A phosphitylation reaction provides the desired amidites Compounds 99 and 100.

Example 26

Preparation of Compounds 111a and 111b

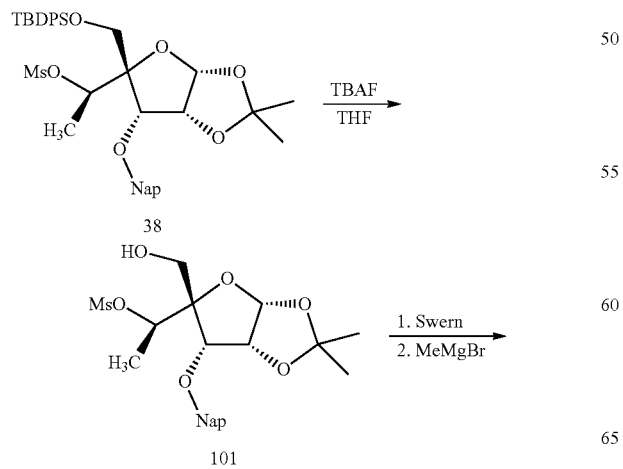

38

101

94
-continued

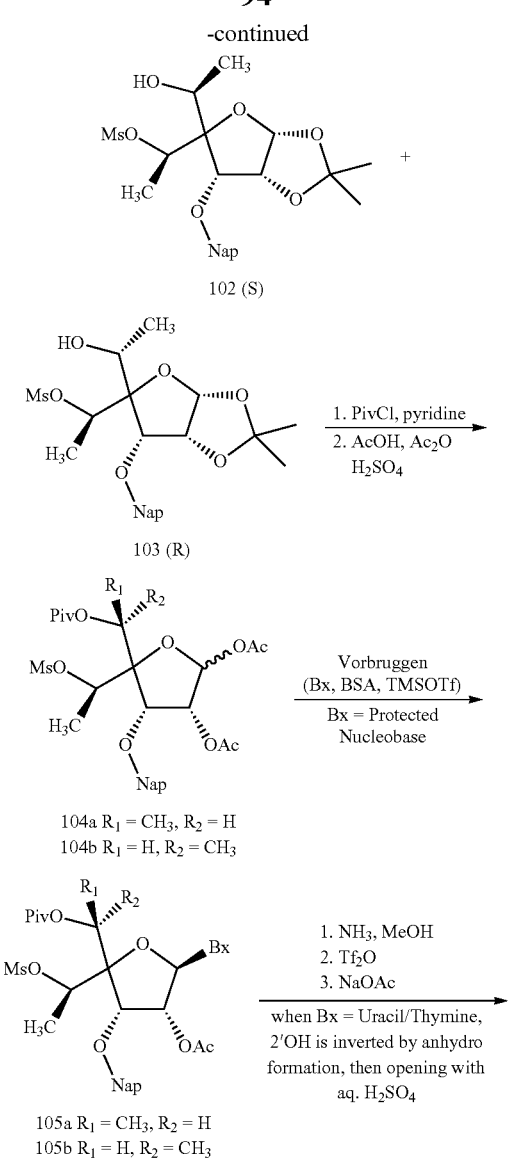

102 (S)

103 (R)

104a R₁ = CH₃, R₂ = H
104b R₁ = H, R₂ = CH₃

105a R₁ = CH₃, R₂ = H
105b R₁ = H, R₂ = CH₃

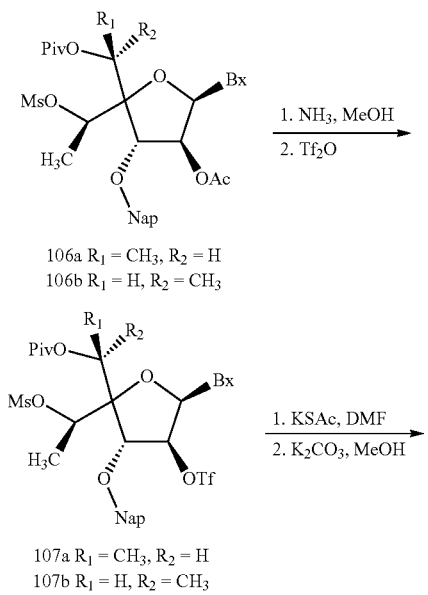

106a R₁ = CH₃, R₂ = H
106b R₁ = H, R₂ = CH₃

107a R₁ = CH₃, R₂ = H
107b R₁ = H, R₂ = CH₃

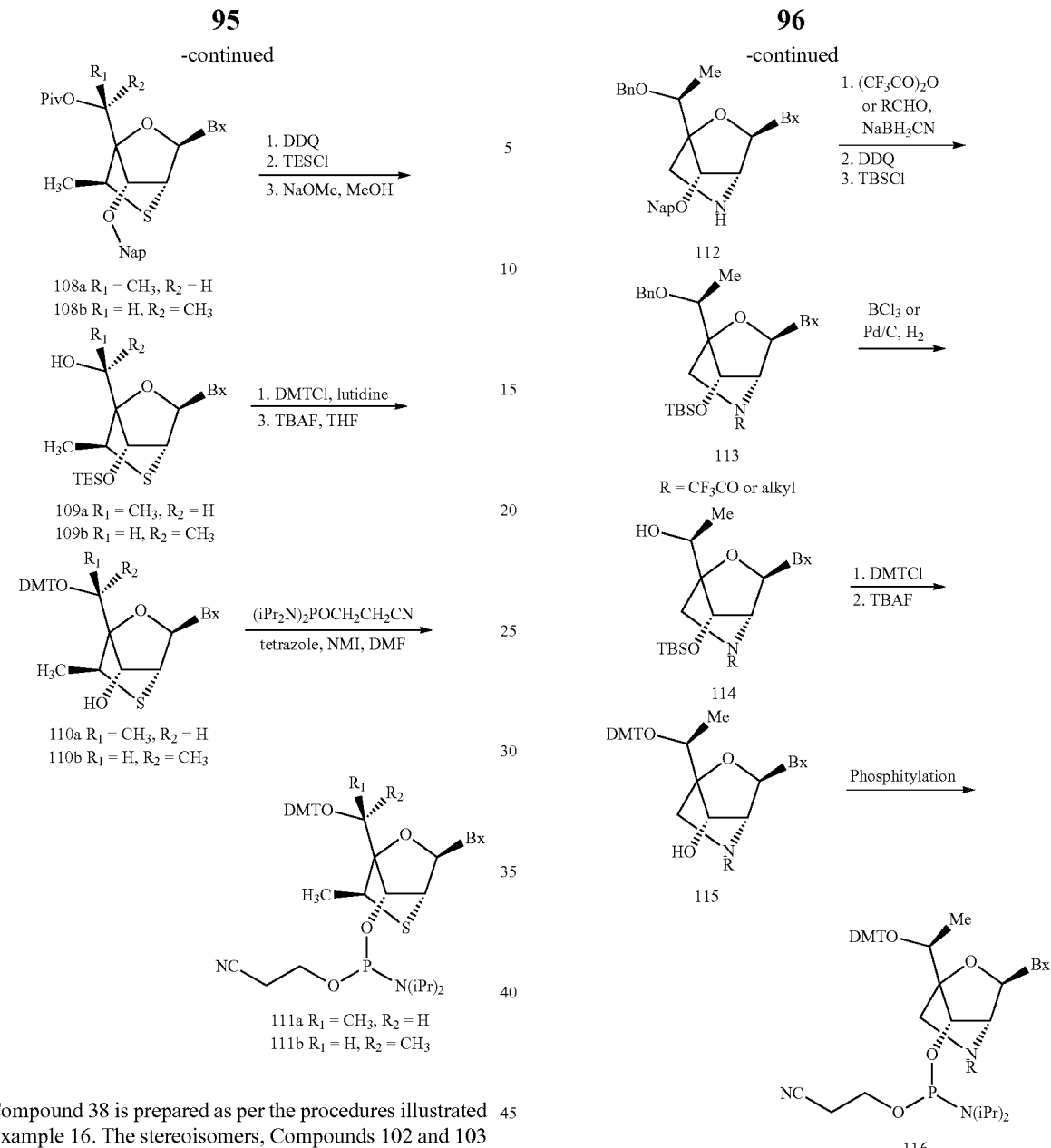
Compound 38 is prepared as per the procedures illustrated in Example 16. The stereoisomers, Compounds 102 and 103 are separated by silica gel column chromatography and each isomer may be carried forward as individual isomers.
Example 27
Preparation of Compound 116
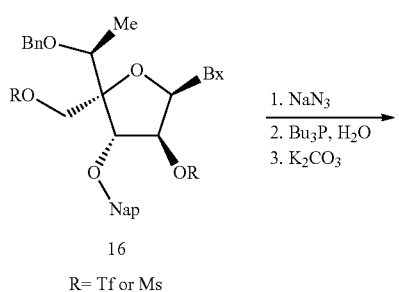
Compound 16 is prepared as per the procedures illustrated in Example 14.
Example 28
Preparation of Compound 121
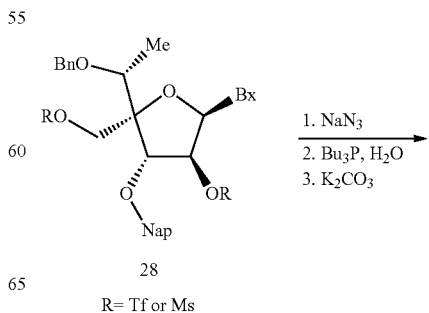

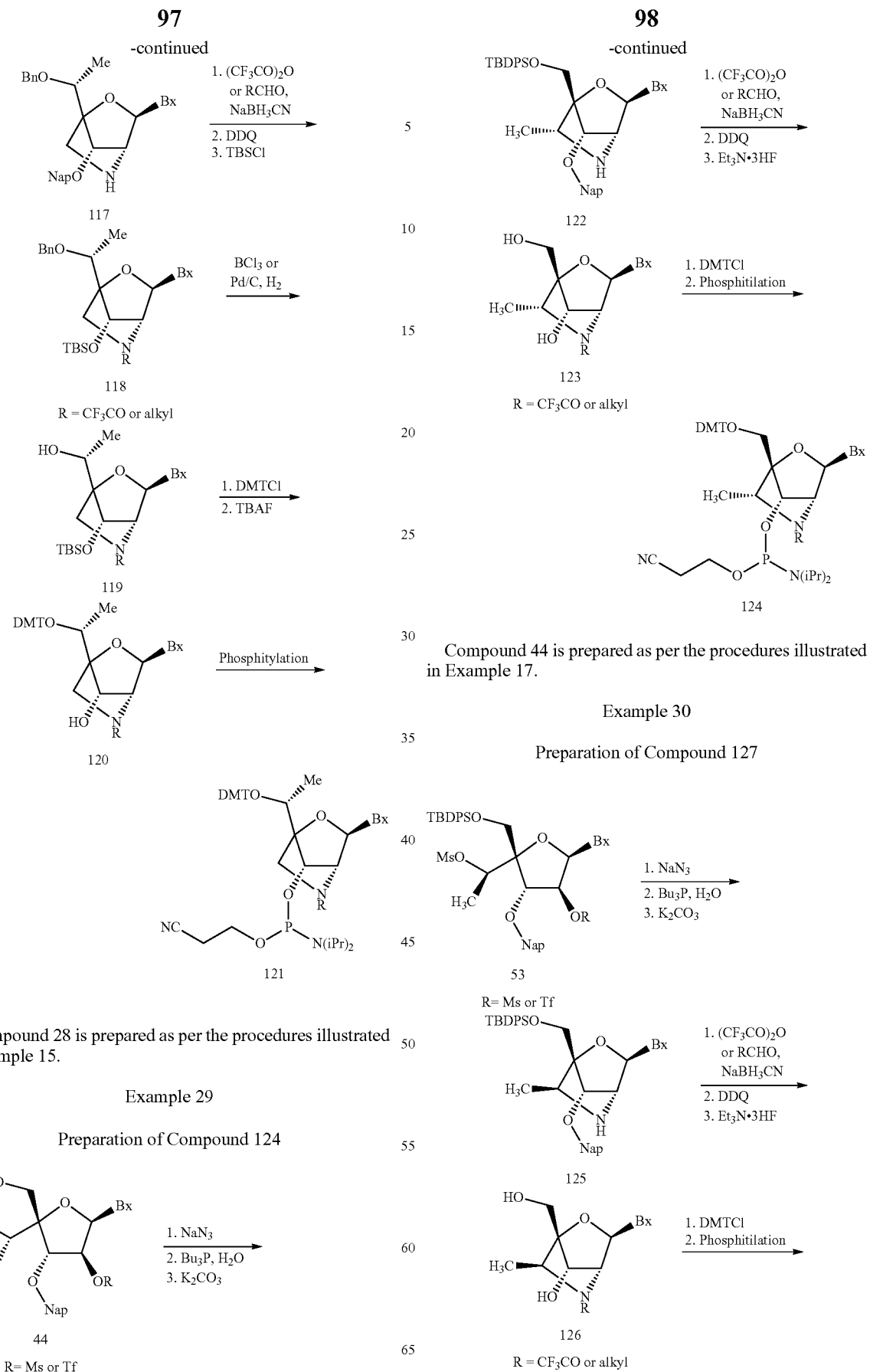

-continued
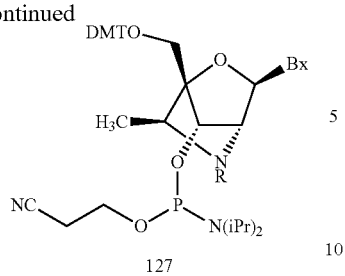
127
Compound 53 is prepared as per the procedures illustrated in Example 18.
Example 31
Preparation of Compound 132
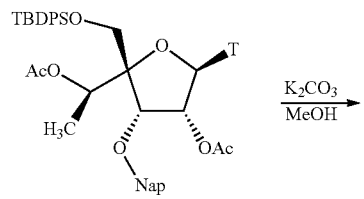
58
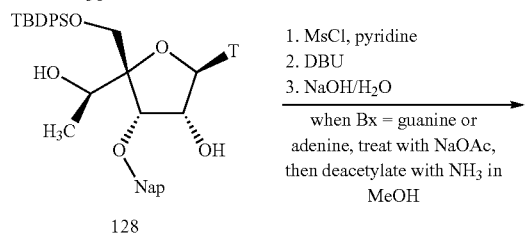
128
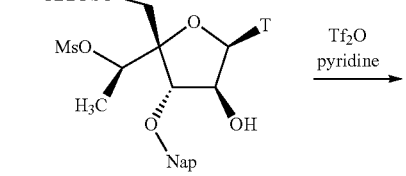
129
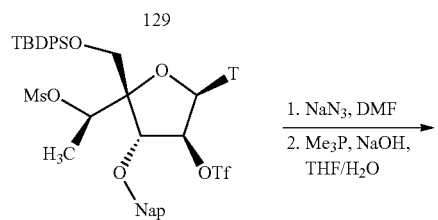
130
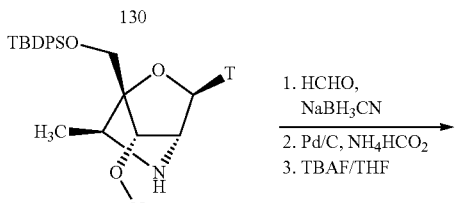
130a
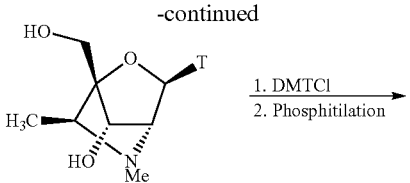
131
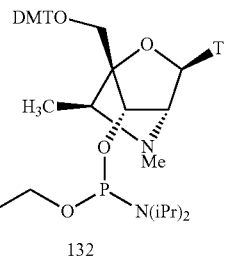
132
Compound 58 was prepared as per the procedures illustrated in Example 19. Structural analysis of Compound 132 was confirmed by $^1$HNMR and mass spectrometry.
Example 32
Preparation of Compound 139
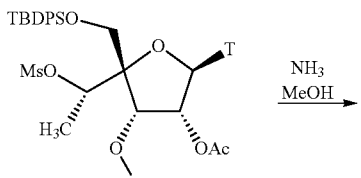
70
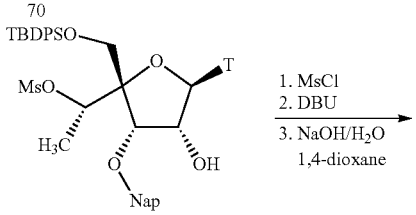
133
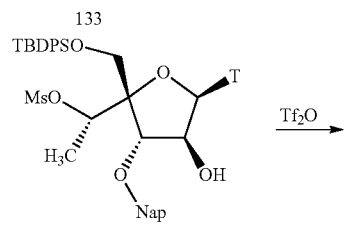
134
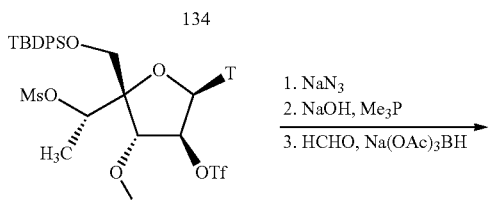
135

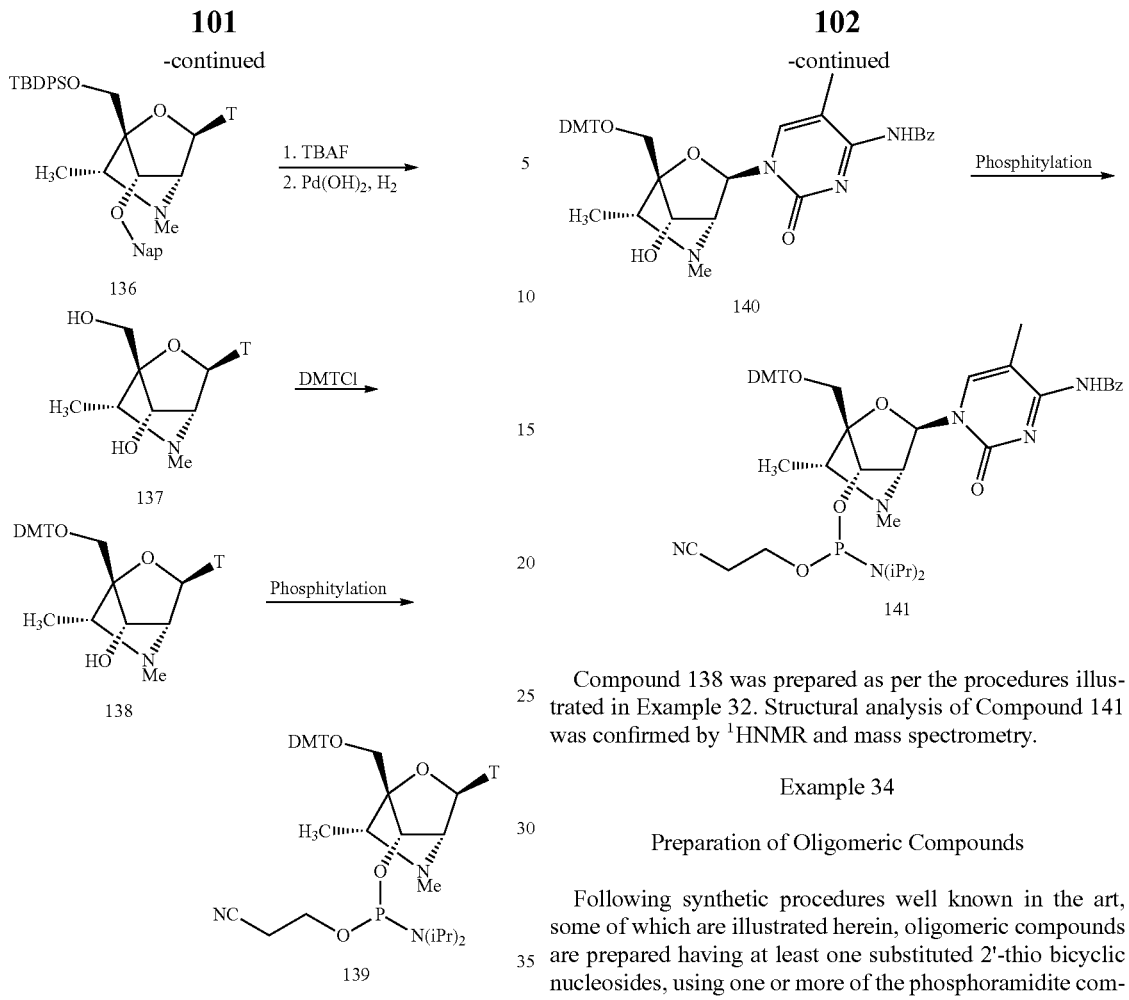

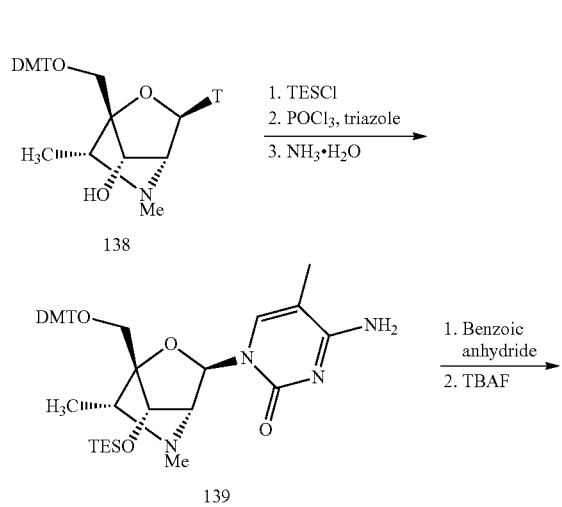

Compound 70 was prepared as per the procedures illustrated in Example 21. Structural analysis of Compound 139 was confirmed by $^1$HNMR and mass spectrometry.

Example 33

Preparation of Compound 141

Compound 138 was prepared as per the procedures illustrated in Example 32. Structural analysis of Compound 141 was confirmed by $^1$HNMR and mass spectrometry.

Example 34

Preparation of Oligomeric Compounds

Following synthetic procedures well known in the art, some of which are illustrated herein, oligomeric compounds are prepared having at least one substituted 2'-thio bicyclic nucleosides, using one or more of the phosphoramidite compounds illustrated in the Examples such as DMT phosphoramidites (see Compound 21, Example 14; Compound 33, Example 15; Compound 47, Example 17; Compound 56; Example 18; Compound 65, Example 19; Compound 69; Example 20; Compound 75; Example 21; Compound 79; Example 22; Compound 90, Example 24; Compounds 99 and 100, Example 25; Compounds 111a and 111b, Example 26; Compound 116, Example 27; Compound 121, Example 28; Compound 124, Example 29; Compound 127, Example 30; Compounds 132, 139 and 141, Examples 31-33).

Example 35

Preparation of Gapped Oligomeric Compounds for Tm Studies

The gapped oligomeric compounds comprising at least one or more bicycic nucleosides were prepared and the $T_m$'s were assessed as illustrated herein. A Cary 100 Bio spectrophotometer with the Cary Win UV Thermal program was used to measure absorbance vs. temperature. For the $T_m$ experiments, oligonucleotides were prepared at a concentration of 8 μM in a buffer of 100 mM Na+, 10 mM phosphate, 0.1 mM EDTA, pH 7. Concentration of oligonucleotides were determined at 85° C. The oligonucleotide concentration was 4 μM with mixing of equal volumes of test oligonucleotide and match or mismatch RNA strand. Oligonucleotides were hybridized with the complimentary or mismatch RNA strand by heating duplex to 90° C. for 5 min and allowed to cool at room temperature. Using the spectrophotometer, $T_m$ measurements were taken by heating duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. Presented below is the $T_m$ for the gapped oligomeric compounds when duplexed to RNA complement (SEQ ID NO: 07/ISIS NO. 419890).

| SEQ ID NO./ ISIS NO. | Sequence (5' to 3') | $T_m$ (° C.) | Chemistry |
|---|---|---|---|
| 05/484899 | $^{Me}C_{SS}T_{SS}$TAGCACTGGC$^{Me}C_{SS}T_{SS}$ | 63.5 | 2'-S-(S)-cEt |
| 05/484900 | $^{Me}C_{SR}T_{SR}$TAGCACTGGC$^{Me}C_{SR}T_{SR}$ | 65.1 | 2'-S-(R)-cEt |
| 05/411847 | $^{Me}C_{S}T_{S}$TAGCACTGGC$^{Me}C_{S}T_{S}$ | 64.2 | (S)-cEt |
| 05/485159 | $^{Me}C_{A}T_{A}$TAGCACTGGC$^{Me}C_{A}T_{A}$ | 59.8 | Methylamino LNA |
| 05/485160 | $^{Me}C_{AS}T_{AS}$TAGCACTGGC$^{Me}C_{AS}T_{AS}$ | 58.1 | Methylamino (S)-cEt |
| 05/485161 | $^{Me}C_{AR}T_{AR}$TAGCACTGGC$^{Me}C_{AR}T_{AR}$ | 57.6 | Methylamino (R)-cEt |
| 07/419890 | *UCAAGGCCAGUGCUAAGAGU* | | |

Each internucleoside linkage is a phosphorothioate. Nucleosides not followed by a subscript are β-D-2'-deoxyribonucleosides and italicized nucleosides are (3-D-ribonucleosides. Superscript "Me" indicates a 5-methyl group on the pyrimidine base of the nucleoside. Nucleosides followed by a subscript are modified nucleosides listed below (Example 38).

It can be seen that an improvement in binding affinity as shown by Tm is seen with oligonucleotides incorporating the 2'-S—(S)-cEt and 2'-S—(R)-cEt bicyclic nucleosides.

Example 36

2'-S—(S)-cEt BNA and (S)-cEt BNA 2-10-2 Gapped Oligomeric Compounds Targeted to PTEN or SRB-1: In Vitro Dose Response Study A series of gapped oligomeric compounds were prepared and tested for their ability to reduce PTEN or SRB-1 mRNA expression over a range of doses in C2C12 cells. C2C12 cells were treated with 2'-S—(S)-cEt BNA or (S)-cEt BNA gapped oligomeric compounds at concentrations of 100, 200 or 300 nM. Transfection was performed using Lipofectin and RNA was extracted and analyzed using methods described herein. PTEN or SRB-1 mRNA expression levels were quantitated using real-time PCR and normalized to RIBOGREEN as described herein. The results are listed below as PTEN or SRB-1 mRNA expression relative to untreated control cells (% UTC).

| SEQ ID NO./ ISIS NO. | Target | Composition (5' to 3') | Chemistry |
|---|---|---|---|
| 05/411847 | PTEN | $^{Me}C_{S}T_{S}$TAGCACTGGC$^{Me}C_{S}T_{S}$ | (S)-cEt |
| 05/484899 | PTEN | $^{Me}C_{SS}T_{SS}$TAGCACTGGC$^{Me}C_{SS}T_{SS}$ | 2'-S-(S)-cEt |
| 06/440761 | SRB-1 | $T_{S}{}^{Me}C_{S}$AGTCATGACTT$_{S}{}^{Me}C_{S}$ | (S)-cEt |
| 06/484902 | SRB-1 | $T_{SS}{}^{Me}C_{SS}$AGTCATGACTT$_{SS}{}^{Me}C_{SS}$ | 2'-S-(S)-cEt |

Each internucleoside linkage is a phosphorothioate. Nucleosides not followed by a subscript are β-D-2'-deoxyribonucleosides. Superscript "Me" indicates a 5-methyl group on the pyrimidine base of the nucleoside. Nucleosides followed by a subscript are modified nucleosides listed below.

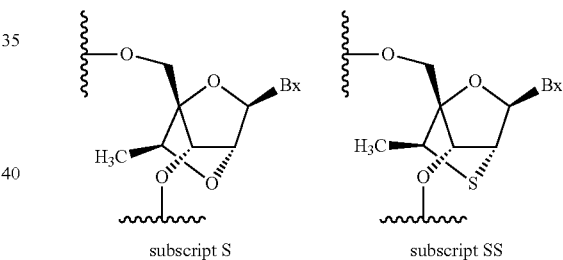

subscript S            subscript SS

| SEQ ID NO./ ISIS NO. | Dose (nM) | % UTC | Chemistry | Target |
|---|---|---|---|---|
| Saline | 0 | 100 | | |
| 05/411847 | 300 | 17.2 | (S)-cEt | PTEN |
| 05/411847 | 200 | 22.2 | | |
| 05/411847 | 100 | 30.9 | | |
| 05/484899 | 300 | 29.5 | 2'-S—(S)-cEt | |
| 05/484899 | 200 | 26.8 | | |
| 05/484899 | 100 | 38.0 | | |
| 06/440761 | 300 | 11.0 | (S)-cEt | SRB-1 |
| 06/440761 | 200 | 15.4 | | |
| 06/440761 | 100 | 25.7 | | |
| 06/484902 | 300 | 36.6 | 2'-S—(S)-cEt | |
| 06/484902 | 200 | 29.6 | | |
| 06/484902 | 100 | 58.3 | | |

Example 37

2-10-2 Gapped Oligomeric Compounds Targeting PTEN or SRB-1 in Varied Muscle Types: in vivo Study Six week old BALB/C mice (Jackson Laboratory, Bar Harbor, Me.) were injected subcutaneously twice a week at dosage 25 mg/kg (50 mg total) for three weeks with gapped oligomeric compounds targeted to PTEN or SRB-1 or with saline control. The mice were sacrificed 48 hrs following last administration. Various tissues including liver, quadriceps (Quad), gastrocnemius (Gastro), heart, and diaphragm (Diaph) were homogenized and mRNA levels were quantitated using real-time PCR as described herein for comparison to untreated control levels (% UTC). The results are listed as the average % of PTEN or SRB-1 mRNA expression in different muscle types for each treatment group relative to saline-injected control. Additional analysis that were performed in such in vivo studies included plasma chemistries, liver, spleen and kidney weights, from animals treated with gapped oligomeric compounds. Liver transaminase levels, alanine aminotranferase (ALT) and aspartate aminotransferase (AST), in serum were also measured relative to saline injected mice and the results are presented below.

| (% UTC) mRNA expression in varied muscle types | | | | | | |
| --- | --- | --- | --- | --- | --- | --- |
| SEQ ID NO./ ISIS NO. | Target | Liver | Quad | Gastro | Heart | Diaph |
| 05/411847 | PTEN | 5.3 | 70.0 | 59.6 | 90.5 | 43.9 |
| 05/484899 | PTEN | 6.1 | 55.9 | 47.9 | 82.5 | 60.9 |
| 06/440761 | SRB-1 | 3.5 | 15.6 | 36.3 | 36.3 | 14.2 |
| 06/484902 | SRB-1 | 3.0 | 23.9 | 40.8 | 38.4 | 13.8 |
| Saline | % UTC = 100 | | | | | |

| (% UTC) mRNA expression in varied muscle types | | | | |
| --- | --- | --- | --- | --- |
| SEQ ID NO./ ISIS NO. | Target | ALT (IU/L) | AST (IU/L) | Chemistry |
| 05/411847 | PTEN | 171.3 | 145.5 | (S)-cEt |
| 05/484899 | PTEN | 25.5 | 53.3 | 2'-S-(S)-cEt |
| 06/440761 | SRB-1 | 71.8 | 158.5 | (S)-cEt |
| 06/484902 | SRB-1 | 54.8 | 108.8 | 2'-S-(S)-cEt |
| Saline | | 31.8 | 128.5 | |

The liver, spleen and kidney weights were within normal limits for animals treated with gapped oligomeric compounds relative to saline-treated control. In certain embodiments, the oligomeric compounds comprising 2'-S—(S)-cEt modified nucleosides in the wings (484899, 484902) provided good activity in conjunction with low toxicity.

Example 38

2-10-2 Gapmers Targeting PTEN or SRB-1: in vivo dose response study

Six week old Balb/c mice (Jackson Laboratory, Bar Harbor, Me.) were injected twice per week for three weeks with the 2-10-2 gapped oligomeric compounds shown below targeted to either PTEN or SRB-1. Doses listed are per each injection. The mice were sacrificed 48 hours following last administration. Liver tissues were homogenized and mRNA levels were quantitated using real-time PCR as described herein for comparison to untreated control levels (% UTC). Plasma chemistry analysis was completed. The results are listed below as the average % of PTEN and SRB-1 mRNA expression for each treatment group relative to saline-injected control. Liver transaminase levels, alanine aminotranferase (ALT) in serum were also measured relative to saline injected mice are listed below.

| SEQ. ID NO./ ISIS NO. | Target | Composition (5' to 3') | Chemistry |
| --- | --- | --- | --- |
| 05/484899 | PTEN | $^{Me}C_{SS}T_{SS}$TAGCACTGGC$^{Me}C_{SS}T_{SS}$ | 2'-S-(S)-cEt |
| 05/484900 | PTEN | $^{Me}C_{SR}T_{SR}$TAGCACTGGC$^{Me}C_{SR}T_{SR}$ | 2'-S-(R)-cEt |
| 05/411847 | PTEN | $^{Me}C_{S}T_{S}$TAGCACTGGC$^{Me}C_{S}T_{S}$ | (S)-cEt |
| 05/485159 | PTEN | $^{Me}C_{A}T_{A}$TAGCACTGGC$^{Me}C_{A}T_{A}$ | Methylamino LNA |
| 05/485160 | PTEN | $^{Me}C_{AS}T_{AS}$TAGCACTGGC$^{Me}C_{AS}T_{AS}$ | Methylamino (S)-cEt |
| 05/485161 | PTEN | $^{Me}C_{AR}T_{AR}$TAGCACTGGC$^{Me}C_{AR}T_{AR}$ | Methylamino (R)-cEt |
| 06/484902 | SRB-1 | $T_{SS}{}^{Me}C_{SS}$AGTCATGACTT$_{SS}{}^{Me}C_{SS}$ | 2'-S-(S)-cEt |
| 06/484903 | SRB-1 | $T_{SR}{}^{Me}C_{SR}$AGTCATGACTT$_{SR}{}^{Me}C_{SR}$ | 2'-S-(R)-cEt |
| 06/440761 | SRB-1 | $T_{S}{}^{Me}C_{S}$AGTCATGACTT$_{S}{}^{Me}C_{S}$ | (S)-cEt |
| 06/485162 | SRB-1 | $T_{A}{}^{Me}C_{A}$AGTCATGACTTA$^{Me}C_{A}$ | Amino LNA |
| 06/485163 | SRB-1 | $T_{AS}{}^{Me}C_{AS}$AGTCATGACTT$_{AS}{}^{Me}C_{AS}$ | Methylamino (S)-cEt |
| 06/485164 | SRB-1 | $T_{AR}{}^{Me}C_{AR}$AGTCATGACTT$_{AR}{}^{Me}C_{AR}$ | Methylamino (R)-cEt |

Each internucleoside linkage is a phosphorothioate. Nucleosides not followed by a subscript are β-D-2'-deoxyribonucleosides. Superscript "Me" indicates a 5-methyl group on the pyrimidine base of the nucleoside. Nucleosides followed by a subscript are modified nucleosides listed below.

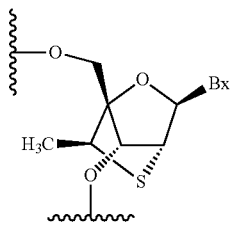
subscript SS

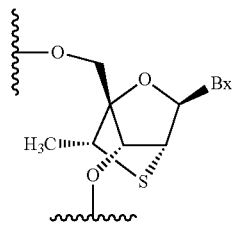
subscript SR

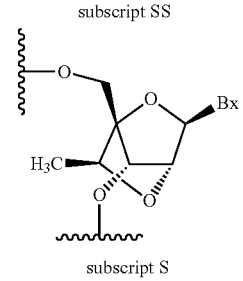
subscript S

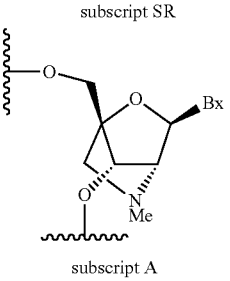
subscript A

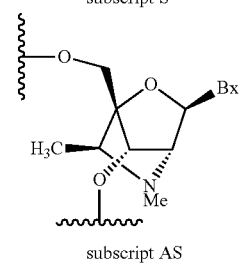
subscript AS

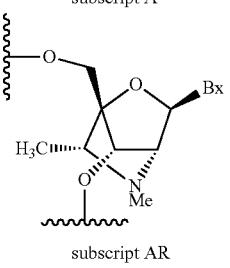
subscript AR

| | | Liver mRNA | | |
|---|---|---|---|---|
| SEQ. ID NO./ ISIS NO. | Dose (mg/kg) | PTEN (% UTC) | ALT (IU/L) | Chemistry |
| Saline | 0 | 100 | 16 | |
| 05/484899 | 25 | 14.6 | 24 | 2'-S—(S)-cEt |

| | | Liver mRNA | | |
|---|---|---|---|---|
| SEQ. ID NO./ ISIS NO. | Dose (mg/kg) | PTEN (% UTC) | ALT (IU/L) | Chemistry |
| 05/484899 | 7.9 | 39.6 | 26 | |
| 05/484899 | 2.5 | 78.1 | 19 | |
| 05/484900 | 25 | 30.5 | 37 | 2'-S—(R)-cEt |
| 05/484900 | 7.9 | 54.6 | 32 | |
| 05/484900 | 2.5 | 92.1 | 23 | |
| 05/411847 | 25 | 7.9 | | (S)-cEt |
| 05/411847 | 2.5 | 67.5 | | |
| 05/485159 | 25 | 46.4 | | Methylamino LNA |
| 05/485159 | 7.9 | 66.2 | | |
| 05/485159 | 2.5 | 90.0 | | |
| 05/485160 | 25 | 64.8 | | Methylamino (S)-cEt |
| 05/485160 | 7.9 | 84.2 | | |
| 05/485160 | 2.5 | 81.2 | | |
| 05/485161 | 25 | 53.5 | | Methylamino (R)-cEt |
| 05/485161 | 7.9 | 101 | | |
| 05/485161 | 2.5 | 110 | | |

| | | Liver mRNA | | |
|---|---|---|---|---|
| SEQ. ID NO./ ISIS NO. | Dose (mg/kg) | SRB-1 (% UTC) | ALT (IU/L) | Chemistry |
| Saline | 0 | 100 | | |
| 06/484902 | 25 | 4.7 | 33 | 2'-S—(S)-cEt |
| 06/484902 | 5.0 | 7.9 | 32 | |
| 06/484902 | 1.0 | 54.7 | 63 | |
| 06/484903 | 25 | 5.0 | 47 | 2'-S—(R)-cEt |
| 06/484903 | 5.0 | 26.8 | 37 | |
| 06/484903 | 1.0 | 68.5 | 27 | |
| 06/440761 | 25 | 3.4 | | (S)-cEt |
| 06/440761 | 1 | 14.9 | | |
| 06/485162 | 25 | 9.2 | | Methylamino LNA |
| 06/485162 | 5 | 51.5 | | |
| 06/485162 | 1 | 83.9 | | |
| 06/485163 | 25 | 10.5 | | Methylamino (S)-cEt |
| 06/485163 | 5 | 66.5 | | |
| 06/485163 | 1 | 98.5 | | |
| 06/485164 | 25 | 30.8 | | Methylamino (R)-cEt |
| 06/485164 | 5 | 79.1 | | |
| 06/485164 | 1 | 102.5. | | |

What is claimed is:

1. A bicyclic nucleoside having Formula I:

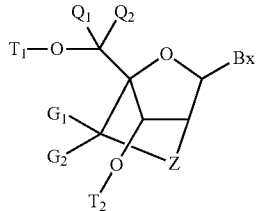

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
Z is S or NR;
R is H, $C_1$-$C_6$ alkyl, substituted $C_1$-$C_6$ alkyl or substituted acyl;
each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein at least one of $Q_1$, $Q_2$, $G_1$ and $G_2$ is other than H.

2. The bicyclic nucleoside of claim 1 wherein Bx is an optionally protected uracil, thymine, cytosine, 5-methylcytosine, adenine or guanine.

3. The bicyclic nucleoside of claim 1 wherein $T_1$ is 4,4'-dimethoxytrityl and $T_2$ is diisopropylcyanoethoxy phosphoramidite.

4. The bicyclic nucleoside of claim 1 wherein $Q_1$ and $Q_2$ are each H.

5. The bicyclic nucleoside of claim 1 wherein one of $Q_1$ and $Q_2$ is H and the other of $Q_1$ and $Q_2$ is $C_1$-$C_6$ alkyl or substituted $C_1$-$C_6$ alkyl.

6. The bicyclic nucleoside of claim 1 wherein one of $Q_1$ and $Q_2$ is $CH_3$.

7. The bicyclic nucleoside of claim 1 wherein $G_1$ and $G_2$ are each H.

8. The bicyclic nucleoside of claim 1 wherein one of $G_1$ and $G_2$ is H and the other of $G_1$ and $G_2$ is $C_1$-$C_6$ alkyl or substituted $C_1$-$C_6$ alky.

9. The bicyclic nucleoside of claim 1 wherein at least one of $G_1$ and $G_2$ is $CH_3$.

10. The bicycle nucleoside of claim 1 wherein Z is NR wherein R is H or $C_1$-$C_6$ alkyl.

11. The bicyclic nucleoside of claim 10 wherein R is $CH_3$.

12. The bicyclic nucleoside of claim 1 wherein Z is S.

13. The bicyclic nucleoside of claim 1 having Formula Ia:

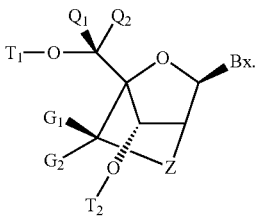

14. The bicyclic nucleoside of claim 13 wherein three of $Q_1$, $Q_2$, $G_1$ and $G_2$ are H and the other one of $Q_1$, $Q_2$, $G_1$ and $G_2$ is $CH_3$.

15. The bicyclic nucleoside of claim 13 wherein two of $Q_1$, $Q_2$, $G_1$ and $G_2$ are H and the remaining two of $Q_1$, $Q_2$, $G_1$ and $G_2$ are $CH_3$ wherein the two that are $CH_3$ are selected from $Q_1$ and $G_1$, $Q_1$ and $G_2$, $Q_2$ and $G_1$, and $Q_2$ and $G_2$.

16. An oligomeric compound comprising at least one bicyclic nucleoside of Formula II:

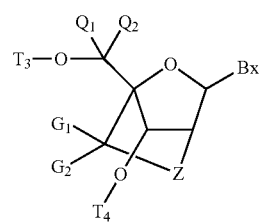

wherein independently for each bicyclic nucleoside of Formula II:
Bx is a heterocyclic base moiety;
one of $T_3$ and $T_4$ is an internucleoside linking group linking the bicyclic nucleoside to the oligomeric compound and the other of $T_3$ and $T_4$ is H, a hydroxyl protecting group, a 5' or 3'-terminal group or an internucleoside linking group linking the bicyclic nucleoside to the oligomeric compound;
$Q_1$ and $Q_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ and $G_2$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
Z is S or NR;
R is H, $C_1$-$C_6$ alkyl, substituted $C_1$-$C_6$ alkyl or substituted acyl;
each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group; and
wherein at least one of $Q_1$, $Q_2$, $G_1$ and $G_2$ is other than H.

17. The oligomeric compound of claim 16 wherein Bx is an optionally protected uracil, thymine, cytosine, 5-methylcytosine, adenine or guanine for each bicyclic nucleoside of Formula II.

18. The oligomeric compound of claim 16 wherein at least one of $T_3$ and $T_4$ is a 5' or 3'-terminal group.

19. The oligomeric compound of claim 16 wherein $Q_1$ and $Q_2$ are each H for each bicyclic nucleoside of Formula II.

20. The oligomeric compound of claim 16 wherein one of $Q_1$ and $Q_2$ is H and the other of $Q_1$ and $Q_2$ is $C_1$-$C_6$ alkyl or substituted $C_1$-$C_6$ alkyl for each bicyclic nucleoside of Formula II.

21. The oligomeric compound of claim 20 wherein one of $Q_1$ and $Q_2$ is $CH_3$ for each bicyclic nucleoside of Formula II.

22. The oligomeric compound of claim 16 wherein $G_1$ and $G_2$ are each H for each bicyclic nucleoside of Formula II.

23. The oligomeric compound of claim 16 wherein one of $G_1$ and $G_2$ is H and the other of $G_1$ and $G_2$ is $C_1$-$C_6$ alkyl or substituted $C_1$-$C_6$ alkyl for each bicyclic nucleoside of Formula II.

24. The oligomeric compound of claim 23 wherein one of $G_1$ and $G_2$ is $CH_3$ for each bicyclic nucleoside of Formula II.

25. The oligomeric compound of claim 16 wherein Z is NR and wherein R is H or $C_1$-$C_6$ alkyl for each bicyclic nucleoside of Formula II.

26. The oligomeric compound of claim 25 wherein R is $CH_3$ for each bicycle nucleoside of Formula II.

27. The oligomeric compound of claim 16 wherein each bicyclic nucleoside has Formula IIa:

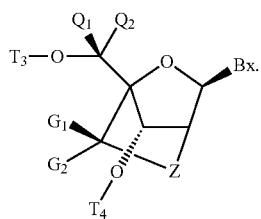

28. The oligomeric compound of claim 27 wherein three of $Q_1$, $Q_2$, $G_1$ and $G_2$ are H and the other one of $Q_1$, $Q_2$, $G_1$ and $G_2$ is $CH_3$ for each bicyclic nucleoside of Formula IIa.

29. The oligomeric compound of claim 27 wherein two of $Q_1$, $Q_2$, $G_1$ and $G_2$ are H and the remaining two of $Q_1$, $Q_2$, $G_1$ and $G_2$ are $CH_3$ wherein the two that are $CH_3$ are selected from $Q_1$ and $G_1$, $Q_1$ and $G_2$, $Q_2$ and $G_1$, $Q_2$ and $G_2$ for each bicyclic nucleoside of Formula IIa.

30. The oligomeric compound of claim 16 comprising at least two regions wherein each region independently comprises from 1 to about 5 contiguous bicyclic nucleosides of Formula II and wherein the two regions are separated by an internal region comprising at least one monomer subunit different from bicycle nucleosides having Formula II and independently selected from nucleosides and modified nucleosides.

31. The oligomeric compound of claim 30 comprising a gapped oligomeric compound wherein one region of contiguous bicyclic nucleosides of Formula II is located at the 5'-end and a second region of contiguous bicyclic nucleosides of Formula II is located at the 3'-end, wherein the two regions are separated by an internal region comprising from about 6 to about 18 monomer subunits different from bicycle nucleosides having Formula II and independently selected from nucleosides and modified nucleosides.

32. The oligomeric compound of claim 16 wherein each inter-nucleoside linking group is, independently, a phosphodiester internucleoside linking group or a phosphorothioate internucleoside linking group.

33. The oligomeric compound of claim 16 wherein essentially each internucleoside linking group is a phosphorothioate internucleoside linking group.

34. A method comprising contacting a cell with an oligomeric compound of claim 16 wherein said oligomeric compound is complementary to a target RNA.

35. The method of claim 34 wherein said cell is in an animal.

36. The method of claim 34 wherein said cell is in a human.

* * * * *

SEQUENCE LISTING

<160> NUMBER OF SEQ ID NOS: 7

<210> SEQ ID NO 1
<211> LENGTH: 3160
<212> TYPE: DNA
<213> ORGANISM: Homo sapiens
<220> FEATURE:
<221> NAME/KEY: CDS
<222> LOCATION: (1035)...(2246)

<400> SEQUENCE: 1

```
cctcccctcg cccggcgcgg tcccgtccgc ctctcgctcg cctcccgcct ccccctcggtc    60 ttccgaggcg cccgggctcc cggcgcggcg gcggaggggg cgggcaggcc ggcgggcggt   120
gatgtggcag gactctttat gcgctgcggc aggatacgcg ctcggcgctg ggacgcgact   180
gcgctcagtt ctctcctctc ggaagctgca gccatgatgg aagtttgaga gttgagccgc   240
```

```
tgtgaggcga ggccgggctc aggcgaggga gatgagagac ggcggcggcc gcggccggga      300 gccctctca gcgcctgtga gcagccgcgg gggcagcgcc ctcggggagc cggccggcct       360
gcggcggcgg cagcggcggc gtttctcgcc tcctcttcgt cttttctaac cgtgcagcct      420
cttcctcggc ttctcctgaa agggaaggtg aagccgtgg gctcgggcgg gagccggctg      480
aggcgcggcg gcggcggcgg cggcacctcc cgctcctgga gcgggggga gaagcggcgg     540 cggcggcggc cgcggcggct gcagctccag ggaggggtc tgagtcgcct gtcaccattt      600
ccagggctgg gaacgccgga gagttggtct ctccccttct actgcctcca acacggcggc      660
ggcggcggcg gcacatccag ggacccgggc cggttttaaa cctcccgtcc gccgccgccg      720 cacccccgt ggcccgggct ccggaggccg ccggcggagg cagccgttcg gaggattatt      780
cgtcttctcc ccattccgct gccgccgctg ccaggcctct ggctgctgag agaagcagg      840 cccagtcgct gcaaccatcc agcagccgcc gcagcagcca ttaccggct gcggtccaga      900 gccaagcggc ggcagagcga ggggcatcag ctaccgccaa gtccagagcc atttccatcc      960
tgcagaagaa gccccgccac cagcagcttc tgccatctct ctcctccttt ttcttcagcc     1020
```

| | | | | | | | | | | | | | | | | |
|---|---|---|---|---|---|---|---|---|---|---|---|---|---|---|---|---|
| acaggctccc agac | atg | aca | gcc | atc | atc | aaa | gag | atc | gtt | agc | aga | aac | | | | 1070 |
| | Met | Thr | Ala | Ile | Ile | Lys | Glu | Ile | Val | Ser | Arg | Asn | | | | |
| | 1 | | | 5 | | | | | 10 | | | | | | | |

| aaa | agg | aga | tat | caa | gag | gat | gga | ttc | gac | tta | gac | ttg | acc | tat | att | 1118 |
|---|---|---|---|---|---|---|---|---|---|---|---|---|---|---|---|---|
| Lys | Arg | Arg | Tyr | Gln | Glu | Asp | Gly | Phe | Asp | Leu | Asp | Leu | Thr | Tyr | Ile | |
| | 15 | | | | 20 | | | | | 25 | | | | | | |

| tat | cca | aac | att | att | gct | atg | gga | ttt | cct | gca | gaa | aga | ctt | gaa | ggc | 1166 |
|---|---|---|---|---|---|---|---|---|---|---|---|---|---|---|---|---|
| Tyr | Pro | Asn | Ile | Ile | Ala | Met | Gly | Phe | Pro | Ala | Glu | Arg | Leu | Glu | Gly | |
| 30 | | | | | 35 | | | | | 40 | | | | | | |

| gta | tac | agg | aac | aat | att | gat | gat | gta | gta | agg | ttt | ttg | gat | tca | aag | 1214 |
|---|---|---|---|---|---|---|---|---|---|---|---|---|---|---|---|---|
| Val | Tyr | Arg | Asn | Asn | Ile | Asp | Asp | Val | Val | Arg | Phe | Leu | Asp | Ser | Lys | |
| 45 | | | | 50 | | | | | 55 | | | | | | 60 | |

| cat | aaa | aac | cat | tac | aag | ata | tac | aat | ctt | tgt | gct | gaa | aga | cat | tat | 1262 |
|---|---|---|---|---|---|---|---|---|---|---|---|---|---|---|---|---|
| His | Lys | Asn | His | Tyr | Lys | Ile | Tyr | Asn | Leu | Cys | Ala | Glu | Arg | His | Tyr | |
| | | | | 65 | | | | | 70 | | | | | 75 | | |

| gac | acc | gcc | aaa | ttt | aat | tgc | aga | gtt | gca | caa | tat | cct | ttt | gaa | gac | 1310 |
|---|---|---|---|---|---|---|---|---|---|---|---|---|---|---|---|---|
| Asp | Thr | Ala | Lys | Phe | Asn | Cys | Arg | Val | Ala | Gln | Tyr | Pro | Phe | Glu | Asp | |
| | | | 80 | | | | | 85 | | | | | 90 | | | |

| cat | aac | cca | cca | cag | cta | gaa | ctt | atc | aaa | ccc | ttt | tgt | gaa | gat | ctt | 1358 |
|---|---|---|---|---|---|---|---|---|---|---|---|---|---|---|---|---|
| His | Asn | Pro | Pro | Gln | Leu | Glu | Leu | Ile | Lys | Pro | Phe | Cys | Glu | Asp | Leu | |
| | | 95 | | | | | 100 | | | | | 105 | | | | |

| gac | caa | tgg | cta | agt | gaa | gat | gac | aat | cat | gtt | gca | gca | att | cac | tgt | 1406 |
|---|---|---|---|---|---|---|---|---|---|---|---|---|---|---|---|---|
| Asp | Gln | Trp | Leu | Ser | Glu | Asp | Asp | Asn | His | Val | Ala | Ala | Ile | His | Cys | |
| | 110 | | | | | 115 | | | | | 120 | | | | | |

| aaa | gct | gga | aag | gga | cga | act | ggt | gta | atg | ata | tgt | gca | tat | tta | tta | 1454 |
|---|---|---|---|---|---|---|---|---|---|---|---|---|---|---|---|---|
| Lys | Ala | Gly | Lys | Gly | Arg | Thr | Gly | Val | Met | Ile | Cys | Ala | Tyr | Leu | Leu | |
| 125 | | | | | 130 | | | | | 135 | | | | | 140 | |

| cat | cgg | ggc | aaa | ttt | tta | aag | gca | caa | gag | gcc | cta | gat | ttc | tat | ggg | 1502 |
|---|---|---|---|---|---|---|---|---|---|---|---|---|---|---|---|---|
| His | Arg | Gly | Lys | Phe | Leu | Lys | Ala | Gln | Glu | Ala | Leu | Asp | Phe | Tyr | Gly | |
| | | | | 145 | | | | | 150 | | | | | 155 | | |

| gaa | gta | agg | acc | aga | gac | aaa | aag | gga | gta | act | att | ccc | agt | cag | agg | 1550 |
|---|---|---|---|---|---|---|---|---|---|---|---|---|---|---|---|---|
| Glu | Val | Arg | Thr | Arg | Asp | Lys | Lys | Gly | Val | Thr | Ile | Pro | Ser | Gln | Arg | |
| | | | 160 | | | | | 165 | | | | | 170 | | | |

| cgc | tat | gtg | tat | tat | tat | agc | tac | ctg | tta | aag | aat | cat | ctg | gat | tat | 1598 |
|---|---|---|---|---|---|---|---|---|---|---|---|---|---|---|---|---|
| Arg | Tyr | Val | Tyr | Tyr | Tyr | Ser | Tyr | Leu | Leu | Lys | Asn | His | Leu | Asp | Tyr | |
| | 175 | | | | | 180 | | | | | 185 | | | | | |

| aga | cca | gtg | gca | ctg | ttg | ttt | cac | aag | atg | atg | ttt | gaa | act | att | cca | 1646 |
|---|---|---|---|---|---|---|---|---|---|---|---|---|---|---|---|---|
| Arg | Pro | Val | Ala | Leu | Leu | Phe | His | Lys | Met | Met | Phe | Glu | Thr | Ile | Pro | |
| | 190 | | | | | 195 | | | | | 200 | | | | | |

| atg | ttc | agt | ggc | gga | act | tgc | aat | cct | cag | ttt | gtg | gtc | tgc | cag | cta | 1694 |
|---|---|---|---|---|---|---|---|---|---|---|---|---|---|---|---|---|

```
Met Phe Ser Gly Gly Thr Cys Asn Pro Gln Phe Val Val Cys Gln Leu
205                 210                 215                 220 aag gtg aag ata tat tcc tcc aat tca gga ccc aca cga cgg gaa gac      1742
Lys Val Lys Ile Tyr Ser Ser Asn Ser Gly Pro Thr Arg Arg Glu Asp
                    225                 230                 235 aag ttc atg tac ttt gag ttc cct cag ccg tta cct gtg tgt ggt gat      1790
Lys Phe Met Tyr Phe Glu Phe Pro Gln Pro Leu Pro Val Cys Gly Asp
                240                 245                 250 atc aaa gta gag ttc ttc cac aaa cag aac aag atg cta aaa aag gac      1838
Ile Lys Val Glu Phe Phe His Lys Gln Asn Lys Met Leu Lys Lys Asp
            255                 260                 265 aaa atg ttt cac ttt tgg gta aat aca ttc ttc ata cca gga cca gag      1886
Lys Met Phe His Phe Trp Val Asn Thr Phe Phe Ile Pro Gly Pro Glu
        270                 275                 280 gaa acc tca gaa aaa gta gaa aat gga agt cta tgt gat caa gaa atc      1934
Glu Thr Ser Glu Lys Val Glu Asn Gly Ser Leu Cys Asp Gln Glu Ile
285                 290                 295                 300 gat agc att tgc agt ata gag cgt gca gat aat gac aag gaa tat cta      1982
Asp Ser Ile Cys Ser Ile Glu Arg Ala Asp Asn Asp Lys Glu Tyr Leu
                305                 310                 315 gta ctt act tta aca aaa aat gat ctt gac aaa gca aat aaa gac aaa      2030
Val Leu Thr Leu Thr Lys Asn Asp Leu Asp Lys Ala Asn Lys Asp Lys
            320                 325                 330 gcc aac cga tac ttt tct cca aat ttt aag gtg aag ctg tac ttc aca      2078
Ala Asn Arg Tyr Phe Ser Pro Asn Phe Lys Val Lys Leu Tyr Phe Thr
        335                 340                 345 aaa aca gta gag gag ccg tca aat cca gag gct agc agt tca act tct      2126
Lys Thr Val Glu Glu Pro Ser Asn Pro Glu Ala Ser Ser Ser Thr Ser
350                 355                 360 gta aca cca gat gtt agt gac aat gaa cct gat cat tat aga tat tct      2174
Val Thr Pro Asp Val Ser Asp Asn Glu Pro Asp His Tyr Arg Tyr Ser
365                 370                 375                 380 gac acc act gac tct gat cca gag aat gaa cct ttt gat gaa gat cag      2222
Asp Thr Thr Asp Ser Asp Pro Glu Asn Glu Pro Phe Asp Glu Asp Gln
                385                 390                 395 cat aca caa att aca aaa gtc tga atttttttt atcaagaggg ataaaacacc      2276
His Thr Gln Ile Thr Lys Val
                400 atgaaaataa acttgaataa actgaaaatg gaccttttt ttttaatgg caataggaca      2336 ttgtgtcaga ttaccagtta taggaacaat tctcttttcc tgaccaatct tgttttaccc   2396 tatacatcca cagggttttg acacttgttg tccagttgaa aaaaggttgt gtagctgtgt   2456 catgtatata cctttttgtg tcaaaaggac atttaaaatt caattaggat taataaagat   2516 ggcactttcc cgttttattc cagtttata  aaaagtggag acagactgat gtgtatacgt   2576 aggaattttt tccttttgtg ttctgtcacc aactgaagtg gctaaagagc tttgtgtatat  2636 actggttcac atcctacccc tttgcacttg tggcaacaga taagtttgca gttggctaag   2696 agaggtttcc gaaaggtttt gctaccattc taatgcatgt attcgggtta gggcaatgga   2756 ggggaatgct cagaaaggaa ataatttat gctggactct ggaccatata ccatctccag    2816 ctatttacac acacctttct ttagcatgct acagttatta atctggacat tcgaggaatt   2876 ggccgctgtc actgcttgtt gtttgcgcat ttttttttaa agcatattgg tgctagaaaa   2936 ggcagctaaa ggaagtgaat ctgtattggg gtacaggaat gaaccttctg caacatctta   2996 agatccacaa atgaagggat ataaaataa tgtcataggt aagaaacaca gcaacaatga    3056 cttaaccata taaatgtgga ggctatcaac aaagaatggg cttgaaacat tataaaaatt   3116
```

```
gacaatgatt tattaaatat gttttctcaa ttgtaaaaaa aaaa                    3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                        26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                         25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                    30

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 5
cttagcactg gcct                                                     14

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 6
tcagtcatga cttc                                                     14

<210> SEQ ID NO 7
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 7
ucaaggccag ugcuaagagu                                               20
```